US009957330B2

United States Patent
Abrahmsén et al.

(10) Patent No.: US 9,957,330 B2
(45) Date of Patent: May 1, 2018

(54) POLYPEPTIDES

(71) Applicant: AFFIBODY AB, Solna (SE)

(72) Inventors: Lars Abrahmsén, Stockholm (SE); Ingmarie Höidén-Guthenberg, Kista (SE); Elin Gunneriusson, Satlsjöbaden (SE)

(73) Assignee: AFFIBODY AB, Solna (SE)

( * ) Notice: Subject to any disclaimer, the term of this patent is extended or adjusted under 35 U.S.C. 154(b) by 0 days. days.

(21) Appl. No.: 14/442,603

(22) PCT Filed: Dec. 19, 2013

(86) PCT No.: PCT/EP2013/077334
§ 371 (c)(1),
(2) Date: May 13, 2015

(87) PCT Pub. No.: WO2014/096163
PCT Pub. Date: Jun. 26, 2014

(65) Prior Publication Data
US 2016/0289337 A1 Oct. 6, 2016

Related U.S. Application Data

(60) Provisional application No. 61/739,103, filed on Dec. 19, 2012.

(30) Foreign Application Priority Data

Dec. 19, 2012 (EP) .................................... 12198109

(51) Int. Cl.
| | | |
|---|---|---|
| *C07K 16/40* | (2006.01) | |
| *C07K 16/30* | (2006.01) | |
| *C07K 14/47* | (2006.01) | |
| *C07K 14/435* | (2006.01) | |

(52) U.S. Cl.
CPC ............ *C07K 16/40* (2013.01); *C07K 14/435* (2013.01); *C07K 14/47* (2013.01); *C07K 16/30* (2013.01); *C07K 2317/92* (2013.01); *C07K 2318/20* (2013.01)

(58) Field of Classification Search
None
See application file for complete search history.

(56) References Cited

U.S. PATENT DOCUMENTS 9,187,535 B2 * 11/2015 Lindborg ............... C07K 14/31
9,211,344 B2 * 12/2015 Ekblad ................. C07K 14/315
2008/0299136 A1 * 12/2008 Ernst .................. C07K 14/4702
424/178.1
2011/0021424 A1 * 1/2011 Lindborg ............... C07K 14/31
514/7.5
2012/0270801 A1 * 10/2012 Frejd ..................... C07K 14/31
514/19.4

FOREIGN PATENT DOCUMENTS

| WO | 2009077175 A1 | | 6/2009 |
|---|---|---|---|
| WO | WO 2009077175 | * | 6/2009 |
| WO | 2011056124 A1 | | 5/2011 |
| WO | WO 2011056124 | * | 5/2011 |

OTHER PUBLICATIONS

McDonald et al. "Recent developments in targeting carbonic anhydrase IX for cancer therapeutics.", Oncotarget Jan. 2012, vol. 3, No. 1, Jan. 28, 2012 (Jan. 28, 2012), pp. 84-97.*
Grönwall et al., "Selection and Characterization of Affibody Ligands Binding to Alzheimer Amyloid β Peptides" Journal of Biotechnology; 128; (2007); pp. 162-183.
Gunneriusson et al., "Affinity Maturation of a Taq DNA Polymerase Specific Affibody by Helix Shuffling" Protein Engineering; vol. 12; No. 10; (1999); pp. 873-878.
International Search Report of the International Searching Authority for International Patent Application No. PCT/EP2013/077334; Date of Filing: Dec. 19, 2013; dated Mar. 10, 2014; 3 Pages.
McDonald et al., "Recent Developments in Targeting Carbonic Anhydrase IX for Cancer Therapeutics" Oncotarget; 3; (2012); pp. 84-97.
Orlova et al., "Tumor Imaging Using a Picomolar Affinity HER2 Binding Affibody Molecule" Cancer Research; 66(8); Apr. 15, 2006; pp. 4339-4348.
International Preliminary Report on Patentability of the International Searching Authority for International Patent Application No. PCT/EP2013/077334; International Filing Date: Dec. 19, 2013; dated Jul. 2, 2015; 2 Pages.
Written Opinion of the International Searching Authority for International Patent Application No. PCT/EP2013/077334; International Filing Date: Dec. 19, 2013; dated Mar. 10, 2014; 5 Pages.

* cited by examiner

*Primary Examiner* — Maury Audet
(74) *Attorney, Agent, or Firm* — Cantor Colburn LLP

(57) ABSTRACT

The present disclosure relates to a class of engineered polypeptides having a binding affinity for carbonic anhydrase IX (CAIX), and provides a CAIX binding polypeptide comprising the sequence $EX_2X_3X_4AX_6X_7EIX_{10}X_{11}LPN\ LX_{16}X_{17}X_{18}QX_{20}\ X_{21}AFIX_{25}X_{26}LWD$.

The present disclosure also relates to the use of such a CAIX binding polypeptide as a diagnostic, prognostic agent and/or therapeutic agent.

19 Claims, 22 Drawing Sheets

Figure 1A

| Designation | Amino acid sequence | SEQ ID NO: |
|---|---|---|
| | ENLFAGWEIDDLPNLTEDQRNAFIYKLWD | SEQ ID NO:1 |
| | ENLFAGNEISDLPNLTDYQRNAFIYKLWD | SEQ ID NO:2 |
| | ENIFAGWEIDDLPNLTDEQRNAFIYKLWD | SEQ ID NO:3 |
| | ENIFAGWEIDDLPNLTESQRNAFIYKLWD | SEQ ID NO:4 |
| | EWWWAGIEIADLPNLTQQRDAFIYKLWD | SEQ ID NO:5 |
| | EHLFAGWEIEDLPNLTEYQRNAFIYKLWD | SEQ ID NO:6 |
| | ENLFAGWEITDLPNLTIEQRNAFIYKLWD | SEQ ID NO:7 |
| | ENLFAGNEIGDLPNLTEQQRHAFIYKLWD | SEQ ID NO:8 |
| | ENLFAGWEITDLPNLTIQQRNAFIYKLWD | SEQ ID NO:9 |
| | ENIFAGWEITDLPNLTTYQRNAFIYKLWD | SEQ ID NO:10 |
| | ENLFAGWEINDLPNLHEYQRNAFIYKLWD | SEQ ID NO:11 |
| | EHLFAGWEITDLPNLTEQQRNAFIYKLWD | SEQ ID NO:12 |
| | ENIFAGWEITDLPNLTVQQRNAFIYKLWD | SEQ ID NO:13 |
| | ENIFAGWEIDELPNLTEYQRNAFIYKLWD | SEQ ID NO:14 |
| | EHIFAGWEITDLPNLTDDQRNAFIYKLWD | SEQ ID NO:15 |
| | ENFAGWEISDLPNLTVAQRNAFIYKLWD | SEQ ID NO:16 |
| | ENLFAGWEITDLPNLTEYQRNAFIYKLWD | SEQ ID NO:17 |
| | EDLFAGWEITDLPNLTESQRHAFIYKLWD | SEQ ID NO:18 |
| | ENIFAGWEITDLPNLTFDYQRHAFIYKLWD | SEQ ID NO:19 |
| | ENLFAGWEISDLPNLTQQQRHAFIYKLWD | SEQ ID NO:20 |
| | ENLFAGWEIEDLPNLTDHQRNAFIYKLWD | SEQ ID NO:21 |
| | ENIFAGWEIRDLPNLTDYQRNAFIYKLWD | SEQ ID NO:22 |
| | ENWAAGWEISDLPNLTDFQRNAFIYKLWD | SEQ ID NO:23 |
| | ENIFAGWEIGDLPNLTEDQRNAFIYKLWD | SEQ ID NO:24 |
| | ENIFAGWEIDDLPNLTEAQRNAFIYKLWD | SEQ ID NO:25 |
| | EQLFAGWEIDDLPNLTEFQRNAFIYKLWD | SEQ ID NO:26 |
| | EWRYASIEIADLPNLTQRQRDAFIYKLWD | SEQ ID NO:27 |
| | ENWAAGWEIDDLPNLTIDQRNAFIYKLWD | SEQ ID NO:28 |

Figure 1B

| Sequence | SEQ ID |
|---|---|
| EQLFAGWEIDDLPNLTDFQRNAFIYKLWD | SEQ ID NO:29 |
| ENLFAGWEIEELPNLTEFQRNAFIYKLWD | SEQ ID NO:30 |
| ENLFAGWEIGDLPNLTEDQRNAFIYKLWD | SEQ ID NO:31 |
| ENIFAGWEIEDLPNLTDQQRNAFIYKLWD | SEQ ID NO:32 |
| EHIFAGWEISDLPNLTEQQRHAFIYKLWD | SEQ ID NO:33 |
| ENLFAGWEIDDLPNLTVQQRNAFIYKLWD | SEQ ID NO:34 |
| EHLFAGWEIDDLPNLTDHQRNAFIYKLWD | SEQ ID NO:35 |
| ENIFAGWEISDLPNLTIDQRNAFIYKLWD | SEQ ID NO:36 |
| ENIWAGWEIDDLPNLTERQRNAFIYKLWD | SEQ ID NO:37 |
| ENIFAGWEIEDLPNLTDGQRNAFIYKLWD | SEQ ID NO:38 |
| ENIFAGWEISDLPNLTEHQRNAFIYKLWD | SEQ ID NO:39 |
| ENIFAGWEIEDLPNLTDHQRDAFIYKLWD | SEQ ID NO:40 |
| EHWAAGWEIEDLPNLTEFQRNAFIYKLWD | SEQ ID NO:41 |
| EHLFAGWEITDLPNLTDQQRDAFIYKLWD | SEQ ID NO:42 |
| EQLFAGWEIDDLPNLTEAQRNAFIYKLWD | SEQ ID NO:43 |
| EQLFAGWEISDLPNLTEQQRHAFIYKLWD | SEQ ID NO:44 |
| ENLFAGWEIDDLPNLTWQQRNAFIYKLWD | SEQ ID NO:45 |
| ENIFAGWEIQDLPNLTIEQRNAFIYKLWD | SEQ ID NO:46 |
| EWWAAGEITELPNLTEQQRDAFIYKLWD | SEQ ID NO:47 |
| EWQWAGVEIQDLPNLTDNQRQAFIYKLWD | SEQ ID NO:48 |
| ENWAAGWEITDLPNLTSSQRNAFIYKLWD | SEQ ID NO:49 |
| EHLFAGWEITDLPNLTIDQRNAFIYKLWD | SEQ ID NO:50 |
| EWRWASIEIADLPNLTQHQRDAFIYKLWD | SEQ ID NO:51 |
| EWWYAAGEISSLPNLTEQQRDAFIYKLWD | SEQ ID NO:52 |
| EWWWAAGEISSLPNLTAQQRDAFIYKLWD | SEQ ID NO:53 |
| EHIFAGWEISDLPNLTIYQRHAFIYKLWD | SEQ ID NO:54 |
| ENIFAGWEIDDLPNLTDNQRHAFIYKLWD | SEQ ID NO:55 |
| EWQWAGVEIAELPNLTQQQRDAFIYKLWD | SEQ ID NO:56 |
| EHIFAGWEITDLPNLTSSQRNAFIYKLWD | SEQ ID NO:57 |

Figure 1C

| Sequence | SEQ ID |
|---|---|
| EWRWAGVEIQDLPNLTQQRDAFIYKLWD | SEQ ID NO:58 |
| EHIFAGWEISDLPNLTIFQRHAFIYKLWD | SEQ ID NO:59 |
| EWQWAGVEIQELPNLTQQQRHAFIYKLWD | SEQ ID NO:60 |
| ENLFAGWEIDDLPNLTIRQRDAFIYKLWD | SEQ ID NO:61 |
| ENYFAGWEIDDLPNLTEQQRNAFIYKLWD | SEQ ID NO:62 |
| ENLFAGWEIADLPNLTDHQRNAFIYKLWD | SEQ ID NO:63 |
| EWSWASVEIADLPNLTQRQRDAFIYKLWD | SEQ ID NO:64 |
| EDIFAGWEITDLPNLTDHQRNAFIYKLWD | SEQ ID NO:65 |
| EQLFAGWEIDDLPNLTIDQRNAFIYKLWD | SEQ ID NO:66 |
| ENWFAGWEIDDLPNLTERQRNAFIYKLWD | SEQ ID NO:67 |
| EHLFAGWEIDELPNLTEQQRHAFIYKLWD | SEQ ID NO:68 |
| ENFWAGWEIDDLPNLTELQRNAFIYKLWD | SEQ ID NO:69 |
| EHLFAGWEIEDLPNLTIDQRNAFIYKLWD | SEQ ID NO:70 |
| ENVFAGWEIDDLPNLTDQQRNAFIYKLWD | SEQ ID NO:71 |
| EHLFAGWEIADLPNLTDGQRNAFIYKLWD | SEQ ID NO:72 |
| ENIWAGWEISDLPNLTDTQRNAFIYKLWD | SEQ ID NO:73 |
| EWQWAGIEIQDLPNLTQRQRDAFIYKLWD | SEQ ID NO:74 |
| EWIFAGWEITDLPNLTDFQRNAFIYKLWD | SEQ ID NO:75 |
| ENWAAGWEIDDLPNLTDQQRDAFIYKLWD | SEQ ID NO:76 |
| EHLFAGWEIDELPNLTAYQRNAFIYKLWD | SEQ ID NO:77 |
| EHIFAGWEIEDLPNLTESQRNAFIYKLWD | SEQ ID NO:78 |
| ENIFAGWEIDDLPNLTAHQRDAFIYKLWD | SEQ ID NO:79 |
| ENLFAGWEIGDLPNLTTGQRHAFIYKLWD | SEQ ID NO:80 |
| EHLFAGWEISDLPNLTANQRDAFIYKLWD | SEQ ID NO:81 |
| EQLFAGWEIDDLPNLTDQQRHAFIYKLWD | SEQ ID NO:82 |
| EWQWAGVEINDLPNLTQQQRHAFIYKLWD | SEQ ID NO:83 |
| EWWYAGVEIADLPNLTQQQRDAFIYKLWD | SEQ ID NO:84 |
| EQWWAGVEIDDLPNLTEIQRNAFIYKLWD | SEQ ID NO:85 |
| EWQWAGVEINELPNLTQRQRDAFIYKLWD | SEQ ID NO:86 |

Figure 1D

| | |
|---|---|
| ENIWAGWEISDLPNLTEDQRNAFIYKLWD | SEQ ID NO:87 |
| EHIFAGWEIEELPNLTDTQRNAFIYKLWD | SEQ ID NO:88 |
| EDLWAGWEITDLPNLTEWQRHAFIYKLWD | SEQ ID NO:89 |
| ENIFAGWEIEDLPNLTDNQRDAFIYKLWD | SEQ ID NO:90 |
| ENIFAGWEINDLPNLTEQQRNAFIYKLWD | SEQ ID NO:91 |
| ENIWAGWEIDDLPNLTVNQRDAFIYKLWD | SEQ ID NO:92 |
| EQWWAGWEIDDLPNLTEDQRNAFIYKLWD | SEQ ID NO:93 |
| EHTNAWAEIHRLPNLTESQQNAFIYKLWD | SEQ ID NO:94 |
| EWWYAGEEIADLPNLTQQCQDAFIYKLWD | SEQ ID NO:95 |
| EWQAGVEINELPNLTWQQRQAFIYKLWD | SEQ ID NO:96 |
| EWQWAGWEINDLPNLTQQQRDAFIYKLWD | SEQ ID NO:97 |
| EWRWAGVEIAELPNLTQNCRDAFIYKLWD | SEQ ID NO:98 |
| EHLFAGWEIGDLPNLTEQQRHAFIYKLWD | SEQ ID NO:99 |
| ENLFAGWEIHDLPNLTDDQRNAFIYKLWD | SEQ ID NO:100 |
| ENLFAGWEIDDLPNLTEVQRNAFIYKLWD | SEQ ID NO:101 |
| ENLFAGWEITDLPNLTASCRNAFIYKLWD | SEQ ID NO:102 |
| EWWWAAGEIEISDLPNLTGQQRDAFIYKLWD | SEQ ID NO:103 |
| ENIFAGWEIVDLPNLTEIQRNAFIYKLWD | SEQ ID NO:104 |
| ENLFAGWEIRDLPNLTEAQRHAFIYKLWD | SEQ ID NO:105 |
| ENWWAGWEITDLPNLTEHQRHAFIYKLWD | SEQ ID NO:106 |
| EHLFAGWEIQDLPNLTEDQRNAFIYKLWD | SEQ ID NO:107 |
| ENIWAGWEIGDLPNLTEQQRHAFIYKLWD | SEQ ID NO:108 |
| EWQWAGVEIQDLPNLTGQQRDAFIYKLWD | SEQ ID NO:109 |
| EQIFAGWEITDLPNLTEAQRNAFIYKLWD | SEQ ID NO:110 |
| ENIWAGWEIGDLPNLTDQQRDAFIYKLWD | SEQ ID NO:111 |
| EWSWASVEIADLPNLTQQQRDAFIYKLWD | SEQ ID NO:112 |
| ENIFAGWEIEDLPNLTVHQRDAFIYKLWD | SEQ ID NO:113 |
| KENLFAGWEIDDLPNLTEDQRNAFIYKLWDDPSQSSELLSEAKKLNDSQ | SEQ ID NO:114 |
| KENLFAGWEISDLPNLTDYQRNAFIYKLWDDPSQSSELLSEAKKLNDSQ | SEQ ID NO:115 |

Figure 1E

| Sequence | SEQ ID |
|---|---|
| KENIFAGWEIDDLPNLTDEQRNAFIYKLWDDPSQSSELLSEAKKLNDSQ | SEQ ID NO:116 |
| KENLFAGWEIDDLPNLTESQRNAFIYKLWDDPSQSSELLSEAKKLNDSQ | SEQ ID NO:117 |
| KEWWAAGIEIADLPNLTQQQRDAFIYKLWDDPSQSSELLSEAKKLNDSQ | SEQ ID NO:118 |
| KEHLFAGWEIEDLPNLTEYQRNAFIYKLWDDPSQSSELLSEAKKLNDSQ | SEQ ID NO:119 |
| KENLFAGWEITDLPNLTIEQRNAFIYKLWDDPSQSSELLSEAKKLNDSQ | SEQ ID NO:120 |
| KENLFAGWEIGDLPNLTEQQRHAFIYKLWDDPSQSSELLSEAKKLNDSQ | SEQ ID NO:121 |
| KENLFAGWEITDLPNLTIQQRNAFIYKLWDDPSQSSELLSEAKKLNDSQ | SEQ ID NO:122 |
| KENIFAGWEIDDLPNLTTYQRNAFIYKLWDDPSQSSELLSEAKKLNDSQ | SEQ ID NO:123 |
| KENLFAGWEINDLPNLTEYQRNAFIYKLWDDPSQSSELLSEAKKLNDSQ | SEQ ID NO:124 |
| KEHLFAGWEITDLPNLTEQQRNAFIYKLWDDPSQSSELLSEAKKLNDSQ | SEQ ID NO:125 |
| KENIFAGWEITDLPNLTVQQRHAFIYKLWDDPSQSSELLSEAKKLNDSQ | SEQ ID NO:126 |
| KENIFAGWEIDELPNLTEYQRNAFIYKLWDDPSQSSELLSEAKKLNDSQ | SEQ ID NO:127 |
| KEHIFAGWEITDLPNLTDDQRNAFIYKLWDDPSQSSELLSEAKKLNDSQ | SEQ ID NO:128 |
| KENIFAGWEISDLPNLTVAQRHAFIYKLWDDPSQSSELLSEAKKLNDSQ | SEQ ID NO:129 |
| KEDLFAGWEIDDLPNLTEYQRNAFIYKLWDDPSQSSELLSEAKKLNDSQ | SEQ ID NO:130 |
| KENIFAGWEIRDLPNLTESQRNAFIYKLWDDPSQSSELLSEAKKLNDSQ | SEQ ID NO:131 |
| KENLFAGWEITDLPNLTDYQRNAFIYKLWDDPSQSSELLSEAKKLNDSQ | SEQ ID NO:132 |
| KENLFAGWEIEDLPNLTDQRNAFIYKLWDDPSQSSELLSEAKKLNDSQ | SEQ ID NO:133 |
| KENIFAGWEISDLPNLTQQQRHAFIYKLWDDPSQSSELLSEAKKLNDSQ | SEQ ID NO:134 |
| KENIFAGWEIEDLPNLTDHQRNAFIYKLWDDPSQSSELLSEAKKLNDSQ | SEQ ID NO:135 |
| KENIFAGWEIRDLPNLTFDYQRNAFIYKLWDDPSQSSELLSEAKKLNDSQ | SEQ ID NO:136 |
| KENWAAGWEISDLPNLTDFQRNAFIYKLWDDPSQSSELLSEAKKLNDSQ | SEQ ID NO:137 |
| KENIFAGWEIGDLPNLTEDQRNAFIYKLWDDPSQSSELLSEAKKLNDSQ | SEQ ID NO:138 |
| KEQLFAGWEIDDLPNLTEAQRHAFIYKLWDDPSQSSELLSEAKKLNDSQ | SEQ ID NO:139 |
| KENIFAGWEIDDLPNLTEFQRNAFIYKLWDDPSQSSELLSEAKKLNDSQ | SEQ ID NO:140 |
| KEWRYASIEIADLPNLTQRQRDAFIYKLWDDPSQSSELLSEAKKLNDSQ | SEQ ID NO:141 |
| KENWAAGWEIDDLPNLTIDQRNAFIYKLWDDPSQSSELLSEAKKLNDSQ | SEQ ID NO:142 |
| KEQLFAGWEIEELPNLTEFQRNAFIYKLWDDPSQSSELLSEAKKLNDSQ | SEQ ID NO:143 |
| KENLFAGWEIGDLPNLTEDQRNAFIYKLWDDPSQSSELLSEAKKLNDSQ | SEQ ID NO:144 |

Figure 1F

| Sequence | SEQ ID |
|---|---|
| KENIFAGWEIEDLPNLTDQQRNAFIYKLWDDPSQSSELLSEAKKLNDSQ | SEQ ID NO:145 |
| KEHIFAGWEISDLPNLTEQQRHAFIYKLWDDPSQSSELLSEAKKLNDSQ | SEQ ID NO:146 |
| KENLFAGWEIDDLPNLTVQQRNAFIYKLWDDPSQSSELLSEAKKLNDSQ | SEQ ID NO:147 |
| KEHLFAGWEIDDLPNLTDHQRNAFIYKLWDDPSQSSELLSEAKKLNDSQ | SEQ ID NO:148 |
| KENIFAGWEISDLPNLTIDQRNAFIYKLWDDPSQSSELLSEAKKLNDSQ | SEQ ID NO:149 |
| KENIWAGWEIDDLPNLTERQRNAFIYKLWDDPSQSSELLSEAKKLNDSQ | SEQ ID NO:150 |
| KENIFAGWEIEDLPNLTDGQRNAFIYKLWDDPSQSSELLSEAKKLNDSQ | SEQ ID NO:151 |
| KEHIFAGWEISDLPNLTEHQRNAFIYKLWDDPSQSSELLSEAKKLNDSQ | SEQ ID NO:152 |
| KENIFAGWEIEDLPNLTDHQRDAFIYKLWDDPSQSSELLSEAKKLNDSQ | SEQ ID NO:153 |
| KEHWAAGWEIDDLPNLTEFQRNAFIYKLWDDPSQSSELLSEAKKLNDSQ | SEQ ID NO:154 |
| KEHLFAGWEITDLPNLTDQQRDAFIYKLWDDPSQSSELLSEAKKLNDSQ | SEQ ID NO:155 |
| KEQLFAGWEIDDLPNLTEAQRNAFIYKLWDDPSQSSELLSEAKKLNDSQ | SEQ ID NO:156 |
| KEQIFAGWEISDLPNLTEQQRHAFIYKLWDDPSQSSELLSEAKKLNDSQ | SEQ ID NO:157 |
| KENLFAGWEIDDLPNLTWQQRHAFIYKLWDDPSQSSELLSEAKKLNDSQ | SEQ ID NO:158 |
| KENIFAGWEIQDLPNLTIEQRNAFIYKLWDDPSQSSELLSEAKKLNDSQ | SEQ ID NO:159 |
| KEWWAAGEITELPNLTEQQRNAFIYKLWDDPSQSSELLSEAKKLNDSQ | SEQ ID NO:160 |
| KEWQWAGVEIQDLPNLTDNRQAFIYKLWDDPSQSSELLSEAKKLNDSQ | SEQ ID NO:161 |
| KENWAAGWEITDLPNLTSSQRNAFIYKLWDDPSQSSELLSEAKKLNDSQ | SEQ ID NO:162 |
| KEHLFAGWEITDLPNLTDQQRDAFIYKLWDDPSQSSELLSEAKKLNDSQ | SEQ ID NO:163 |
| KEWRASIEIADLPNLTQHQRDAFIYKLWDDPSQSSELLSEAKKLNDSQ | SEQ ID NO:164 |
| KEWWYAAGEISSLFNLTEQQRDAFIYKLWDDPSQSSELLSEAKKLNDSQ | SEQ ID NO:165 |
| KEWWAAGEISSLPNLTAQQRDAFIYKLWDDPSQSSELLSEAKKLNDSQ | SEQ ID NO:166 |
| KEHIFAGWEISDLPNLTIYQRHAFIYKLWDDPSQSSELLSEAKKLNDSQ | SEQ ID NO:167 |
| KENIFAGWEIDDLPNLTDNQRHAFIYKLWDDPSQSSELLSEAKKLNDSQ | SEQ ID NO:168 |
| KEWQWAGVEIAELPNLTQQQRDAFIYKLWDDPSQSSELLSEAKKLNDSQ | SEQ ID NO:169 |
| KEHIFAGWEITDLPNLTSSQRNAFIYKLWDDPSQSSELLSEAKKLNDSQ | SEQ ID NO:170 |
| KEWRWAGVEIQDLPNLTQQQRNAFIYKLWDDPSQSSELLSEAKKLNDSQ | SEQ ID NO:171 |
| KENIFAGWEISDLPNLTIFQRHAFIYKLWDDPSQSSELLSEAKKLNDSQ | SEQ ID NO:172 |
| KEWQWAGVEIQELPNLTQQQRHAFIYKLWDDPSQSSELLSEAKKLNDSQ | SEQ ID NO:173 |

Figure 1G

| Sequence | SEQ ID NO |
|---|---|
| KENLFAGWEIDDLPNLTIRQRDAFIYKLWDDPSQSSELLSEAKKLNDSQ | SEQ ID NO:174 |
| KENYFAGWEIDDLPNLTEQQRNAFIYKLWDDPSQSSELLSEAKKLNDSQ | SEQ ID NO:175 |
| KENLFAGWEIADLPNLTDHQRNAFIYKLWDDPSQSSELLSEAKKLNDSQ | SEQ ID NO:176 |
| KEWSWASVEIADLPNLTQRQRDAFIYKLWDDPSQSSELLSEAKKLNDSQ | SEQ ID NO:177 |
| KEDIFAGWEITDLPNLTDHQRNAFIYKLWDDPSQSSELLSEAKKLNDSQ | SEQ ID NO:178 |
| KEQLFAGWEIDDLPNLTIDQRNAFIYKLWDDPSQSSELLSEAKKLNDSQ | SEQ ID NO:179 |
| KENWFAGWEIDDLPNLTERQRNAFIYKLWDDPSQSSELLSEAKKLNDSQ | SEQ ID NO:180 |
| KEHLFAGWEIDELPNLTEQQRNAFIYKLWDDPSQSSELLSEAKKLNDSQ | SEQ ID NO:181 |
| KENFWAGWEIDDLPNLTELQRNAFIYKLWDDPSQSSELLSEAKKLNDSQ | SEQ ID NO:182 |
| KENLFAGWEIDDLPNLTIDQRNAFIYKLWDDPSQSSELLSEAKKLNDSQ | SEQ ID NO:183 |
| KENVFAGWEIDDLPNLTDQQRNAFIYKLWDDPSQSSELLSEAKKLNDSQ | SEQ ID NO:184 |
| KEHIFAGWEIADLPNLTDGQRNAFIYKLWDDPSQSSELLSEAKKLNDSQ | SEQ ID NO:185 |
| KENIWAGWEIDELPNLTDTQRNAFIYKLWDDPSQSSELLSEAKKLNDSQ | SEQ ID NO:186 |
| KEWQWAGIEIQDLPNLTQRQRDAFIYKLWDDPSQSSELLSEAKKLNDSQ | SEQ ID NO:187 |
| KEWIFAGWEITDLPNLTDFQRNAFIYKLWDDPSQSSELLSEAKKLNDSQ | SEQ ID NO:188 |
| KENWAAGWEIDDLPNLTDQQRNAFIYKLWDDPSQSSELLSEAKKLNDSQ | SEQ ID NO:189 |
| KEHLFAGWEIDELPNLTAYQRNAFIYKLWDDPSQSSELLSEAKKLNDSQ | SEQ ID NO:190 |
| KEHIFAGWEIDELPNLTESQRNAFIYKLWDDPSQSSELLSEAKKLNDSQ | SEQ ID NO:191 |
| KENIFAGWEIDDLPNLTAHQRDAFIYKLWDDPSQSSELLSEAKKLNDSQ | SEQ ID NO:192 |
| KENLFAGWEIGDLPNLTTGQRNAFIYKLWDDPSQSSELLSEAKKLNDSQ | SEQ ID NO:193 |
| KEHLFAGWEISDLPNLTANQRDAFIYKLWDDPSQSSELLSEAKKLNDSQ | SEQ ID NO:194 |
| KEQLFAGWEIDDLPNLTDQQRNAFIYKLWDDPSQSSELLSEAKKLNDSQ | SEQ ID NO:195 |
| KEWQWAGVEINDLPNLTQRQRDAFIYKLWDDPSQSSELLSEAKKLNDSQ | SEQ ID NO:196 |
| KEWWYAGVEIADLPNLTQQQRDAFIYKLWDDPSQSSELLSEAKKLNDSQ | SEQ ID NO:197 |
| KEQWWAGWEIDDLPNLTEIQRNAFIYKLWDDPSQSSELLSEAKKLNDSQ | SEQ ID NO:198 |
| KEFWQWAGVEINELPNLTQRQRDAFIYKLWDDPSQSSELLSEAKKLNDSQ | SEQ ID NO:199 |
| KENIWAGWEISDLPNLTEDQRNAFIYKLWDDPSQSSELLSEAKKLNDSQ | SEQ ID NO:200 |
| KEHIFAGWEIEELPNLTDTQRNAFIYKLWDDPSQSSELLSEAKKLNDSQ | SEQ ID NO:201 |
| KEDLWAGWEITDLPNLTEWQRHAFIYKLWDDPSQSSELLSEAKKLNDSQ | SEQ ID NO:202 |

Figure 1H

| | | |
|---|---|---|
| | KENIFAGWEIEDLPNLTDNQRDAFIYKLWDDPSQSSELLSEAKKLNDSQ | SEQ ID NO:203 |
| | KENLWAGWEINDLPNLTEQQRNAFIYKLWDDPSQSSELLSEAKKLNDSQ | SEQ ID NO:204 |
| | KENIWAGWEIDDLPNLTVNQRDAFIYKLWDDPSQSSELLSEAKKLNDSQ | SEQ ID NO:205 |
| | KEQWWAGWEIDDLPNLTEDQRNAFIYKLWDDPSQSSELLSEAKKLNDSQ | SEQ ID NO:206 |
| | KEHTNAWAEIHRLPNLTESQQNAFIYKLWDDPSQSSELLSEAKKLNDSQ | SEQ ID NO:207 |
| | KEWWYAGEIADLPNLTQQQDAFIYKLWDDPSQSSELLSEAKKLNDSQ | SEQ ID NO:208 |
| | KEWQWAGVEINELPNLTWQQRQAFIYKLWDDPSQSSELLSEAKKLNDSQ | SEQ ID NO:209 |
| | KEWQWAGVEINDLPNLTQQQDRDAFIYKLWDDPSQSSELLSEAKKLNDSQ | SEQ ID NO:210 |
| | KEWRWAGVEIAELPNLTQNQRDAFIYKLWDDPSQSSELLSEAKKLNDSQ | SEQ ID NO:211 |
| | KEHLFAGWEIGDLPNLTECQRHAFIYKLWDDPSQSSELLSEAKKLNDSQ | SEQ ID NO:212 |
| | KENLFAGWEIHDLPNLTDDQRNAFIYKLWDDPSQSSELLSEAKKLNDSQ | SEQ ID NO:213 |
| | KENLFAGWEIDDLPNLTEVQRNAFIYKLWDDPSQSSELLSEAKKLNDSQ | SEQ ID NO:214 |
| | KENLFAGWEITDLPNLTASQRHAFIYKLWDDPSQSSELLSEAKKLNDSQ | SEQ ID NO:215 |
| | KEWWAAGEISDLPNLTGQQRDAFIYKLWDDPSQSSELLSEAKKLNDSQ | SEQ ID NO:216 |
| | KENIFAGWEIVDLPNLTEIQRNAFIYKLWDDPSQSSELLSEAKKLNDSQ | SEQ ID NO:217 |
| | KENLFAGWEIRDLPNLTEAQRHAFIYKLWDDPSQSSELLSEAKKLNDSQ | SEQ ID NO:218 |
| | KENWWAGWEITDLPNLTEHQRHAFIYKLWDDPSQSSELLSEAKKLNDSQ | SEQ ID NO:219 |
| | KEHLFAGWEIQDLPNLTEDQRNAFIYKLWDDPSQSSELLSEAKKLNDSQ | SEQ ID NO:220 |
| | KENIWAGWEIGDLPNLTEQQRHAFIYKLWDDPSQSSELLSEAKKLNDSQ | SEQ ID NO:221 |
| | KEWQWAGVEIQDLPNLTGQQRDAFIYKLWDDPSQSSELLSEAKKLNDSQ | SEQ ID NO:222 |
| | KEQIFAGWEITDLPNLTEAQRNAFIYKLWDDPSQSSELLSEAKKLNDSQ | SEQ ID NO:223 |
| | KENIWAGWEIGDLPNLTDQQRNAFIYKLWDDPSQSSELLSEAKKLNDSQ | SEQ ID NO:224 |
| | KEWSWASVEIADLPNLTQQQRDAFIYKLWDDPSQSSELLSEAKKLNDSQ | SEQ ID NO:225 |
| | KENIFAGWEIEDLPNLITVHQRDAFIYKLWDDPSQSSELLSEAKKLNDSQ | SEQ ID NO:226 |
| Z06936 | VDAKYAKENLFAGWEIDDLPNLTEDQRNAFIYKLWDDPSQSSELLSEAKKLNDSQAPK | SEQ ID NO:227 |
| Z06942 | VDAKYAKENLFAGWEISDLPNLTDYQRNAFIYKLWDDPSQSSELLSEAKKLNDSQAPK | SEQ ID NO:228 |
| Z06976 | VDAKYAKENIFAGWEIDDLPNLTDEQRNAFIYKLWDDPSQSSELLSEAKKLNDSQAPK | SEQ ID NO:229 |
| Z07091 | VDAKYAKENLFAGWEIDDLPNLTESQRNAFIYKLWDDPSQSSELLSEAKKLNDSQAPK | SEQ ID NO:230 |
| Z07084 | VDAKYAKEWWWAGIEIADLPNLTQQQRDAFIYKLWDDPSQSSELLSEAKKLNDSQAPK | SEQ ID NO:231 |

Figure 1I

| | | |
|---|---|---|
| Z06919 | VDAKYAKEHLFAGWEIEDLPNLTEYQRNAFIYKLWDDPSQSSELLSEAKKLNDSQAPK | SEQ ID NO:232 |
| Z06959 | VDAKYAKENLFAGWEITDLPNLTEQRNAFIYKLWDDPSQSSELLSEAKKLNDSQAPK | SEQ ID NO:233 |
| Z06961 | VDAKYAKENIFAGWEIGDLPNLTEQQRHAFIYKLWDDPSQSSELLSEAKKLNDSQAPK | SEQ ID NO:234 |
| Z06962 | VDAKYAKENLFAGWEITDLPNLTIQQRNAFIYKLWDDPSQSSELLSEAKKLNDSQAPK | SEQ ID NO:235 |
| Z06984 | VDAKYAKENIFAGWEIDDLPNLTTYQRNAFIYKLWDDPSQSSELLSEAKKLNDSQAPK | SEQ ID NO:236 |
| Z06986 | VDAKYAKENLFAGWEINDLPNLTEYQRNAFIYKLWDDPSQSSELLSEAKKLNDSQAPK | SEQ ID NO:237 |
| Z06999 | VDAKYAKEHLFAGWEITDLPNLTEQQRNAFIYKLWDDPSQSSELLSEAKKLNDSQAPK | SEQ ID NO:238 |
| Z07089 | VDAKYAKENIFAGWEITDLPNLTVQQRHAFIYKLWDDPSQSSELLSEAKKLNDSQAPK | SEQ ID NO:239 |
| Z07096 | VDAKYAKENIFAGWEIDELPNLTEYQRNAFIYKLWDDPSQSSELLSEAKKLNDSQAPK | SEQ ID NO:240 |
| Z06924 | VDAKYAKENIFAGWEITDLPNLTDDQRNAFIYKLWDDPSQSSELLSEAKKLNDSQAPK | SEQ ID NO:241 |
| Z06932 | VDAKYAKENIFAGWEISDLPNLTVAQRHAFIYKLWDDPSQSSELLSEAKKLNDSQAPK | SEQ ID NO:242 |
| Z06933 | VDAKYAKEDLFAGWEIDDLPNLTEYQRNAFIYKLWDDPSQSSELLSEAKKLNDSQAPK | SEQ ID NO:243 |
| Z06934 | VDAKYAKENIFAGWEIDDLPNLTESQRHAFIYKLWDDPSQSSELLSEAKKLNDSQAPK | SEQ ID NO:244 |
| Z06943 | VDAKYAKENLFAGWEITDLPNLTDYQRNAFIYKLWDDPSQSSELLSEAKKLNDSQAPK | SEQ ID NO:245 |
| Z06971 | VDAKYAKENLFAGWEISDLPNLTQQQRNAFIYKLWDDPSQSSELLSEAKKLNDSQAPK | SEQ ID NO:246 |
| Z06985 | VDAKYAKENIFAGWEIDDLPNLTDHQRNAFIYKLWDDPSQSSELLSEAKKLNDSQAPK | SEQ ID NO:247 |
| Z06993 | VDAKYAKENIFAGWEIRDLPNLTDYQRNAFIYKLWDDPSQSSELLSEAKKLNDSQAPK | SEQ ID NO:248 |
| Z07000 | VDAKYAKENWAAGWEISDLPNLTDFQRNAFIYKLWDDPSQSSELLSEAKKLNDSQAPK | SEQ ID NO:249 |
| Z07010 | VDAKYAKENIFAGWEIGDLPNLTEDQRNAFIYKLWDDPSQSSELLSEAKKLNDSQAPK | SEQ ID NO:250 |
| Z07012 | VDAKYAKENIFAGWEIDDLPNLTEAQRHAFIYKLWDDPSQSSELLSEAKKLNDSQAPK | SEQ ID NO:251 |
| Z07013 | VDAKYAKEQLFAGWEIDDLPNLTEFQRNAFIYKLWDDPSQSSELLSEAKKLNDSQAPK | SEQ ID NO:252 |
| Z07064 | VDAKYAKEWRYASIEIADLPNLTQRQRDAFIYKLWDDPSQSSELLSEAKKLNDSQAPK | SEQ ID NO:253 |
| Z07066 | VDAKYAKENWAAGWEIDDLPNLTIDQRNAFIYKLWDDPSQSSELLSEAKKLNDSQAPK | SEQ ID NO:254 |
| Z07072 | VDAKYAKEQLFAGWEIDDLPNLTDFQRNAFIYKLWDDPSQSSELLSEAKKLNDSQAPK | SEQ ID NO:255 |
| Z07074 | VDAKYAKENIFAGWEIELPNLTEFQRNAFIYKLWDDPSQSSELLSEAKKLNDSQAPK | SEQ ID NO:256 |
| Z07077 | VDAKYAKENIFAGWEIGDLPNLTEDQRNAFIYKLWDDPSQSSELLSEAKKLNDSQAPK | SEQ ID NO:257 |
| Z07081 | VDAKYAKEHIFAGWEIEDLPNLTEDQRNAFIYKLWDDPSQSSELLSEAKKLNDSQAPK | SEQ ID NO:258 |
| Z07082 | VDAKYAKEHISDLPNLTEQQRHAFIYKLWDDPSQSSELLSEAKKLNDSQAPK | SEQ ID NO:259 |
| Z07090 | VDAKYAKENLFAGWEIDDLPNLTVQQRNAFIYKLWDDPSQSSELLSEAKKLNDSQAPK | SEQ ID NO:260 |

Figure 1J

| ID | Sequence | SEQ ID NO |
|---|---|---|
| Z07100 | VDAKYAKEHLFAGWEIDDLPNLTDHQRNAFIYKLWDDPSQSSELLSEAKKLNDSQAPK | SEQ ID NO:261 |
| Z07104 | VDAKYAKENIFAGWEISDLPNLTIDQRNAFIYKLWDDPSQSSELLSEAKKLNDSQAPK | SEQ ID NO:262 |
| Z07112 | VDAKYAKENIWAGWEIDDLPNLTERQRNAFIYKLWDDPSQSSELLSEAKKLNDSQAPK | SEQ ID NO:263 |
| Z06954 | VDAKYAKENIFAGWEIEDLPNLTDGQRNAFIYKLWDDPSQSSELLSEAKKLNDSQAPK | SEQ ID NO:264 |
| Z06960 | VDAKYAKENIFAGWEISDLPNLTEHQRNAFIYKLWDDPSQSSELLSEAKKLNDSQAPK | SEQ ID NO:265 |
| Z06977 | VDAKYAKENIFAGWEIEDLPNLTDHQRDAFIYKLWDDPSQSSELLSEAKKLNDSQAPK | SEQ ID NO:266 |
| Z07095 | VDAKYAKEHWAAGWEIDDLPNLTEFQRNAFIYKLWDDPSQSSELLSEAKKLNDSQAPK | SEQ ID NO:267 |
| Z06920 | VDAKYAKEHLFAGWEITDLPNLTDQQRDAFIYKLWDDPSQSSELLSEAKKLNDSQAPK | SEQ ID NO:268 |
| Z06922 | VDAKYAKEQLFAGWEIDDLPNLTEAQRNAFIYKLWDDPSQSSELLSEAKKLNDSQAPK | SEQ ID NO:269 |
| Z06923 | VDAKYAKEQLFAGWEISDLPNLTEQQRHAFIYKLWDDPSQSSELLSEAKKLNDSQAPK | SEQ ID NO:270 |
| Z06925 | VDAKYAKENLFAGWEIDDLPNLTWQQRNAFIYKLWDDPSQSSELLSEAKKLNDSQAPK | SEQ ID NO:271 |
| Z06927 | VDAKYAKENIFAGWEIQDLPNLTIEQRNAFIYKLWDDPSQSSELLSEAKKLNDSQAPK | SEQ ID NO:272 |
| Z06928 | VDAKYAKENIFAGWEITELPNLTEQQRDAFIYKLWDDPSQSSELLSEAKKLNDSQAPK | SEQ ID NO:273 |
| Z06929 | VDAKYAKEWWAAGEITELPNLIQDLPNLTIQQRDAFIYKLWDDPSQSSELLSEAKKLNDSQAPK | SEQ ID NO:274 |
| Z06930 | VDAKYAKENWAAGWEITDLPNLTSSQRNAFIYKLWDDPSQSSELLSEAKKLNDSQAPK | SEQ ID NO:275 |
| Z06931 | VDAKYAKEHLFAGWEITDLPNLTIDQRNAFIYKLWDDPSQSSELLSEAKKLNDSQAPK | SEQ ID NO:276 |
| Z06935 | VDAKYAKEWRWASIEIADLPNLTQHQRDAFIYKLWDDPSQSSELLSEAKKLNDSQAPK | SEQ ID NO:277 |
| Z06937 | VDAKYAKEWNYAAGEISSLPNLTEQQRDAFIYKLWDDPSQSSELLSEAKKLNDSQAPK | SEQ ID NO:278 |
| Z06938 | VDAKYAKEWWWAAGEISSLPNLTACQRDAFIYKLWDDPSQSSELLSEAKKLNDSQAPK | SEQ ID NO:279 |
| Z06939 | VDAKYAKEHIFAGWEISDLPNLTIYQRHAFIYKLWDDPSQSSELLSEAKKLNDSQAPK | SEQ ID NO:280 |
| Z06941 | VDAKYAKENIFAGWEIDDLPNLTDNQRHAFIYKLWDDPSQSSELLSEAKKLNDSQAPK | SEQ ID NO:281 |
| Z06944 | VDAKYAKEWQWAGVEIAELPNLTQQRDAFIYKLWDDPSQSSELLSEAKKLNDSQAPK | SEQ ID NO:282 |
| Z06948 | VDAKYAKEHIFAGWEITDLPNLTSSQRNAFIYKLWDDPSQSSELLSEAKKLNDSQAPK | SEQ ID NO:283 |
| Z06949 | VDAKYAKEWRWAGVEIQDLPNLTQQRDAFIYKLWDDPSQSSELLSEAKKLNDSQAPK | SEQ ID NO:284 |
| Z06951 | VDAKYAKEWWAAGWEIQDLPNLTIFQRHAFIYKLWDDPSQSSELLSEAKKLNDSQAPK | SEQ ID NO:285 |
| Z06955 | VDAKYAKEWQWAGVEIQELPNLTCQQRHAFIYKLWDDPSQSSELLSEAKKLNDSQAPK | SEQ ID NO:286 |
| Z06956 | VDAKYAKEHIFAGWEIDDLPNLTDNQRHAFIYKLWDDPSQSSELLSEAKKLNDSQAPK | SEQ ID NO:287 |
| Z06964 | VDAKYAKENLFAGWEIDDLPNLTIRQQRHAFIYKLWDDPSQSSELLSEAKKLNDSQAPK | SEQ ID NO:288 |
| Z06967 | VDAKYAKENLFAGWEIADLPNLTDHQRNAFIYKLWDDPSQSSELLSEAKKLNDSQAPK | SEQ ID NO:289 |

Figure 1K

| | | |
|---|---|---|
| Z06970 | VDAKYAKEWSWASVEIADLPNLTQRQRDAFIYKLWDDPSQSSELLSEAKKLNDSQAPK | SEQ ID NO:290 |
| Z06987 | VDAKYAKEDIFAGWEITDLPNLTDHQRNAFIYKLWDDPSQSSELLSEAKKLNDSQAPK | SEQ ID NO:291 |
| Z06988 | VDAKYAKEQLFAGWEIDDLPNLTIDQRNAFIYKLWDDPSQSSELLSEAKKLNDSQAPK | SEQ ID NO:292 |
| Z06990 | VDAKYAKENWFAGWEIDDLPNLTERQRNAFIYKLWDDPSQSSELLSEAKKLNDSQAPK | SEQ ID NO:293 |
| Z06994 | VDAKYAKEHLFAGWEIDELPNLTEQRRNAFIYKLWDDPSQSSELLSEAKKLNDSQAPK | SEQ ID NO:294 |
| Z06995 | VDAKYAKENFWAGWEIDDLPNLTELQRNAFIYKLWDDPSQSSELLSEAKKLNDSQAPK | SEQ ID NO:295 |
| Z06996 | VDAKYAKEHLFAGWEIEDLPNLTIDQRNAFIYKLWDDPSQSSELLSEAKKLNDSQAPK | SEQ ID NO:296 |
| Z06997 | VDAKYAKENVFAGWEIDDLPNLTDQQRNAFIYKLWDDPSQSSELLSEAKKLNDSQAPK | SEQ ID NO:297 |
| Z07005 | VDAKYAKEHIFAGWEIADLPNLTDGQRNAFIYKLWDDPSQSSELLSEAKKLNDSQAPK | SEQ ID NO:298 |
| Z07006 | VDAKYAKENIWAGWEISDLPNLTDTQRNAFIYKLWDDPSQSSELLSEAKKLNDSQAPK | SEQ ID NO:299 |
| Z07007 | VDAKYAKEWQWAGIEIQDLPNLTQRQRDAFIYKLWDDPSQSSELLSEAKKLNDSQAPK | SEQ ID NO:300 |
| Z07011 | VDAKYAKEWIFAGWEITDLPNLTDFQRNAFIYKLWDDPSQSSELLSEAKKLNDSQAPK | SEQ ID NO:301 |
| Z07015 | VDAKYAKENWAAGWEIDDLPNLTDQQRDAFIYKLWDDPSQSSELLSEAKKLNDSQAPK | SEQ ID NO:302 |
| Z07020 | VDAKYAKEHLFAGWEIDELPNLTAYQRNAFIYKLWDDPSQSSELLSEAKKLNDSQAPK | SEQ ID NO:303 |
| Z07022 | VDAKYAKEHIFAGWEIEDLPNLTESQRNAFIYKLWDDPSQSSELLSEAKKLNDSQAPK | SEQ ID NO:304 |
| Z07024 | VDAKYAKENIFAGWEIDDLPNLTAHQRDAFIYKLWDDPSQSSELLSEAKKLNDSQAPK | SEQ ID NO:305 |
| Z07025 | VDAKYAKEWIFAGWEIDDLPNLTTQQHAFIYKLWDDPSQSSELLSEAKKLNDSQAPK | SEQ ID NO:306 |
| Z07027 | VDAKYAKENLFAGWEIGDLPNLTANQRDAFIYKLWDDPSQSSELLSEAKKLNDSQAPK | SEQ ID NO:307 |
| Z07028 | VDAKYAKEQLFAGWEIDDLPNLTDQQRHAFIYKLWDDPSQSSELLSEAKKLNDSQAPK | SEQ ID NO:308 |
| Z07030 | VDAKYAKEWQWAGVEINDLPNLTQRQRDAFIYKLWDDPSQSSELLSEAKKLNDSQAPK | SEQ ID NO:309 |
| Z07034 | VDAKYAKEWWYAGVEIADLPNLTQQCRDAFIYKLWDDPSQSSELLSEAKKLNDSQAPK | SEQ ID NO:310 |
| Z07036 | VDAKYAKEQWWAGWEIDDLPNLTEIQRNAFIYKLWDDPSQSSELLSEAKKLNDSQAPK | SEQ ID NO:311 |
| Z07037 | VDAKYAKEWQWAGVEINELPNLTQRQRDAFIYKLWDDPSQSSELLSEAKKLNDSQAPK | SEQ ID NO:312 |
| Z07038 | VDAKYAKENIWAGWEISDLPNLTEDQRNAFIYKLWDDPSQSSELLSEAKKLNDSQAPK | SEQ ID NO:313 |
| Z07045 | VDAKYAKEHIFAGWEIEELPNLTDTQRNAFIYKLWDDPSQSSELLSEAKKLNDSQAPK | SEQ ID NO:314 |
| Z07049 | VDAKYAKEDIWAGWEITDLPNLTEWQRHAFIYKLWDDPSQSSELLSEAKKLNDSQAPK | SEQ ID NO:315 |
| Z07052 | VDAKYAKEHIFAGWEIEDLPNLTDNQRDAFIYKLWDDPSQSSELLSEAKKLNDSQAPK | SEQ ID NO:316 |
| Z07053 | VDAKYAKENLWAGWEINDLPNLTEQQRNAFIYKLWDDPSQSSELLSEAKKLNDSQAPK | SEQ ID NO:317 |
| Z07056 | VDAKYAKENIWAGWEIDDLPNLTVNQRDAFIYKLWDDPSQSSELLSEAKKLNDSQAPK | SEQ ID NO:318 |

Figure 1L

| | | |
|---|---|---|
| Z07061 | VDAKYAKEQWWAGWEIDDLPNLTEDQRNAFIYKLMDDPSQSSELLSEAKKLNDSQAPK | SEQ ID NO:319 |
| Z07063 | VDAKYAKEHTNAWAEIHRLPNLTESQQNAFIYKLMDDPSQSSELLSEAKKLNDSQAPK | SEQ ID NO:320 |
| Z07070 | VDAKYAKEWWYAGEIADLPNLTQQQQDAFIYKLMDDPSQSSELLSEAKKLNDSQAPK | SEQ ID NO:321 |
| Z07083 | VDAKYAKEWQWAGVEINELPNLTWQQRQAFIYKLMDDPSQSSELLSEAKKLNDSQAPK | SEQ ID NO:322 |
| Z07085 | VDAKYAKEWQWAGVEINDLPNLTQQQRDAFIYKLMDDPSQSSELLSEAKKLNDSQAPK | SEQ ID NO:323 |
| Z07086 | VDAKYAKEWRWAGVEIAELPNLTQNQRDAFIYKLMDDPSQSSELLSEAKKLNDSQAPK | SEQ ID NO:324 |
| Z07087 | VDAKYAKEHLFAGWEIGDLPNLTEQQRHAFIYKLMDDPSQSSELLSEAKKLNDSQAPK | SEQ ID NO:325 |
| Z07088 | VDAKYAKENLFAGWEIHDLPNLTDDQRNAFIYKLMDDPSQSSELLSEAKKLNDSQAPK | SEQ ID NO:326 |
| Z07092 | VDAKYAKENLFAGWEIDDLPNLTEVQRNAFIYKLMDDPSQSSELLSEAKKLNDSQAPK | SEQ ID NO:327 |
| Z07093 | VDAKYAKENLFAGWEIDLPNLTGQQRDAFIYKLMDDPSQSSELLSEAKKLNDSQAPK | SEQ ID NO:328 |
| Z07094 | VDAKYAKEWWWAAGEISDLPNLTGQQRDAFIYKLMDDPSQSSELLSEAKKLNDSQAPK | SEQ ID NO:329 |
| Z07097 | VDAKYAKENIFAGWEIVDLPNLTEIQRNAFIYKLMDDPSQSSELLSEAKKLNDSQAPK | SEQ ID NO:330 |
| Z07098 | VDAKYAKENLFAGWEIRDLPNLTEAQRHAFIYKLMDDPSQSSELLSEAKKLNDSQAPK | SEQ ID NO:331 |
| Z07101 | VDAKYAKENIWAGWEITDLPNLTEHQRHAFIYKLMDDPSQSSELLSEAKKLNDSQAPK | SEQ ID NO:332 |
| Z07103 | VDAKYAKEHLFAGWEICDLPNLTQPNLTEDQRNAFIYKLMDDPSQSSELLSEAKKLNDSQAPK | SEQ ID NO:333 |
| Z07105 | VDAKYAKENIWAGWEIGDLPNLTEQQRDAFIYKLMDDPSQSSELLSEAKKLNDSQAPK | SEQ ID NO:334 |
| Z07110 | VDAKYAKEWQWAGVEIQDLPNLTGQQRDAFIYKLMDDPSQSSELLSEAKKLNDSQAPK | SEQ ID NO:335 |
| Z07113 | VDAKYAKEQIFAGWEITDLPNLTEAQRNAFIYKLMDDPSQSSELLSEAKKLNDSQAPK | SEQ ID NO:336 |
| Z07115 | VDAKYAKENIWAGWEIGDLPNLTDQQRNAFIYKLMDDPSQSSELLSEAKKLNDSQAPK | SEQ ID NO:337 |
| Z07117 | VDAKYAKEWSNASVEIADLPNLTQQQRDAFIYKLMDDPSQSSELLSEAKKLNDSQAPK | SEQ ID NO:338 |
| Z07119 | VDAKYAKENIFAGWEIEDLPNLTVHQRDAFIYKLMDDPSQSSELLSEAKKLNDSQAPK | SEQ ID NO:339 |
| | ENLWAGWEIDDLPNLTHSQRNAFIYKLWD | SEQ ID NO:340 |
| | EDVNAWQEIIKLPNLTFQRDAFIYKLWD | SEQ ID NO:341 |
| | EWKFASIEIADLPNLTQHQKDAFIFKLWD | SEQ ID NO:342 |
| | EHEWAGVEIQSLPNLTQQKHAFIYKLWD | SEQ ID NO:343 |
| | EDRYAWTEIHKLPNLTVRQQNAFIYKLWD | SEQ ID NO:344 |
| | KENLWAGWEIDDLPNLTHSQRNAFIYKLMDDPSQSSELLAEAKKLNDAQ | SEQ ID NO:345 |
| | KEDVNAWQEIIKLPNLTIFQRDAFIYKLMDDPSQSSELLAEAKKLNDAQ | SEQ ID NO:346 |
| | KEWKFASIEIADLPNLTQHQKDAFIFKLMDDPSQSSELLAEAKKLNDAQ | SEQ ID NO:347 |

Figure 1M

| | | |
|---|---|---|
| | KEHEWAGVEIQSLPNLTTQQKHAFIYKLWDDPSQSSELLAEAKKLNDAQ | SEQ ID NO:348 |
| | KEDRYAWTEIHKLPNLTVRQQNAFIYKLWDDPSQSSELLAEAKKLNDAQ | SEQ ID NO:349 |
| Z04187 | VDAKYAKENLWAGWEIDDLPNLTHSQRNAFIYKLWDDPSQSSELLAEAKKLNDAQAPK | SEQ ID NO:350 |
| Z04191 | VDAKYAKEDVNAWQEIIKLPNLTIFQRDAFIYKLWDDPSQSSELLAEAKKLNDAQAPK | SEQ ID NO:351 |
| Z04196 | VDAKYAKEWKFASIEIADLPNLTQHQKDAFIFKLWDDPSQSSELLAEAKKLNDAQAPK | SEQ ID NO:352 |
| Z04208 | VDAKYAKEHEWAGVEIQSLPNLTTQQKHAFIYKLWDDPSQSSELLAEAKKLNDAQAPK | SEQ ID NO:353 |
| Z04421 | VDAKYAKEDRYAWTEIHKLPNLTVRQQNAFIYKLWDDPSQSSELLAEAKKLNDAQAPK | SEQ ID NO:354 |
| Z03639 | VDNKFNKELGWATWEIFNLPNLNGVQVKAFIDSLRDDPSQSANLLAEAKKLNDAQAPK | SEQ ID NO:355 |
| Z03638 | AEAKYAKELGWATWEIFNLPNLTGVQVKAFIDKLRDDPSQSELLSEAKKLNDSQAPK | SEQ ID NO:356 |
| Z01155 | VDNKFNKELGWATWEIFNLPNLNGVQVKAFIDSLRDDPSQSANLLAEAKKLNDAQAPK | SEQ ID NO:357 |
| Z08693 | VDAKYAKEWKFASIEIADLPNLTQHQKDAFIFKLWDDPSQSSELLAEAKKLNDSQAPK | SEQ ID NO:358 |
| Z01157 | VDNKFNKERVIAIGEIMRLPNLNSLQVVAFINSLRDDPSQSANLLAEAKKLNDAQAPK | SEQ ID NO:359 |
| CAIX | PLGEEDLPSEEDSPREEDPGEEDLPGEEDLPEVKPKSEEEGSLKEDLPTVEAPGDPQEPQ<br>NNAHRDKEGDDQSHWRYGGDPPWPRVSPACAGRFQSPVDIRPQLAAFCPALRPLELLGFQLPPLPELR<br>LRNNGHSVQLTLPPGLEMALGPGREYRALQLHLHWGAAGRPGSEHTVEGHRFPAEIHVVHLSTAFARV<br>DEALGRPGGLAVLAAFLEEGPEENSAYEQLLSRLEEIAEEGSETQVPGLDISALLPSDFSRYFQYEGS<br>LTTPPCAQGVIWTVFNQTVMLSAKQLHTLSDTLWGPGDSRLQLNFRATQPLNGRVIEASFPAGVDSSP<br>RAAEPVQLNSCLAAGD | |
| | AEAKYAKENLFAGWEIDDLPNLTEDQRNAFIYKLWDDPSQSSELLSEAKKLNDSQAPK | SEQ ID NO:360 |
| Z09781 | AEAKYAKENLFAGWEIDDLPNLTEDQRNAFIYKLWDDPSQSSELLSEAKKLNDSQAPK | SEQ ID NO:365 |
| Z09782 | AEAKYAKENLFAGWEISDLPNLTDYQRNAFIYKLWDDPSQSSELLSEAKKLNDSQAPK | SEQ ID NO:366 |
| Z09783 | AEAKYAKENIFAGWEIDDLPNLTDEQRNAFIYKLWDDPSQSSELLSEAKKLNDSQAPK | SEQ ID NO:367 |
| Z09784 | AEAKYAKEWWWAGIEIADLPNLTQQQRDAFIYKLWDDPSQSSELLSEAKKLNDSQAPK | SEQ ID NO:368 |

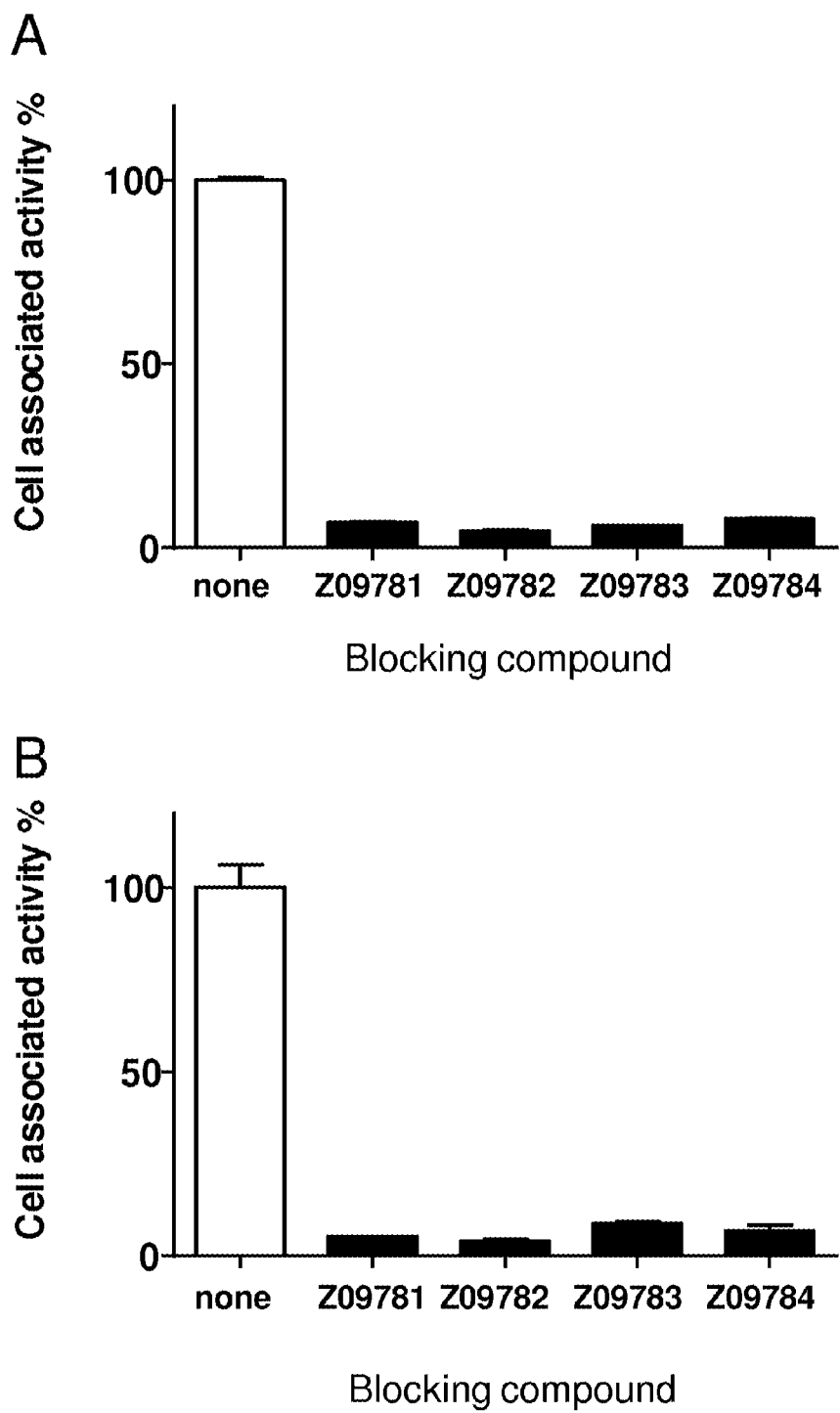
Figure 6A-B

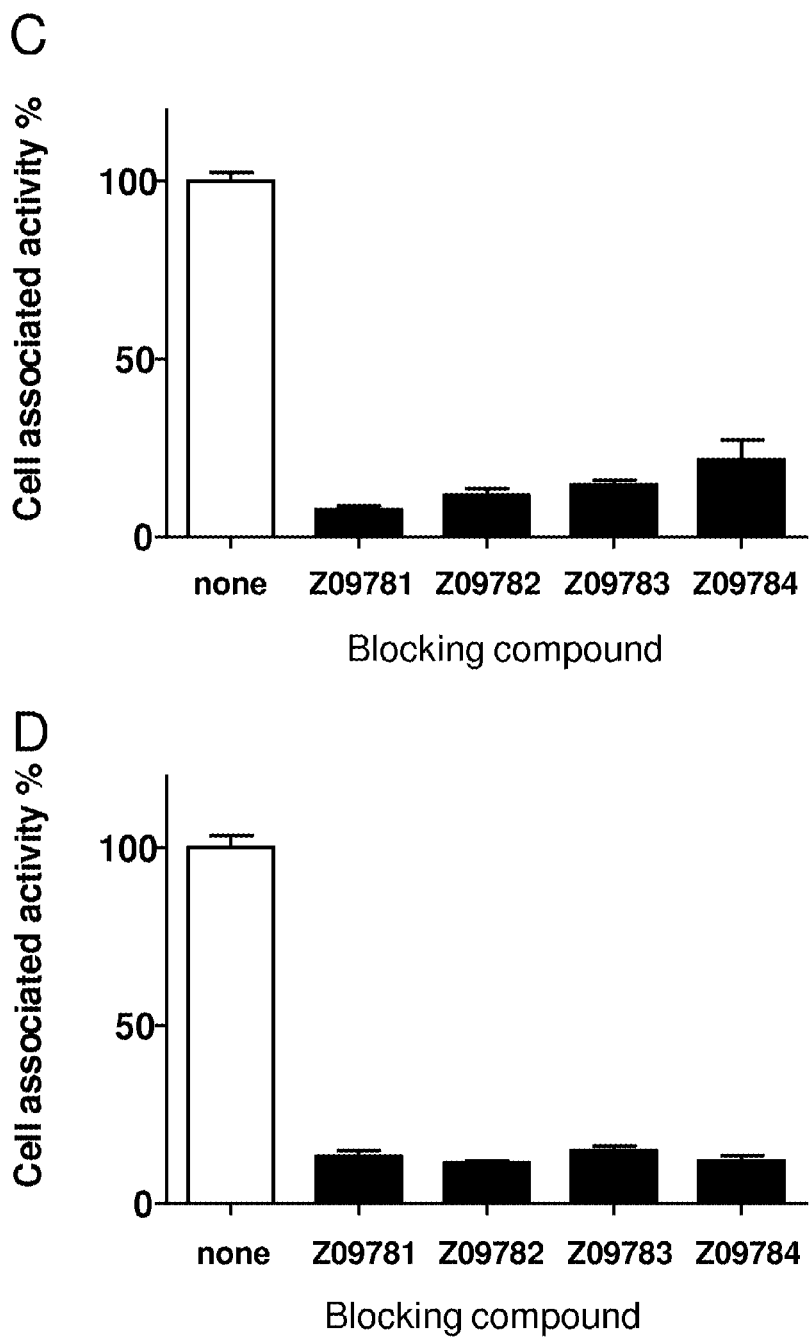
Figure 6C-D

SEQUENCE LISTING

<160> NUMBER OF SEQ ID NOS: 390

<210> SEQ ID NO 1
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 1

Glu Asn Leu Phe Ala Gly Trp Glu Ile Asp Asp Leu Pro Asn Leu Thr
1               5                   10                  15

Glu Asp Gln Arg Asn Ala Phe Ile Tyr Lys Leu Trp Asp
            20                  25

<210> SEQ ID NO 2
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 2

Glu Asn Leu Phe Ala Gly Trp Glu Ile Ser Asp Leu Pro Asn Leu Thr
1               5                   10                  15

Asp Tyr Gln Arg Asn Ala Phe Ile Tyr Lys Leu Trp Asp
            20                  25

<210> SEQ ID NO 3
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 3

Glu Asn Ile Phe Ala Gly Trp Glu Ile Asp Asp Leu Pro Asn Leu Thr
1               5                   10                  15

Asp Glu Gln Arg Asn Ala Phe Ile Tyr Lys Leu Trp Asp
            20                  25

<210> SEQ ID NO 4
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 4

Glu Asn Leu Phe Ala Gly Trp Glu Ile Asp Asp Leu Pro Asn Leu Thr
1               5                   10                  15

Glu Ser Gln Arg Asn Ala Phe Ile Tyr Lys Leu Trp Asp
            20                  25

<210> SEQ ID NO 5
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 5

Glu Trp Trp Trp Ala Gly Ile Glu Ile Ala Asp Leu Pro Asn Leu Thr
1               5                   10                  15

Gln Gln Gln Arg Asp Ala Phe Ile Tyr Lys Leu Trp Asp
            20                  25

<210> SEQ ID NO 6
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 6

Glu His Leu Phe Ala Gly Trp Glu Ile Glu Asp Leu Pro Asn Leu Thr
1               5                   10                  15

Glu Tyr Gln Arg Asn Ala Phe Ile Tyr Lys Leu Trp Asp
            20                  25

<210> SEQ ID NO 7
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 7

Glu Asn Leu Phe Ala Gly Trp Glu Ile Thr Asp Leu Pro Asn Leu Thr
1               5                   10                  15

Ile Glu Gln Arg Asn Ala Phe Ile Tyr Lys Leu Trp Asp
            20                  25

<210> SEQ ID NO 8
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 8

Glu Asn Leu Phe Ala Gly Trp Glu Ile Gly Asp Leu Pro Asn Leu Thr
1               5                   10                  15

Glu Gln Gln Arg His Ala Phe Ile Tyr Lys Leu Trp Asp
            20                  25

<210> SEQ ID NO 9
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 9

Glu Asn Leu Phe Ala Gly Trp Glu Ile Thr Asp Leu Pro Asn Leu Thr
1               5                   10                  15

Ile Gln Gln Arg Asn Ala Phe Ile Tyr Lys Leu Trp Asp
            20                  25

<210> SEQ ID NO 10
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 10

Glu Asn Ile Phe Ala Gly Trp Glu Ile Asp Asp Leu Pro Asn Leu Thr
1               5                   10                  15

```
Thr Tyr Gln Arg Asn Ala Phe Ile Tyr Lys Leu Trp Asp
            20                  25
```

<210> SEQ ID NO 11
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 11

```
Glu Asn Leu Phe Ala Gly Trp Glu Ile Asn Asp Leu Pro Asn Leu Thr
1               5                   10                  15

Glu Tyr Gln Arg Asn Ala Phe Ile Tyr Lys Leu Trp Asp
            20                  25
```

<210> SEQ ID NO 12
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 12

```
Glu His Leu Phe Ala Gly Trp Glu Ile Thr Asp Leu Pro Asn Leu Thr
1               5                   10                  15

Glu Gln Gln Arg Asn Ala Phe Ile Tyr Lys Leu Trp Asp
            20                  25
```

<210> SEQ ID NO 13
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 13

```
Glu Asn Ile Phe Ala Gly Trp Glu Ile Thr Asp Leu Pro Asn Leu Thr
1               5                   10                  15

Val Gln Gln Arg His Ala Phe Ile Tyr Lys Leu Trp Asp
            20                  25
```

<210> SEQ ID NO 14
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 14

```
Glu Asn Ile Phe Ala Gly Trp Glu Ile Asp Glu Leu Pro Asn Leu Thr
1               5                   10                  15

Glu Tyr Gln Arg Asn Ala Phe Ile Tyr Lys Leu Trp Asp
            20                  25
```

<210> SEQ ID NO 15
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 15

```
Glu His Ile Phe Ala Gly Trp Glu Ile Thr Asp Leu Pro Asn Leu Thr
```

```
1               5                   10                  15
Asp Asp Gln Arg Asn Ala Phe Ile Tyr Lys Leu Trp Asp
            20                  25

<210> SEQ ID NO 16
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 16

Glu Asn Ile Phe Ala Gly Trp Glu Ile Ser Asp Leu Pro Asn Leu Thr
1               5                   10                  15
Val Ala Gln Arg His Ala Phe Ile Tyr Lys Leu Trp Asp
            20                  25

<210> SEQ ID NO 17
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 17

Glu Asp Leu Phe Ala Gly Trp Glu Ile Asp Asp Leu Pro Asn Leu Thr
1               5                   10                  15
Glu Tyr Gln Arg Asn Ala Phe Ile Tyr Lys Leu Trp Asp
            20                  25

<210> SEQ ID NO 18
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 18

Glu Asn Ile Phe Ala Gly Trp Glu Ile Asp Asp Leu Pro Asn Leu Thr
1               5                   10                  15
Glu Ser Gln Arg His Ala Phe Ile Tyr Lys Leu Trp Asp
            20                  25

<210> SEQ ID NO 19
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 19

Glu Asn Leu Phe Ala Gly Trp Glu Ile Thr Asp Leu Pro Asn Leu Thr
1               5                   10                  15
Asp Tyr Gln Arg His Ala Phe Ile Tyr Lys Leu Trp Asp
            20                  25

<210> SEQ ID NO 20
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 20
```

```
Glu Asn Leu Phe Ala Gly Trp Glu Ile Ser Asp Leu Pro Asn Leu Thr
1               5                   10                  15

Gln Gln Gln Arg His Ala Phe Ile Tyr Lys Leu Trp Asp
            20                  25
```

<210> SEQ ID NO 21
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 21

```
Glu Asn Ile Phe Ala Gly Trp Glu Ile Glu Asp Leu Pro Asn Leu Thr
1               5                   10                  15

Asp His Gln Arg Asn Ala Phe Ile Tyr Lys Leu Trp Asp
            20                  25
```

<210> SEQ ID NO 22
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 22

```
Glu Asn Ile Phe Ala Gly Trp Glu Ile Arg Asp Leu Pro Asn Leu Thr
1               5                   10                  15

Asp Tyr Gln Arg Asn Ala Phe Ile Tyr Lys Leu Trp Asp
            20                  25
```

<210> SEQ ID NO 23
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 23

```
Glu Asn Trp Ala Ala Gly Trp Glu Ile Ser Asp Leu Pro Asn Leu Thr
1               5                   10                  15

Asp Phe Gln Arg Asn Ala Phe Ile Tyr Lys Leu Trp Asp
            20                  25
```

<210> SEQ ID NO 24
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 24

```
Glu Asn Ile Phe Ala Gly Trp Glu Ile Gly Asp Leu Pro Asn Leu Thr
1               5                   10                  15

Glu Asp Gln Arg Asn Ala Phe Ile Tyr Lys Leu Trp Asp
            20                  25
```

<210> SEQ ID NO 25
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 25

Glu Asn Ile Phe Ala Gly Trp Glu Ile Asp Asp Leu Pro Asn Leu Thr
1               5                   10                  15

Glu Ala Gln Arg His Ala Phe Ile Tyr Lys Leu Trp Asp
            20                  25

<210> SEQ ID NO 26
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 26

Glu Gln Leu Phe Ala Gly Trp Glu Ile Asp Asp Leu Pro Asn Leu Thr
1               5                   10                  15

Glu Phe Gln Arg Asn Ala Phe Ile Tyr Lys Leu Trp Asp
            20                  25

<210> SEQ ID NO 27
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 27

Glu Trp Arg Tyr Ala Ser Ile Glu Ile Ala Asp Leu Pro Asn Leu Thr
1               5                   10                  15

Gln Arg Gln Arg Asp Ala Phe Ile Tyr Lys Leu Trp Asp
            20                  25

<210> SEQ ID NO 28
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 28

Glu Asn Trp Ala Ala Gly Trp Glu Ile Asp Asp Leu Pro Asn Leu Thr
1               5                   10                  15

Ile Asp Gln Arg Asn Ala Phe Ile Tyr Lys Leu Trp Asp
            20                  25

<210> SEQ ID NO 29
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 29

Glu Gln Leu Phe Ala Gly Trp Glu Ile Asp Asp Leu Pro Asn Leu Thr
1               5                   10                  15

Asp Phe Gln Arg Asn Ala Phe Ile Tyr Lys Leu Trp Asp
            20                  25

<210> SEQ ID NO 30
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

```
<400> SEQUENCE: 30

Glu Asn Ile Phe Ala Gly Trp Glu Ile Glu Glu Leu Pro Asn Leu Thr
1               5                   10                  15

Glu Phe Gln Arg Asn Ala Phe Ile Tyr Lys Leu Trp Asp
            20                  25

<210> SEQ ID NO 31
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 31

Glu Asn Leu Phe Ala Gly Trp Glu Ile Gly Asp Leu Pro Asn Leu Thr
1               5                   10                  15

Glu Asp Gln Arg Asn Ala Phe Ile Tyr Lys Leu Trp Asp
            20                  25

<210> SEQ ID NO 32
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 32

Glu Asn Ile Phe Ala Gly Trp Glu Ile Glu Asp Leu Pro Asn Leu Thr
1               5                   10                  15

Asp Gln Gln Arg Asn Ala Phe Ile Tyr Lys Leu Trp Asp
            20                  25

<210> SEQ ID NO 33
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 33

Glu His Ile Phe Ala Gly Trp Glu Ile Ser Asp Leu Pro Asn Leu Thr
1               5                   10                  15

Glu Gln Gln Arg His Ala Phe Ile Tyr Lys Leu Trp Asp
            20                  25

<210> SEQ ID NO 34
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 34

Glu Asn Leu Phe Ala Gly Trp Glu Ile Asp Asp Leu Pro Asn Leu Thr
1               5                   10                  15

Val Gln Gln Arg Asn Ala Phe Ile Tyr Lys Leu Trp Asp
            20                  25

<210> SEQ ID NO 35
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide
```

-continued

```
<400> SEQUENCE: 35

Glu His Leu Phe Ala Gly Trp Glu Ile Asp Asp Leu Pro Asn Leu Thr
1               5                   10                  15

Asp His Gln Arg Asn Ala Phe Ile Tyr Lys Leu Trp Asp
            20                  25

<210> SEQ ID NO 36
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 36

Glu Asn Ile Phe Ala Gly Trp Glu Ile Ser Asp Leu Pro Asn Leu Thr
1               5                   10                  15

Ile Asp Gln Arg Asn Ala Phe Ile Tyr Lys Leu Trp Asp
            20                  25

<210> SEQ ID NO 37
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 37

Glu Asn Ile Trp Ala Gly Trp Glu Ile Asp Asp Leu Pro Asn Leu Thr
1               5                   10                  15

Glu Arg Gln Arg Asn Ala Phe Ile Tyr Lys Leu Trp Asp
            20                  25

<210> SEQ ID NO 38
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 38

Glu Asn Ile Phe Ala Gly Trp Glu Ile Glu Asp Leu Pro Asn Leu Thr
1               5                   10                  15

Asp Gly Gln Arg Asn Ala Phe Ile Tyr Lys Leu Trp Asp
            20                  25

<210> SEQ ID NO 39
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 39

Glu Asn Ile Phe Ala Gly Trp Glu Ile Ser Asp Leu Pro Asn Leu Thr
1               5                   10                  15

Glu His Gln Arg Asn Ala Phe Ile Tyr Lys Leu Trp Asp
            20                  25

<210> SEQ ID NO 40
<211> LENGTH: 29
<212> TYPE: PRT
<213> ORGANISM: ARTIFICIAL SEQUENCE
<220> FEATURE:
```

<223> OTHER INFORMATION: Engineered CAIX-binding polypeptide

<400> SEQUENCE: 40

Glu Asn Ile Phe Ala Gly Trp Glu Ile Glu Asp Leu Pro Asn Leu Thr
1               5                   10                  15

Asp His Gln Arg Asp Ala Phe Ile Tyr Lys Leu Trp Asp
            20                  25

<210> SEQ ID NO 41
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 41

Glu His Trp Ala Ala Gly Trp Glu Ile Asp Asp Leu Pro Asn Leu Thr
1               5                   10                  15

Glu Phe Gln Arg Asn Ala Phe Ile Tyr Lys Leu Trp Asp
            20                  25

<210> SEQ ID NO 42
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 42

Glu His Leu Phe Ala Gly Trp Glu Ile Thr Asp Leu Pro Asn Leu Thr
1               5                   10                  15

Asp Gln Gln Arg Asp Ala Phe Ile Tyr Lys Leu Trp Asp
            20                  25

<210> SEQ ID NO 43
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 43

Glu Gln Leu Phe Ala Gly Trp Glu Ile Asp Asp Leu Pro Asn Leu Thr
1               5                   10                  15

Glu Ala Gln Arg Asn Ala Phe Ile Tyr Lys Leu Trp Asp
            20                  25

<210> SEQ ID NO 44
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 44

Glu Gln Leu Phe Ala Gly Trp Glu Ile Ser Asp Leu Pro Asn Leu Thr
1               5                   10                  15

Glu Gln Gln Arg His Ala Phe Ile Tyr Lys Leu Trp Asp
            20                  25

<210> SEQ ID NO 45
<211> LENGTH: 29
<212> TYPE: PRT
<213> ORGANISM: ARTIFICIAL SEQUENCE

```
<220> FEATURE:
<223> OTHER INFORMATION: Engineered CAIX-binding polypeptide

<400> SEQUENCE: 45

Glu Asn Leu Phe Ala Gly Trp Glu Ile Asp Asp Leu Pro Asn Leu Thr
1               5                   10                  15
Trp Gln Gln Arg His Ala Phe Ile Tyr Lys Leu Trp Asp
            20                  25

<210> SEQ ID NO 46
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 46

Glu Asn Ile Phe Ala Gly Trp Glu Ile Gln Asp Leu Pro Asn Leu Thr
1               5                   10                  15
Ile Glu Gln Arg Asn Ala Phe Ile Tyr Lys Leu Trp Asp
            20                  25

<210> SEQ ID NO 47
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 47

Glu Trp Trp Trp Ala Ala Gly Glu Ile Thr Glu Leu Pro Asn Leu Thr
1               5                   10                  15
Glu Gln Gln Arg Asp Ala Phe Ile Tyr Lys Leu Trp Asp
            20                  25

<210> SEQ ID NO 48
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 48

Glu Trp Gln Trp Ala Gly Val Glu Ile Gln Asp Leu Pro Asn Leu Thr
1               5                   10                  15
Asp Asn Gln Arg Gln Ala Phe Ile Tyr Lys Leu Trp Asp
            20                  25

<210> SEQ ID NO 49
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 49

Glu Asn Trp Ala Ala Gly Trp Glu Ile Thr Asp Leu Pro Asn Leu Thr
1               5                   10                  15
Ser Ser Gln Arg Asn Ala Phe Ile Tyr Lys Leu Trp Asp
            20                  25

<210> SEQ ID NO 50
<211> LENGTH: 29
<212> TYPE: PRT
```

```
<213> ORGANISM: ARTIFICIAL SEQUENCE
<220> FEATURE:
<223> OTHER INFORMATION: Engineered CAIX-binding polypeptide

<400> SEQUENCE: 50

Glu His Leu Phe Ala Gly Trp Glu Ile Thr Asp Leu Pro Asn Leu Thr
1               5                   10                  15

Ile Asp Gln Arg Asn Ala Phe Ile Tyr Lys Leu Trp Asp
            20                  25

<210> SEQ ID NO 51
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 51

Glu Trp Arg Trp Ala Ser Ile Glu Ile Ala Asp Leu Pro Asn Leu Thr
1               5                   10                  15

Gln His Gln Arg Asp Ala Phe Ile Tyr Lys Leu Trp Asp
            20                  25

<210> SEQ ID NO 52
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 52

Glu Trp Trp Tyr Ala Ala Gly Glu Ile Ser Ser Leu Pro Asn Leu Thr
1               5                   10                  15

Glu Gln Gln Arg Asp Ala Phe Ile Tyr Lys Leu Trp Asp
            20                  25

<210> SEQ ID NO 53
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 53

Glu Trp Trp Trp Ala Ala Gly Glu Ile Ser Ser Leu Pro Asn Leu Thr
1               5                   10                  15

Ala Gln Gln Arg Asp Ala Phe Ile Tyr Lys Leu Trp Asp
            20                  25

<210> SEQ ID NO 54
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 54

Glu His Ile Phe Ala Gly Trp Glu Ile Ser Asp Leu Pro Asn Leu Thr
1               5                   10                  15

Ile Tyr Gln Arg His Ala Phe Ile Tyr Lys Leu Trp Asp
            20                  25

<210> SEQ ID NO 55
<211> LENGTH: 29
```

```
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 55

Glu Asn Ile Phe Ala Gly Trp Glu Ile Asp Asp Leu Pro Asn Leu Thr
1               5                   10                  15

Asp Asn Gln Arg His Ala Phe Ile Tyr Lys Leu Trp Asp
            20                  25

<210> SEQ ID NO 56
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 56

Glu Trp Gln Trp Ala Gly Val Glu Ile Ala Glu Leu Pro Asn Leu Thr
1               5                   10                  15

Gln Gln Gln Arg Asp Ala Phe Ile Tyr Lys Leu Trp Asp
            20                  25

<210> SEQ ID NO 57
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 57

Glu His Ile Phe Ala Gly Trp Glu Ile Thr Asp Leu Pro Asn Leu Thr
1               5                   10                  15

Ser Ser Gln Arg Asn Ala Phe Ile Tyr Lys Leu Trp Asp
            20                  25

<210> SEQ ID NO 58
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 58

Glu Trp Arg Trp Ala Gly Val Glu Ile Gln Asp Leu Pro Asn Leu Thr
1               5                   10                  15

Gln Gln Gln Arg Asp Ala Phe Ile Tyr Lys Leu Trp Asp
            20                  25

<210> SEQ ID NO 59
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 59

Glu Asn Ile Phe Ala Gly Trp Glu Ile Ser Asp Leu Pro Asn Leu Thr
1               5                   10                  15

Ile Phe Gln Arg His Ala Phe Ile Tyr Lys Leu Trp Asp
            20                  25

<210> SEQ ID NO 60
```

-continued

```
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 60

Glu Trp Gln Trp Ala Gly Val Glu Ile Gln Glu Leu Pro Asn Leu Thr
1               5                   10                  15

Gln Gln Gln Arg His Ala Phe Ile Tyr Lys Leu Trp Asp
            20                  25

<210> SEQ ID NO 61
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 61

Glu Asn Leu Phe Ala Gly Trp Glu Ile Asp Asp Leu Pro Asn Leu Thr
1               5                   10                  15

Ile Arg Gln Arg Asp Ala Phe Ile Tyr Lys Leu Trp Asp
            20                  25

<210> SEQ ID NO 62
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 62

Glu Asn Tyr Phe Ala Gly Trp Glu Ile Asp Asp Leu Pro Asn Leu Thr
1               5                   10                  15

Glu Gln Gln Arg Asn Ala Phe Ile Tyr Lys Leu Trp Asp
            20                  25

<210> SEQ ID NO 63
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 63

Glu Asn Leu Phe Ala Gly Trp Glu Ile Ala Asp Leu Pro Asn Leu Thr
1               5                   10                  15

Asp His Gln Arg Asn Ala Phe Ile Tyr Lys Leu Trp Asp
            20                  25

<210> SEQ ID NO 64
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 64

Glu Trp Ser Trp Ala Ser Val Glu Ile Ala Asp Leu Pro Asn Leu Thr
1               5                   10                  15

Gln Arg Gln Arg Asp Ala Phe Ile Tyr Lys Leu Trp Asp
            20                  25
```

```
<210> SEQ ID NO 65
<211> LENGTH: 29
<212> TYPE: PRT
<213> ORGANISM: ARTIFICIAL SEQUENCE
<220> FEATURE:
<223

<210> SEQ ID NO 70
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 70

Glu His Leu Phe Ala Gly Trp Glu Ile Glu Asp Leu Pro Asn Leu Thr
1               5                   10                  15

Ile Asp Gln Arg Asn Ala Phe Ile Tyr Lys Leu Trp Asp
            20                  25

<210> SEQ ID NO 71
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 71

Glu Asn Val Phe Ala Gly Trp Glu Ile Asp Asp Leu Pro Asn Leu Thr
1               5                   10                  15

Asp Gln Gln Arg Asn Ala Phe Ile Tyr Lys Leu Trp Asp
            20                  25

<210> SEQ ID NO 72
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 72

Glu His Ile Phe Ala Gly Trp Glu Ile Ala Asp Leu Pro Asn Leu Thr
1               5                   10                  15

Asp Gly Gln Arg Asn Ala Phe Ile Tyr Lys Leu Trp Asp
            20                  25

<210> SEQ ID NO 73
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 73

Glu Asn Ile Trp Ala Gly Trp Glu Ile Ser Asp Leu Pro Asn Leu Thr
1               5                   10                  15

Asp Thr Gln Arg Asn Ala Phe Ile Tyr Lys Leu Trp Asp
            20                  25

<210> SEQ ID NO 74
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 74

Glu Trp Gln Trp Ala Gly Ile Glu Ile Gln Asp Leu Pro Asn Leu Thr
1               5                   10                  15

Gln Arg Gln Arg Asp Ala Phe Ile Tyr Lys Leu Trp Asp
            20                  25

```
<210> SEQ ID NO 75
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 75

Glu Trp Ile Phe Ala Gly Trp Glu Ile Thr Asp Leu Pro Asn Leu Thr
1               5                   10                  15

Asp Phe Gln Arg Asn Ala Phe Ile Tyr Lys Leu Trp Asp
            20                  25

<210> SEQ ID NO 76
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 76

Glu Asn Trp Ala Ala Gly Trp Glu Ile Asp Asp Leu Pro Asn Leu Thr
1               5                   10                  15

Asp Gln Gln Arg Asp Ala Phe Ile Tyr Lys Leu Trp Asp
            20                  25

<210> SEQ ID NO 77
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 77

Glu His Leu Phe Ala Gly Trp Glu Ile Asp Glu Leu Pro Asn Leu Thr
1               5                   10                  15

Ala Tyr Gln Arg Asn Ala Phe Ile Tyr Lys Leu Trp Asp
            20                  25

<210> SEQ ID NO 78
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 78

Glu His Ile Phe Ala Gly Trp Glu Ile Glu Asp Leu Pro Asn Leu Thr
1               5                   10                  15

Glu Ser Gln Arg Asn Ala Phe Ile Tyr Lys Leu Trp Asp
            20                  25

<210> SEQ ID NO 79
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 79

Glu Asn Ile Phe Ala Gly Trp Glu Ile Asp Asp Leu Pro Asn Leu Thr
1               5                   10                  15

Ala His Gln Arg Asp Ala Phe Ile Tyr Lys Leu Trp Asp
```

-continued

```
                    20                  25

<210> SEQ ID NO 80
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 80

Glu Asn Leu Phe Ala Gly Trp Glu Ile Gly Asp Leu Pro Asn Leu Thr
1               5                   10                  15

Thr Gly Gln Arg His Ala Phe Ile Tyr Lys Leu Trp Asp
            20                  25

<210> SEQ ID NO 81
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 81

Glu His Leu Phe Ala Gly Trp Glu Ile Ser Asp Leu Pro Asn Leu Thr
1               5                   10                  15

Ala Asn Gln Arg Asp Ala Phe Ile Tyr Lys Leu Trp Asp
            20                  25

<210> SEQ ID NO 82
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 82

Glu Gln Leu Phe Ala Gly Trp Glu Ile Asp Asp Leu Pro Asn Leu Thr
1               5                   10                  15

Asp Gln Gln Arg His Ala Phe Ile Tyr Lys Leu Trp Asp
            20                  25

<210> SEQ ID NO 83
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 83

Glu Trp Gln Trp Ala Gly Val Glu Ile Asn Asp Leu Pro Asn Leu Thr
1               5                   10                  15

Gln Arg Gln Arg Asp Ala Phe Ile Tyr Lys Leu Trp Asp
            20                  25

<210> SEQ ID NO 84
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 84

Glu Trp Trp Tyr Ala Gly Val Glu Ile Ala Asp Leu Pro Asn Leu Thr
1               5                   10                  15
```

Gln Gln Gln Arg Asp Ala Phe Ile Tyr Lys Leu Trp Asp
            20                  25

<210> SEQ ID NO 85
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 85

Glu Gln Trp Trp Ala Gly Trp Glu Ile Asp Asp Leu Pro Asn Leu Thr
1               5                   10                  15

Glu Ile Gln Arg Asn Ala Phe Ile Tyr Lys Leu Trp Asp
            20                  25

<210> SEQ ID NO 86
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 86

Glu Trp Gln Trp Ala Gly Val Glu Ile Asn Glu Leu Pro Asn Leu Thr
1               5                   10                  15

Gln Arg Gln Arg Asp Ala Phe Ile Tyr Lys Leu Trp Asp
            20                  25

<210> SEQ ID NO 87
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 87

Glu Asn Ile Trp Ala Gly Trp Glu Ile Ser Asp Leu Pro Asn Leu Thr
1               5                   10                  15

Glu Asp Gln Arg Asn Ala Phe Ile Tyr Lys Leu Trp Asp
            20                  25

<210> SEQ ID NO 88
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 88

Glu His Ile Phe Ala Gly Trp Glu Ile Glu Glu Leu Pro Asn Leu Thr
1               5                   10                  15

Asp Thr Gln Arg Asn Ala Phe Ile Tyr Lys Leu Trp Asp
            20                  25

<210> SEQ ID NO 89
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 89

Glu Asp Leu Trp Ala Gly Trp Glu Ile Thr Asp Leu Pro Asn Leu Thr
1               5                   10                  15

Glu Trp Gln Arg His Ala Phe Ile Tyr Lys Leu Trp Asp
            20                  25

<210> SEQ ID NO 90
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 90

Glu Asn Ile Phe Ala Gly Trp Glu Ile Glu Asp Leu Pro Asn Leu Thr
1               5                   10                  15

Asp Asn Gln Arg Asp Ala Phe Ile Tyr Lys Leu Trp Asp
            20                  25

<210> SEQ ID NO 91
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 91

Glu Asn Leu Trp Ala Gly Trp Glu Ile Asn Asp Leu Pro Asn Leu Thr
1               5                   10                  15

Glu Gln Gln Arg Asn Ala Phe Ile Tyr Lys Leu Trp Asp
            20                  25

<210> SEQ ID NO 92
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 92

Glu Asn Ile Trp Ala Gly Trp Glu Ile Asp Asp Leu Pro Asn Leu Thr
1               5                   10                  15

Val Asn Gln Arg Asp Ala Phe Ile Tyr Lys Leu Trp Asp
            20                  25

<210> SEQ ID NO 93
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 93

Glu Gln Trp Trp Ala Gly Trp Glu Ile Asp Asp Leu Pro Asn Leu Thr
1               5                   10                  15

Glu Asp Gln Arg Asn Ala Phe Ile Tyr Lys Leu Trp Asp
            20                  25

<210> SEQ ID NO 94
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 94

Glu His Thr Asn Ala Trp Ala Glu Ile His Arg Leu Pro Asn Leu Thr

```
1               5                   10                  15
Glu Ser Gln Gln Asn Ala Phe Ile Tyr Lys Leu Trp Asp
                20                  25
```

<210> SEQ ID NO 95
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 95

```
Glu Trp Trp Tyr Ala Gly Glu Glu Ile Ala Asp Leu Pro Asn Leu Thr
1               5                   10                  15
Gln Gln Gln Gln Asp Ala Phe Ile Tyr Lys Leu Trp Asp
                20                  25
```

<210> SEQ ID NO 96
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 96

```
Glu Trp Gln Trp Ala Gly Val Glu Ile Asn Glu Leu Pro Asn Leu Thr
1               5                   10                  15
Trp Gln Gln Arg Gln Ala Phe Ile Tyr Lys Leu Trp Asp
                20                  25
```

<210> SEQ ID NO 97
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 97

```
Glu Trp Gln Trp Ala Gly Val Glu Ile Asn Asp Leu Pro Asn Leu Thr
1               5                   10                  15
Gln Gln Gln Arg Asp Ala Phe Ile Tyr Lys Leu Trp Asp
                20                  25
```

<210> SEQ ID NO 98
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 98

```
Glu Trp Arg Trp Ala Gly Val Glu Ile Ala Glu Leu Pro Asn Leu Thr
1               5                   10                  15
Gln Asn Gln Arg Asp Ala Phe Ile Tyr Lys Leu Trp Asp
                20                  25
```

<210> SEQ ID NO 99
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 99

```
Glu His Leu Phe Ala Gly Trp Glu Ile Gly Asp Leu Pro Asn Leu Thr
1               5                   10                  15

Glu Gln Gln Arg His Ala Phe Ile Tyr Lys Leu Trp Asp
            20                  25
```

<210> SEQ ID NO 100
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 100

```
Glu Asn Leu Phe Ala Gly Trp Glu Ile His Asp Leu Pro Asn Leu Thr
1               5                   10                  15

Asp Asp Gln Arg Asn Ala Phe Ile Tyr Lys Leu Trp Asp
            20                  25
```

<210> SEQ ID NO 101
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 101

```
Glu Asn Leu Phe Ala Gly Trp Glu Ile Asp Asp Leu Pro Asn Leu Thr
1               5                   10                  15

Glu Val Gln Arg Asn Ala Phe Ile Tyr Lys Leu Trp Asp
            20                  25
```

<210> SEQ ID NO 102
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 102

```
Glu Asn Leu Phe Ala Gly Trp Glu Ile Thr Asp Leu Pro Asn Leu Thr
1               5                   10                  15

Ala Ser Gln Arg His Ala Phe Ile Tyr Lys Leu Trp Asp
            20                  25
```

<210> SEQ ID NO 103
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 103

```
Glu Trp Trp Trp Ala Ala Gly Glu Ile Ser Asp Leu Pro Asn Leu Thr
1               5                   10                  15

Gly Gln Gln Arg Asp Ala Phe Ile Tyr Lys Leu Trp Asp
            20                  25
```

<210> SEQ ID NO 104
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 104

Glu Asn Ile Phe Ala Gly Trp Glu Ile Val Asp Leu Pro Asn Leu Thr
1               5                   10                  15

Glu Ile Gln Arg Asn Ala Phe Ile Tyr Lys Leu Trp Asp
            20                  25

<210> SEQ ID NO 105
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 105

Glu Asn Leu Phe Ala Gly Trp Glu Ile Arg Asp Leu Pro Asn Leu Thr
1               5                   10                  15

Glu Ala Gln Arg His Ala Phe Ile Tyr Lys Leu Trp Asp
            20                  25

<210> SEQ ID NO 106
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 106

Glu Asn Trp Trp Ala Gly Trp Glu Ile Thr Asp Leu Pro Asn Leu Thr
1               5                   10                  15

Glu His Gln Arg His Ala Phe Ile Tyr Lys Leu Trp Asp
            20                  25

<210> SEQ ID NO 107
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 107

Glu His Leu Phe Ala Gly Trp Glu Ile Gln Asp Leu Pro Asn Leu Thr
1               5                   10                  15

Glu Asp Gln Arg Asn Ala Phe Ile Tyr Lys Leu Trp Asp
            20                  25

<210> SEQ ID NO 108
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 108

Glu Asn Ile Trp Ala Gly Trp Glu Ile Gly Asp Leu Pro Asn Leu Thr
1               5                   10                  15

Glu Gln Gln Arg His Ala Phe Ile Tyr Lys Leu Trp Asp
            20                  25

<210> SEQ ID NO 109
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

```
<400> SEQUENCE: 109

Glu Trp Gln Trp Ala Gly Val Glu Ile Gln Asp Leu Pro Asn Leu Thr
1               5                   10                  15

Gly Gln Gln Arg Asp Ala Phe Ile Tyr Lys Leu Trp Asp
            20                  25

<210> SEQ ID NO 110
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 110

Glu Gln Ile Phe Ala Gly Trp Glu Ile Thr Asp Leu Pro Asn Leu Thr
1               5                   10                  15

Glu Ala Gln Arg Asn Ala Phe Ile Tyr Lys Leu Trp Asp
            20                  25

<210> SEQ ID NO 111
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 111

Glu Asn Ile Trp Ala Gly Trp Glu Ile Gly Asp Leu Pro Asn Leu Thr
1               5                   10                  15

Asp Gln Gln Arg Asn Ala Phe Ile Tyr Lys Leu Trp Asp
            20                  25

<210> SEQ ID NO 112
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 112

Glu Trp Ser Trp Ala Ser Val Glu Ile Ala Asp Leu Pro Asn Leu Thr
1               5                   10                  15

Gln Gln Gln Arg Asp Ala Phe Ile Tyr Lys Leu Trp Asp
            20                  25

<210> SEQ ID NO 113
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 113

Glu Asn Ile Phe Ala Gly Trp Glu Ile Glu Asp Leu Pro Asn Leu Thr
1               5                   10                  15

Val His Gln Arg Asp Ala Phe Ile Tyr Lys Leu Trp Asp
            20                  25

<210> SEQ ID NO 114
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide
```

```
<400> SEQUENCE: 114

Lys Glu Asn Leu Phe Ala Gly Trp Glu Ile Asp Asp Leu Pro Asn Leu
1               5                   10                  15

Thr Glu Asp Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 115
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 115

Lys Glu Asn Leu Phe Ala Gly Trp Glu Ile Ser Asp Leu Pro Asn Leu
1               5                   10                  15

Thr Asp Tyr Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 116
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 116

Lys Glu Asn Ile Phe Ala Gly Trp Glu Ile Asp Asp Leu Pro Asn Leu
1               5                   10                  15

Thr Asp Glu Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 117
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 117

Lys Glu Asn Leu Phe Ala Gly Trp Glu Ile Asp Asp Leu Pro Asn Leu
1               5                   10                  15

Thr Glu Ser Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 118
```

```
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 118

Lys Glu Trp Trp Trp Ala Gly Ile Glu Ile Ala Asp Leu Pro Asn Leu
1               5                   10                  15

Thr Gln Gln Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 119
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 119

Lys Glu His Leu Phe Ala Gly Trp Glu Ile Glu Asp Leu Pro Asn Leu
1               5                   10                  15

Thr Glu Tyr Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 120
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 120

Lys Glu Asn Leu Phe Ala Gly Trp Glu Ile Thr Asp Leu Pro Asn Leu
1               5                   10                  15

Thr Ile Glu Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 121
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 121

Lys Glu Asn Leu Phe Ala Gly Trp Glu Ile Gly Asp Leu Pro Asn Leu
1               5                   10                  15

Thr Glu Gln Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45
```

Gln

<210> SEQ ID NO 122
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 122

Lys Glu Asn Leu Phe Ala Gly Trp Glu Ile Thr Asp Leu Pro Asn Leu
1               5                   10                  15

Thr Ile Gln Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 123
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 123

Lys Glu Asn Ile Phe Ala Gly Trp Glu Ile Asp Asp Leu Pro Asn Leu
1               5                   10                  15

Thr Thr Tyr Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 124
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 124

Lys Glu Asn Leu Phe Ala Gly Trp Glu Ile Asn Asp Leu Pro Asn Leu
1               5                   10                  15

Thr Glu Tyr Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 125
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 125

Lys Glu His Leu Phe Ala Gly Trp Glu Ile Thr Asp Leu Pro Asn Leu
1               5                   10                  15

Thr Glu Gln Gln Arg Asn Ala Phe Ile Tyr Lys Leu Trp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 126
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 126

Lys Glu Asn Ile Phe Ala Gly Trp Glu Ile Thr Asp Leu Pro Asn Leu
1               5                   10                  15

Thr Val Gln Gln Arg His Ala Phe Ile Tyr Lys Leu Trp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 127
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 127

Lys Glu Asn Ile Phe Ala Gly Trp Glu Ile Asp Glu Leu Pro Asn Leu
1               5                   10                  15

Thr Glu Tyr Gln Arg Asn Ala Phe Ile Tyr Lys Leu Trp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 128
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 128

Lys Glu His Ile Phe Ala Gly Trp Glu Ile Thr Asp Leu Pro Asn Leu
1               5                   10                  15

Thr Asp Asp Gln Arg Asn Ala Phe Ile Tyr Lys Leu Trp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 129
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

```
<400> SEQUENCE: 129

Lys Glu Asn Ile Phe Ala Gly Trp Glu Ile Ser Asp Leu Pro Asn Leu
1               5                   10                  15

Thr Val Ala Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 130
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 130

Lys Glu Asp Leu Phe Ala Gly Trp Glu Ile Asp Asp Leu Pro Asn Leu
1               5                   10                  15

Thr Glu Tyr Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 131
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 131

Lys Glu Asn Ile Phe Ala Gly Trp Glu Ile Asp Asp Leu Pro Asn Leu
1               5                   10                  15

Thr Glu Ser Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 132
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 132

Lys Glu Asn Leu Phe Ala Gly Trp Glu Ile Thr Asp Leu Pro Asn Leu
1               5                   10                  15

Thr Asp Tyr Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 133
<211> LENGTH: 49
```

```
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 133
```

Lys Glu Asn Leu Phe Ala Gly Trp Glu Ile Ser Asp Leu Pro Asn Leu
1               5                   10                  15

Thr Gln Gln Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

```
<210> SEQ ID NO 134
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 134
```

Lys Glu Asn Ile Phe Ala Gly Trp Glu Ile Glu Asp Leu Pro Asn Leu
1               5                   10                  15

Thr Asp His Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

```
<210> SEQ ID NO 135
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 135
```

Lys Glu Asn Ile Phe Ala Gly Trp Glu Ile Arg Asp Leu Pro Asn Leu
1               5                   10                  15

Thr Asp Tyr Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

```
<210> SEQ ID NO 136
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 136
```

Lys Glu Asn Trp Ala Ala Gly Trp Glu Ile Ser Asp Leu Pro Asn Leu
1               5                   10                  15

Thr Asp Phe Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 137
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 137

Lys Glu Asn Ile Phe Ala Gly Trp Glu Ile Gly Asp Leu Pro Asn Leu
1               5                   10                  15

Thr Glu Asp Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 138
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 138

Lys Glu Asn Ile Phe Ala Gly Trp Glu Ile Asp Asp Leu Pro Asn Leu
1               5                   10                  15

Thr Glu Ala Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 139
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 139

Lys Glu Gln Leu Phe Ala Gly Trp Glu Ile Asp Asp Leu Pro Asn Leu
1               5                   10                  15

Thr Glu Phe Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 140
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 140

Lys Glu Trp Arg Tyr Ala Ser Ile Glu Ile Ala Asp Leu Pro Asn Leu
1               5                   10                  15

Thr Gln Arg Gln Arg Asp Ala Phe Ile Tyr Lys Leu Trp Asp Asp Pro 20                  25                  30

Ser Gln Ser Ser Glu Leu Leu Ser Glu Ala Lys Lys Leu Asn Asp Ser
        35                  40                  45

Gln

<210> SEQ ID NO 141
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 141

Lys Glu Asn Trp Ala Ala Gly Trp Glu Ile Asp Asp Leu Pro Asn Leu
1               5                   10                  15

Thr Ile Asp Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 142
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 142

Lys Glu Gln Leu Phe Ala Gly Trp Glu Ile Asp Asp Leu Pro Asn Leu
1               5                   10                  15

Thr Asp Phe Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 143
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 143

Lys Glu Asn Ile Phe Ala Gly Trp Glu Ile Glu Glu Leu Pro Asn Leu
1               5                   10                  15

Thr Glu Phe Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 144
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 144

-continued

Lys Glu Asn Leu Phe Ala Gly Trp Glu Ile Gly Asp Leu Pro Asn Leu
1               5                   10                  15

Thr Glu Asp Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 145
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 145

Lys Glu Asn Ile Phe Ala Gly Trp Glu Ile Glu Asp Leu Pro Asn Leu
1               5                   10                  15

Thr Asp Gln Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 146
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 146

Lys Glu His Ile Phe Ala Gly Trp Glu Ile Ser Asp Leu Pro Asn Leu
1               5                   10                  15

Thr Glu Gln Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 147
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 147

Lys Glu Asn Leu Phe Ala Gly Trp Glu Ile Asp Asp Leu Pro Asn Leu
1               5                   10                  15

Thr Val Gln Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 148
<211> LENGTH: 49
<212> TYPE: PRT

<213> ORGANISM: ARTIFICIAL SEQUENCE
<220> FEATURE:
<223> OTHER INFORMATION: Engineered CAIX-binding polypeptide

<400> SEQUENCE: 148

Lys Glu His Leu Phe Ala Gly Trp Glu Ile Asp Asp Leu Pro Asn Leu
1               5                   10                  15

Thr Asp His Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 149
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 149

Lys Glu Asn Ile Phe Ala Gly Trp Glu Ile Ser Asp Leu Pro Asn Leu
1               5                   10                  15

Thr Ile Asp Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 150
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 150

Lys Glu Asn Ile Trp Ala Gly Trp Glu Ile Asp Asp Leu Pro Asn Leu
1               5                   10                  15

Thr Glu Arg Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 151
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 151

Lys Glu Asn Ile Phe Ala Gly Trp Glu Ile Glu Asp Leu Pro Asn Leu
1               5                   10                  15

Thr Asp Gly Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 152
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 152

Lys Glu Asn Ile Phe Ala Gly Trp Glu Ile Ser Asp Leu Pro Asn Leu
1               5                   10                  15

Thr Glu His Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 153
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 153

Lys Glu Asn Ile Phe Ala Gly Trp Glu Ile Glu Asp Leu Pro Asn Leu
1               5                   10                  15

Thr Asp His Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 154
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 154

Lys Glu His Trp Ala Ala Gly Trp Glu Ile Asp Asp Leu Pro Asn Leu
1               5                   10                  15

Thr Glu Phe Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 155
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 155

Lys Glu His Leu Phe Ala Gly Trp Glu Ile Thr Asp Leu Pro Asn Leu
1               5                   10                  15

Thr Asp Gln Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 156
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 156

Lys Glu Gln Leu Phe Ala Gly Trp Glu Ile Asp Asp Leu Pro Asn Leu
1               5                   10                  15

Thr Glu Ala Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 157
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 157

Lys Glu Gln Leu Phe Ala Gly Trp Glu Ile Ser Asp Leu Pro Asn Leu
1               5                   10                  15

Thr Glu Gln Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 158
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 158

Lys Glu Asn Leu Phe Ala Gly Trp Glu Ile Asp Asp Leu Pro Asn Leu
1               5                   10                  15

Thr Trp Gln Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 159
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 159

-continued

Lys Glu Asn Ile Phe Ala Gly Trp Glu Ile Gln Asp Leu Pro Asn Leu
1               5                   10                  15

Thr Ile Glu Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 160
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 160

Lys Glu Trp Trp Trp Ala Ala Gly Glu Ile Thr Glu Leu Pro Asn Leu
1               5                   10                  15

Thr Glu Gln Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 161
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 161

Lys Glu Trp Gln Trp Ala Gly Val Glu Ile Gln Asp Leu Pro Asn Leu
1               5                   10                  15

Thr Asp Asn Gln Arg Gln Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 162
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 162

Lys Glu Asn Trp Ala Ala Gly Trp Glu Ile Thr Asp Leu Pro Asn Leu
1               5                   10                  15

Thr Ser Ser Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 163
<211> LENGTH: 49
<212> TYPE: PRT
<213> ORGANISM: ARTIFICIAL SEQUENCE

```
<220> FEATURE:
<223> OTHER INFORMATION: Engineered CAIX-binding polypeptide

<400> SEQUENCE: 163

Lys Glu His Leu Phe Ala Gly Trp Glu Ile Thr Asp Leu Pro Asn Leu
1               5                   10                  15

Thr Ile Asp Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 164
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 164

Lys Glu Trp Arg Trp Ala Ser Ile Glu Ile Ala Asp Leu Pro Asn Leu
1               5                   10                  15

Thr Gln His Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 165
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 165

Lys Glu Trp Trp Tyr Ala Ala Gly Glu Ile Ser Ser Leu Pro Asn Leu
1               5                   10                  15

Thr Glu Gln Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 166
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 166

Lys Glu Trp Trp Trp Ala Ala Gly Glu Ile Ser Ser Leu Pro Asn Leu
1               5                   10                  15

Thr Ala Gln Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln
```

-continued

<210> SEQ ID NO 167
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 167

Lys Glu His Ile Phe Ala Gly Trp Glu Ile Ser Asp Leu Pro Asn Leu
1               5                   10                  15

Thr Ile Tyr Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 168
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 168

Lys Glu Asn Ile Phe Ala Gly Trp Glu Ile Asp Asp Leu Pro Asn Leu
1               5                   10                  15

Thr Asp Asn Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 169
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 169

Lys Glu Trp Gln Trp Ala Gly Val Glu Ile Ala Glu Leu Pro Asn Leu
1               5                   10                  15

Thr Gln Gln Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 170
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 170

Lys Glu His Ile Phe Ala Gly Trp Glu Ile Thr Asp Leu Pro Asn Leu
1               5                   10                  15

Thr Ser Ser Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 171
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 171

Lys Glu Trp Arg Trp Ala Gly Val Glu Ile Gln Asp Leu Pro Asn Leu
1               5                   10                  15

Thr Gln Gln Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 172
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 172

Lys Glu Asn Ile Phe Ala Gly Trp Glu Ile Ser Asp Leu Pro Asn Leu
1               5                   10                  15

Thr Ile Phe Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 173
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 173

Lys Glu Trp Gln Trp Ala Gly Val Glu Ile Gln Glu Leu Pro Asn Leu
1               5                   10                  15

Thr Gln Gln Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 174
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 174

Lys Glu Asn Leu Phe Ala Gly Trp Glu Ile Asp Asp Leu Pro Asn Leu

```
                1               5                  10                  15
Thr Ile Arg Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 175
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 175

Lys Glu Asn Tyr Phe Ala Gly Trp Glu Ile Asp Asp Leu Pro Asn Leu
1               5                   10                  15

Thr Glu Gln Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 176
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 176

Lys Glu Asn Leu Phe Ala Gly Trp Glu Ile Ala Asp Leu Pro Asn Leu
1               5                   10                  15

Thr Asp His Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 177
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 177

Lys Glu Trp Ser Trp Ala Ser Val Glu Ile Ala Asp Leu Pro Asn Leu
1               5                   10                  15

Thr Gln Arg Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 178
<211> LENGTH: 49
<212> TYPE: PRT
<213> ORGANISM: ARTIFICIAL SEQUENCE
<220> FEATURE:
```

<223> OTHER INFORMATION: Engineered CAIX-binding polypeptide

<400> SEQUENCE: 178

Lys Glu Asp Ile Phe Ala Gly Trp Glu Ile Thr Asp Leu Pro Asn Leu
1               5                   10                  15

Thr Asp His Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 179
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 179

Lys Glu Gln Leu Phe Ala Gly Trp Glu Ile Asp Asp Leu Pro Asn Leu
1               5                   10                  15

Thr Ile Asp Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 180
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 180

Lys Glu Asn Trp Phe Ala Gly Trp Glu Ile Asp Asp Leu Pro Asn Leu
1               5                   10                  15

Thr Glu Arg Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 181
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 181

Lys Glu His Leu Phe Ala Gly Trp Glu Ile Asp Glu Leu Pro Asn Leu
1               5                   10                  15

Thr Glu Gln Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

-continued

```
<210> SEQ ID NO 182
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 182

Lys Glu Asn Phe Trp Ala Gly Trp Glu Ile Asp Asp Leu Pro Asn Leu
1               5                   10                  15

Thr Glu Leu Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 183
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 183

Lys Glu His Leu Phe Ala Gly Trp Glu Ile Glu Asp Leu Pro Asn Leu
1               5                   10                  15

Thr Ile Asp Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 184
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 184

Lys Glu Asn Val Phe Ala Gly Trp Glu Ile Asp Asp Leu Pro Asn Leu
1               5                   10                  15

Thr Asp Gln Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 185
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 185

Lys Glu His Ile Phe Ala Gly Trp Glu Ile Ala Asp Leu Pro Asn Leu
1               5                   10                  15

Thr Asp Gly Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
```

35                  40                  45

Gln

<210> SEQ ID NO 186
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 186

Lys Glu Asn Ile Trp Ala Gly Trp Glu Ile Ser Asp Leu Pro Asn Leu
1               5                   10                  15

Thr Asp Thr Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 187
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 187

Lys Glu Trp Gln Trp Ala Gly Ile Glu Ile Gln Asp Leu Pro Asn Leu
1               5                   10                  15

Thr Gln Arg Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 188
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 188

Lys Glu Trp Ile Phe Ala Gly Trp Glu Ile Thr Asp Leu Pro Asn Leu
1               5                   10                  15

Thr Asp Phe Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 189
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 189

Lys Glu Asn Trp Ala Ala Gly Trp Glu Ile Asp Asp Leu Pro Asn Leu
1               5                   10                  15

```
Thr Asp Gln Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 190
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 190

Lys Glu His Leu Phe Ala Gly Trp Glu Ile Asp Glu Leu Pro Asn Leu
1               5                   10                  15

Thr Ala Tyr Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 191
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 191

Lys Glu His Ile Phe Ala Gly Trp Glu Ile Glu Asp Leu Pro Asn Leu
1               5                   10                  15

Thr Glu Ser Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 192
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 192

Lys Glu Asn Ile Phe Ala Gly Trp Glu Ile Asp Asp Leu Pro Asn Leu
1               5                   10                  15

Thr Ala His Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 193
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide
```

<400> SEQUENCE: 193

Lys Glu Asn Leu Phe Ala Gly Trp Glu Ile Gly Asp Leu Pro Asn Leu
1               5                   10                  15

Thr Thr Gly Gln Arg His Ala Phe Ile Tyr Lys Leu Trp Asp Asp Pro
                20                  25                  30

Ser Gln Ser Ser Glu Leu Leu Ser Glu Ala Lys Lys Leu Asn Asp Ser
        35                  40                  45

Gln

<210> SEQ ID NO 194
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 194

Lys Glu His Leu Phe Ala Gly Trp Glu Ile Ser Asp Leu Pro Asn Leu
1               5                   10                  15

Thr Ala Asn Gln Arg Asp Ala Phe Ile Tyr Lys Leu Trp Asp Asp Pro
                20                  25                  30

Ser Gln Ser Ser Glu Leu Leu Ser Glu Ala Lys Lys Leu Asn Asp Ser
        35                  40                  45

Gln

<210> SEQ ID NO 195
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 195

Lys Glu Gln Leu Phe Ala Gly Trp Glu Ile Asp Asp Leu Pro Asn Leu
1               5                   10                  15

Thr Asp Gln Gln Arg His Ala Phe Ile Tyr Lys Leu Trp Asp Asp Pro
                20                  25                  30

Ser Gln Ser Ser Glu Leu Leu Ser Glu Ala Lys Lys Leu Asn Asp Ser
        35                  40                  45

Gln

<210> SEQ ID NO 196
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 196

Lys Glu Trp Gln Trp Ala Gly Val Glu Ile Asn Asp Leu Pro Asn Leu
1               5                   10                  15

Thr Gln Arg Gln Arg Asp Ala Phe Ile Tyr Lys Leu Trp Asp Asp Pro
                20                  25                  30

Ser Gln Ser Ser Glu Leu Leu Ser Glu Ala Lys Lys Leu Asn Asp Ser
        35                  40                  45

Gln

<210> SEQ ID NO 197

```
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 197

Lys Glu Trp Trp Tyr Ala Gly Val Glu Ile Ala Asp Leu Pro Asn Leu
1               5                   10                  15

Thr Gln Gln Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 198
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 198

Lys Glu Gln Trp Trp Ala Gly Trp Glu Ile Asp Asp Leu Pro Asn Leu
1               5                   10                  15

Thr Glu Ile Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 199
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 199

Lys Glu Trp Gln Trp Ala Gly Val Glu Ile Asn Glu Leu Pro Asn Leu
1               5                   10                  15

Thr Gln Arg Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 200
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 200

Lys Glu Asn Ile Trp Ala Gly Trp Glu Ile Ser Asp Leu Pro Asn Leu
1               5                   10                  15

Thr Glu Asp Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45
```

Gln

<210> SEQ ID NO 201
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 201

Lys Glu His Ile Phe Ala Gly Trp Glu Ile Glu Leu Pro Asn Leu
1               5                   10                  15

Thr Asp Thr Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 202
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 202

Lys Glu Asp Leu Trp Ala Gly Trp Glu Ile Thr Asp Leu Pro Asn Leu
1               5                   10                  15

Thr Glu Trp Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 203
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 203

Lys Glu Asn Ile Phe Ala Gly Trp Glu Ile Glu Asp Leu Pro Asn Leu
1               5                   10                  15

Thr Asp Asn Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 204
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 204

Lys Glu Asn Leu Trp Ala Gly Trp Glu Ile Asn Asp Leu Pro Asn Leu
1               5                   10                  15

-continued

Thr Glu Gln Gln Arg Asn Ala Phe Ile Tyr Lys Leu Trp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 205
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 205

Lys Glu Asn Ile Trp Ala Gly Trp Glu Ile Asp Asp Leu Pro Asn Leu
1               5                   10                  15

Thr Val Asn Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 206
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 206

Lys Glu Gln Trp Trp Ala Gly Trp Glu Ile Asp Asp Leu Pro Asn Leu
1               5                   10                  15

Thr Glu Asp Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 207
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 207

Lys Glu His Thr Asn Ala Trp Ala Glu Ile His Arg Leu Pro Asn Leu
1               5                   10                  15

Thr Glu Ser Gln Gln Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 208
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide -continued

```
<400> SEQUENCE: 208

Lys Glu Trp Trp Tyr Ala Gly Glu Ile Ala Asp Leu Pro Asn Leu
1               5                   10                  15

Thr Gln Gln Gln Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 209
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 209

Lys Glu Trp Gln Trp Ala Gly Val Glu Ile Asn Glu Leu Pro Asn Leu
1               5                   10                  15

Thr Trp Gln Gln Arg Gln Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 210
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 210

Lys Glu Trp Gln Trp Ala Gly Val Glu Ile Asn Asp Leu Pro Asn Leu
1               5                   10                  15

Thr Gln Gln Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 211
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 211

Lys Glu Trp Arg Trp Ala Gly Val Glu Ile Ala Glu Leu Pro Asn Leu
1               5                   10                  15

Thr Gln Asn Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 212
<211> LENGTH: 49
```

```
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 212

Lys Glu His Leu Phe Ala Gly Trp Glu Ile Gly Asp Leu Pro Asn Leu
1               5                   10                  15

Thr Glu Gln Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 213
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 213

Lys Glu Asn Leu Phe Ala Gly Trp Glu Ile His Asp Leu Pro Asn Leu
1               5                   10                  15

Thr Asp Asp Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 214
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 214

Lys Glu Asn Leu Phe Ala Gly Trp Glu Ile Asp Asp Leu Pro Asn Leu
1               5                   10                  15

Thr Glu Val Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 215
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 215

Lys Glu Asn Leu Phe Ala Gly Trp Glu Ile Thr Asp Leu Pro Asn Leu
1               5                   10                  15

Thr Ala Ser Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45
```

Gln

<210> SEQ ID NO 216
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 216

Lys Glu Trp Trp Trp Ala Ala Gly Glu Ile Ser Asp Leu Pro Asn Leu
1               5                   10                  15

Thr Gly Gln Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 217
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 217

Lys Glu Asn Ile Phe Ala Gly Trp Glu Ile Val Asp Leu Pro Asn Leu
1               5                   10                  15

Thr Glu Ile Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 218
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 218

Lys Glu Asn Leu Phe Ala Gly Trp Glu Ile Arg Asp Leu Pro Asn Leu
1               5                   10                  15

Thr Glu Ala Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 219
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 219

Lys Glu Asn Trp Trp Ala Gly Trp Glu Ile Thr Asp Leu Pro Asn Leu
1               5                   10                  15

Thr Glu His Gln Arg His Ala Phe Ile Tyr Lys Leu Trp Asp Asp Pro

-continued

```
                20                  25                  30
Ser Gln Ser Ser Glu Leu Leu Ser Glu Ala Lys Lys Leu Asn Asp Ser
        35                  40                  45

Gln

<210> SEQ ID NO 220
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 220

Lys Glu His Leu Phe Ala Gly Trp Glu Ile Gln Asp Leu Pro Asn Leu
1               5                   10                  15

Thr Glu Asp Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 221
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 221

Lys Glu Asn Ile Trp Ala Gly Trp Glu Ile Gly Asp Leu Pro Asn Leu
1               5                   10                  15

Thr Glu Gln Gln Arg His Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 222
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 222

Lys Glu Trp Gln Trp Ala Gly Val Glu Ile Gln Asp Leu Pro Asn Leu
1               5                   10                  15

Thr Gly Gln Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 223
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 223
```

```
Lys Glu Gln Ile Phe Ala Gly Trp Glu Ile Thr Asp Leu Pro Asn Leu
1               5                   10                  15

Thr Glu Ala Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 224
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 224

```
Lys Glu Asn Ile Trp Ala Gly Trp Glu Ile Gly Asp Leu Pro Asn Leu
1               5                   10                  15

Thr Asp Gln Gln Arg Asn Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 225
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 225

```
Lys Glu Trp Ser Trp Ala Ser Val Glu Ile Ala Asp Leu Pro Asn Leu
1               5                   10                  15

Thr Gln Gln Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 226
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 226

```
Lys Glu Asn Ile Phe Ala Gly Trp Glu Ile Glu Asp Leu Pro Asn Leu
1               5                   10                  15

Thr Val His Gln Arg Asp Ala Phe Ile Tyr Lys Leu Trp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 227
<211> LENGTH: 58
<212> TYPE: PRT

```
<213> ORGANISM: ARTIFICIAL SEQUENCE
<220> FEATURE:
<223> OTHER INFORMATION: Engineered CAIX-binding polypeptide

<400> SEQUENCE: 227

Val Asp Ala Lys Tyr Ala Lys Glu Asn Leu Phe Ala Gly Trp Glu Ile
1               5                   10                  15

Asp Asp Leu Pro Asn Leu Thr Glu Asp Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 228
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 228

Val Asp Ala Lys Tyr Ala Lys Glu Asn Leu Phe Ala Gly Trp Glu Ile
1               5                   10                  15

Ser Asp Leu Pro Asn Leu Thr Asp Tyr Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 229
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 229

Val Asp Ala Lys Tyr Ala Lys Glu Asn Ile Phe Ala Gly Trp Glu Ile
1               5                   10                  15

Asp Asp Leu Pro Asn Leu Thr Asp Glu Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 230
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 230

Val Asp Ala Lys Tyr Ala Lys Glu Asn Leu Phe Ala Gly Trp Glu Ile
1               5                   10                  15

Asp Asp Leu Pro Asn Leu Thr Glu Ser Gln Arg Asn Ala Phe Ile Tyr
            20                  25                  30

Lys Leu Trp Asp Asp Pro Ser Gln Ser Ser Glu Leu Leu Ser Glu Ala
```

-continued

```
                35                  40                  45

Lys Lys Leu Asn Asp Ser Gln Ala Pro Lys
    50                  55

<210> SEQ ID NO 231
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 231

Val Asp Ala Lys Tyr Ala Lys Glu Trp Trp Trp Ala Gly Ile Glu Ile
1               5                   10                  15

Ala Asp Leu Pro Asn Leu Thr Gln Gln Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 232
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 232

Val Asp Ala Lys Tyr Ala Lys Glu His Leu Phe Ala Gly Trp Glu Ile
1               5                   10                  15

Glu Asp Leu Pro Asn Leu Thr Glu Tyr Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 233
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 233

Val Asp Ala Lys Tyr Ala Lys Glu Asn Leu Phe Ala Gly Trp Glu Ile
1               5                   10                  15

Thr Asp Leu Pro Asn Leu Thr Ile Glu Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 234
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide
```

-continued

<400> SEQUENCE: 234

Val Asp Ala Lys Tyr Ala Lys Glu Asn Leu Phe Ala Gly Trp Glu Ile
1               5                   10                  15

Gly Asp Leu Pro Asn Leu Thr Glu Gln Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 235
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 235

Val Asp Ala Lys Tyr Ala Lys Glu Asn Leu Phe Ala Gly Trp Glu Ile
1               5                   10                  15

Thr Asp Leu Pro Asn Leu Thr Ile Gln Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 236
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 236

Val Asp Ala Lys Tyr Ala Lys Glu Asn Ile Phe Ala Gly Trp Glu Ile
1               5                   10                  15

Asp Asp Leu Pro Asn Leu Thr Thr Tyr Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 237
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 237

Val Asp Ala Lys Tyr Ala Lys Glu Asn Leu Phe Ala Gly Trp Glu Ile
1               5                   10                  15

Asn Asp Leu Pro Asn Leu Thr Glu Tyr Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

```
<210> SEQ ID NO 238
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 238

Val Asp Ala Lys Tyr Ala Lys Glu His Leu Phe Ala Gly Trp Glu Ile
1               5                   10                  15

Thr Asp Leu Pro Asn Leu Thr Glu Gln Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 239
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 239

Val Asp Ala Lys Tyr Ala Lys Glu Asn Ile Phe Ala Gly Trp Glu Ile
1               5                   10                  15

Thr Asp Leu Pro Asn Leu Thr Val Gln Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 240
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 240

Val Asp Ala Lys Tyr Ala Lys Glu Asn Ile Phe Ala Gly Trp Glu Ile
1               5                   10                  15

Asp Glu Leu Pro Asn Leu Thr Glu Tyr Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 241
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 241

Val Asp Ala Lys Tyr Ala Lys Glu His Ile Phe Ala Gly Trp Glu Ile
1               5                   10                  15
```

Thr Asp Leu Pro Asn Leu Thr Asp Asp Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 242
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 242

Val Asp Ala Lys Tyr Ala Lys Glu Asn Ile Phe Ala Gly Trp Glu Ile
1               5                   10                  15

Ser Asp Leu Pro Asn Leu Thr Val Ala Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 243
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 243

Val Asp Ala Lys Tyr Ala Lys Glu Asp Leu Phe Ala Gly Trp Glu Ile
1               5                   10                  15

Asp Asp Leu Pro Asn Leu Thr Glu Tyr Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 244
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 244

Val Asp Ala Lys Tyr Ala Lys Glu Asn Ile Phe Ala Gly Trp Glu Ile
1               5                   10                  15

Asp Asp Leu Pro Asn Leu Thr Glu Ser Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 245
<211> LENGTH: 58

```
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 245

Val Asp Ala Lys Tyr Ala Lys Glu Asn Leu Phe Ala Gly Trp Glu Ile
1               5                   10                  15

Thr Asp Leu Pro Asn Leu Thr Asp Tyr Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 246
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 246

Val Asp Ala Lys Tyr Ala Lys Glu Asn Leu Phe Ala Gly Trp Glu Ile
1               5                   10                  15

Ser Asp Leu Pro Asn Leu Thr Gln Gln Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 247
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 247

Val Asp Ala Lys Tyr Ala Lys Glu Asn Ile Phe Ala Gly Trp Glu Ile
1               5                   10                  15

Glu Asp Leu Pro Asn Leu Thr Asp His Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 248
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 248

Val Asp Ala Lys Tyr Ala Lys Glu Asn Ile Phe Ala Gly Trp Glu Ile
1               5                   10                  15

Arg Asp Leu Pro Asn Leu Thr Asp Tyr Gln Arg Asn Ala Phe Ile Tyr
            20                  25                  30
```

```
Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 249
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 249

```
Val Asp Ala Lys Tyr Ala Lys Glu Asn Trp Ala Ala Gly Trp Glu Ile
1               5                   10                  15

Ser Asp Leu Pro Asn Leu Thr Asp Phe Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 250
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 250

```
Val Asp Ala Lys Tyr Ala Lys Glu Asn Ile Phe Ala Gly Trp Glu Ile
1               5                   10                  15

Gly Asp Leu Pro Asn Leu Thr Glu Asp Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 251
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 251

```
Val Asp Ala Lys Tyr Ala Lys Glu Asn Ile Phe Ala Gly Trp Glu Ile
1               5                   10                  15

Asp Asp Leu Pro Asn Leu Thr Glu Ala Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 252
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide -continued

<400> SEQUENCE: 252

Val Asp Ala Lys Tyr Ala Lys Glu Gln Leu Phe Ala Gly Trp Glu Ile
1               5                   10                  15

Asp Asp Leu Pro Asn Leu Thr Glu Phe Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 253
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 253

Val Asp Ala Lys Tyr Ala Lys Glu Trp Arg Tyr Ala Ser Ile Glu Ile
1               5                   10                  15

Ala Asp Leu Pro Asn Leu Thr Gln Arg Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 254
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 254

Val Asp Ala Lys Tyr Ala Lys Glu Asn Trp Ala Ala Gly Trp Glu Ile
1               5                   10                  15

Asp Asp Leu Pro Asn Leu Thr Ile Asp Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 255
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 255

Val Asp Ala Lys Tyr Ala Lys Glu Gln Leu Phe Ala Gly Trp Glu Ile
1               5                   10                  15

Asp Asp Leu Pro Asn Leu Thr Asp Phe Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys

<210> SEQ ID NO 256
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 256

Val Asp Ala Lys Tyr Ala Lys Glu Asn Ile Phe Ala Gly Trp Glu Ile
1               5                   10                  15

Glu Glu Leu Pro Asn Leu Thr Glu Phe Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 257
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 257

Val Asp Ala Lys Tyr Ala Lys Glu Asn Leu Phe Ala Gly Trp Glu Ile
1               5                   10                  15

Gly Asp Leu Pro Asn Leu Thr Glu Asp Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 258
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 258

Val Asp Ala Lys Tyr Ala Lys Glu Asn Ile Phe Ala Gly Trp Glu Ile
1               5                   10                  15

Glu Asp Leu Pro Asn Leu Thr Asp Gln Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 259
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 259

Val Asp Ala Lys Tyr Ala Lys Glu His Ile Phe Ala Gly Trp Glu Ile

```
                1               5                  10                  15
Ser Asp Leu Pro Asn Leu Thr Glu Gln Gln Arg His Ala Phe Ile Tyr
        20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
        50                  55
```

<210> SEQ ID NO 260
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 260

```
Val Asp Ala Lys Tyr Ala Lys Glu Asn Leu Phe Ala Gly Trp Glu Ile
1               5                  10                  15

Asp Asp Leu Pro Asn Leu Thr Val Gln Gln Arg Asn Ala Phe Ile Tyr
        20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
        50                  55
```

<210> SEQ ID NO 261
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 261

```
Val Asp Ala Lys Tyr Ala Lys Glu His Leu Phe Ala Gly Trp Glu Ile
1               5                  10                  15

Asp Asp Leu Pro Asn Leu Thr Asp His Gln Arg Asn Ala Phe Ile Tyr
        20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
        50                  55
```

<210> SEQ ID NO 262
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 262

```
Val Asp Ala Lys Tyr Ala Lys Glu Asn Ile Phe Ala Gly Trp Glu Ile
1               5                  10                  15

Ser Asp Leu Pro Asn Leu Thr Ile Asp Gln Arg Asn Ala Phe Ile Tyr
        20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
        50                  55
```

<210> SEQ ID NO 263

<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 263

Val Asp Ala Lys Tyr Ala Lys Glu Asn Ile Trp Ala Gly Trp Glu Ile
1               5                   10                  15

Asp Asp Leu Pro Asn Leu Thr Glu Arg Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 264
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 264

Val Asp Ala Lys Tyr Ala Lys Glu Asn Ile Phe Ala Gly Trp Glu Ile
1               5                   10                  15

Glu Asp Leu Pro Asn Leu Thr Asp Gly Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 265
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 265

Val Asp Ala Lys Tyr Ala Lys Glu Asn Ile Phe Ala Gly Trp Glu Ile
1               5                   10                  15

Ser Asp Leu Pro Asn Leu Thr Glu His Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 266
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 266

Val Asp Ala Lys Tyr Ala Lys Glu Asn Ile Phe Ala Gly Trp Glu Ile
1               5                   10                  15

Glu Asp Leu Pro Asn Leu Thr Asp His Gln Arg Asp Ala Phe Ile Tyr
            20                  25                  30

```
Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 267
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 267

Val Asp Ala Lys Tyr Ala Lys Glu His Trp Ala Ala Gly Trp Glu Ile
1               5                   10                  15

Asp Asp Leu Pro Asn Leu Thr Glu Phe Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 268
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 268

Val Asp Ala Lys Tyr Ala Lys Glu His Leu Phe Ala Gly Trp Glu Ile
1               5                   10                  15

Thr Asp Leu Pro Asn Leu Thr Asp Gln Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 269
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 269

Val Asp Ala Lys Tyr Ala Lys Glu Gln Leu Phe Ala Gly Trp Glu Ile
1               5                   10                  15

Asp Asp Leu Pro Asn Leu Thr Glu Ala Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 270
<211> LENGTH: 58
<212> TYPE: PRT
<213> ORGANISM: ARTIFICIAL SEQUENCE
<220> FEATURE:
```

<223> OTHER INFORMATION: Engineered CAIX-binding polypeptide

<400> SEQUENCE: 270

Val Asp Ala Lys Tyr Ala Lys Glu Gln Leu Phe Ala Gly Trp Glu Ile
1               5                   10                  15

Ser Asp Leu Pro Asn Leu Thr Glu Gln Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 271
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 271

Val Asp Ala Lys Tyr Ala Lys Glu Asn Leu Phe Ala Gly Trp Glu Ile
1               5                   10                  15

Asp Asp Leu Pro Asn Leu Thr Trp Gln Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 272
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 272

Val Asp Ala Lys Tyr Ala Lys Glu Asn Ile Phe Ala Gly Trp Glu Ile
1               5                   10                  15

Gln Asp Leu Pro Asn Leu Thr Ile Glu Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 273
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 273

Val Asp Ala Lys Tyr Ala Lys Glu Trp Trp Trp Ala Ala Gly Glu Ile
1               5                   10                  15

Thr Glu Leu Pro Asn Leu Thr Glu Gln Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

```
Lys Lys Leu Asn Asp Ser Gln Ala Pro Lys
    50                  55
```

<210> SEQ ID NO 274
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 274

```
Val Asp Ala Lys Tyr Ala Lys Glu Trp Gln Trp Ala Gly Val Glu Ile
1               5                   10                  15

Gln Asp Leu Pro Asn Leu Thr Asp Asn Gln Arg Gln Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 275
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 275

```
Val Asp Ala Lys Tyr Ala Lys Glu Asn Trp Ala Ala Gly Trp Glu Ile
1               5                   10                  15

Thr Asp Leu Pro Asn Leu Thr Ser Ser Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 276
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 276

```
Val Asp Ala Lys Tyr Ala Lys Glu His Leu Phe Ala Gly Trp Glu Ile
1               5                   10                  15

Thr Asp Leu Pro Asn Leu Thr Ile Asp Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 277
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 277

-continued

```
Val Asp Ala Lys Tyr Ala Lys Glu Trp Arg Trp Ala Ser Ile Glu Ile
1               5                   10                  15

Ala Asp Leu Pro Asn Leu Thr Gln His Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 278
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 278

```
Val Asp Ala Lys Tyr Ala Lys Glu Trp Trp Tyr Ala Ala Gly Glu Ile
1               5                   10                  15

Ser Ser Leu Pro Asn Leu Thr Glu Gln Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 279
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 279

```
Val Asp Ala Lys Tyr Ala Lys Glu Trp Trp Trp Ala Ala Gly Glu Ile
1               5                   10                  15

Ser Ser Leu Pro Asn Leu Thr Ala Gln Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 280
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 280

```
Val Asp Ala Lys Tyr Ala Lys Glu His Ile Phe Ala Gly Trp Glu Ile
1               5                   10                  15

Ser Asp Leu Pro Asn Leu Thr Ile Tyr Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55
```

```
<210> SEQ ID NO 281
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 281

Val Asp Ala Lys Tyr Ala Lys Glu Asn Ile Phe Ala Gly Trp Glu Ile
1               5                   10                  15

Asp Asp Leu Pro Asn Leu Thr Asp Asn Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 282
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 282

Val Asp Ala Lys Tyr Ala Lys Glu Trp Gln Trp Ala Gly Val Glu Ile
1               5                   10                  15

Ala Glu Leu Pro Asn Leu Thr Gln Gln Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 283
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 283

Val Asp Ala Lys Tyr Ala Lys Glu His Ile Phe Ala Gly Trp Glu Ile
1               5                   10                  15

Thr Asp Leu Pro Asn Leu Thr Ser Ser Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 284
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 284

Val Asp Ala Lys Tyr Ala Lys Glu Trp Arg Trp Ala Gly Val Glu Ile
1               5                   10                  15

Gln Asp Leu Pro Asn Leu Thr Gln Gln Gln Arg Asp Ala Phe Ile Tyr
```

```
                    20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 285
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 285

Val Asp Ala Lys Tyr Ala Lys Glu Asn Ile Phe Ala Gly Trp Glu Ile
1               5                   10                  15

Ser Asp Leu Pro Asn Leu Thr Ile Phe Gln Arg His Ala Phe Ile Tyr
                20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 286
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 286

Val Asp Ala Lys Tyr Ala Lys Glu Trp Gln Trp Ala Gly Val Glu Ile
1               5                   10                  15

Gln Glu Leu Pro Asn Leu Thr Gln Gln Gln Arg His Ala Phe Ile Tyr
                20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 287
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 287

Val Asp Ala Lys Tyr Ala Lys Glu Asn Leu Phe Ala Gly Trp Glu Ile
1               5                   10                  15

Asp Asp Leu Pro Asn Leu Thr Ile Arg Gln Arg Asp Ala Phe Ile Tyr
                20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 288
<211> LENGTH: 58
<212> TYPE: PRT
<213> ORGANISM: ARTIFICIAL SEQUENCE
```

-continued

```
<220> FEATURE:
<223> OTHER INFORMATION: Engineered CAIX-binding polypeptide

<400> SEQUENCE: 288

Val Asp Ala Lys Tyr Ala Lys Glu Asn Tyr Phe Ala Gly Trp Glu Ile
1               5                   10                  15

Asp Asp Leu Pro Asn Leu Thr Glu Gln Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 289
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 289

Val Asp Ala Lys Tyr Ala Lys Glu Asn Leu Phe Ala Gly Trp Glu Ile
1               5                   10                  15

Ala Asp Leu Pro Asn Leu Thr Asp His Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 290
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 290

Val Asp Ala Lys Tyr Ala Lys Glu Trp Ser Trp Ala Ser Val Glu Ile
1               5                   10                  15

Ala Asp Leu Pro Asn Leu Thr Gln Arg Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 291
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 291

Val Asp Ala Lys Tyr Ala Lys Glu Asp Ile Phe Ala Gly Trp Glu Ile
1               5                   10                  15

Thr Asp Leu Pro Asn Leu Thr Asp His Gln Arg Asn Ala Phe Ile Tyr
            20                  25                  30

Lys Leu Trp Asp Asp Pro Ser Gln Ser Ser Glu Leu Leu Ser Glu Ala
        35                  40                  45
```

```
Lys Lys Leu Asn Asp Ser Gln Ala Pro Lys
    50                  55

<210> SEQ ID NO 292
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 292

Val Asp Ala Lys Tyr Ala Lys Glu Gln Leu Phe Ala Gly Trp Glu Ile
1               5                   10                  15

Asp Asp Leu Pro Asn Leu Thr Ile Asp Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 293
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 293

Val Asp Ala Lys Tyr Ala Lys Glu Asn Trp Phe Ala Gly Trp Glu Ile
1               5                   10                  15

Asp Asp Leu Pro Asn Leu Thr Glu Arg Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 294
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 294

Val Asp Ala Lys Tyr Ala Lys Glu His Leu Phe Ala Gly Trp Glu Ile
1               5                   10                  15

Asp Glu Leu Pro Asn Leu Thr Glu Gln Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 295
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 295
```

-continued

Val Asp Ala Lys Tyr Ala Lys Glu Asn Phe Trp Ala Gly Trp Glu Ile
1               5                   10                  15

Asp Asp Leu Pro Asn Leu Thr Glu Leu Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 296
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 296

Val Asp Ala Lys Tyr Ala Lys Glu His Leu Phe Ala Gly Trp Glu Ile
1               5                   10                  15

Glu Asp Leu Pro Asn Leu Thr Ile Asp Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 297
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 297

Val Asp Ala Lys Tyr Ala Lys Glu Asn Val Phe Ala Gly Trp Glu Ile
1               5                   10                  15

Asp Asp Leu Pro Asn Leu Thr Asp Gln Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 298
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 298

Val Asp Ala Lys Tyr Ala Lys Glu His Ile Phe Ala Gly Trp Glu Ile
1               5                   10                  15

Ala Asp Leu Pro Asn Leu Thr Asp Gly Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 299
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 299

```
Val Asp Ala Lys Tyr Ala Lys Glu Asn Ile Trp Ala Gly Trp Glu Ile
1               5                   10                  15

Ser Asp Leu Pro Asn Leu Thr Asp Thr Gln Arg Asn Ala Phe Ile Tyr
            20                  25                  30

Lys Leu Trp Asp Asp Pro Ser Gln Ser Glu Leu Leu Ser Glu Ala
        35                  40                  45

Lys Lys Leu Asn Asp Ser Gln Ala Pro Lys
    50                  55
```

<210> SEQ ID NO 300
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 300

```
Val Asp Ala Lys Tyr Ala Lys Glu Trp Gln Trp Ala Gly Ile Glu Ile
1               5                   10                  15

Gln Asp Leu Pro Asn Leu Thr Gln Arg Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 301
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 301

```
Val Asp Ala Lys Tyr Ala Lys Glu Trp Ile Phe Ala Gly Trp Glu Ile
1               5                   10                  15

Thr Asp Leu Pro Asn Leu Thr Asp Phe Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 302
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 302

```
Val Asp Ala Lys Tyr Ala Lys Glu Asn Trp Ala Ala Gly Trp Glu Ile
1               5                   10                  15
```

```
Asp Asp Leu Pro Asn Leu Thr Asp Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 303
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 303

Val Asp Ala Lys Tyr Ala Lys Glu His Leu Phe Ala Gly Trp Glu Ile
1               5                   10                  15

Asp Glu Leu Pro Asn Leu Thr Ala Tyr Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 304
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 304

Val Asp Ala Lys Tyr Ala Lys Glu His Ile Phe Ala Gly Trp Glu Ile
1               5                   10                  15

Glu Asp Leu Pro Asn Leu Thr Glu Ser Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 305
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 305

Val Asp Ala Lys Tyr Ala Lys Glu Asn Ile Phe Ala Gly Trp Glu Ile
1               5                   10                  15

Asp Asp Leu Pro Asn Leu Thr Ala His Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 306
<211> LENGTH: 58
<212> TYPE: PRT
```

```
<213> ORGANISM: ARTIFICIAL SEQUENCE
<220> FEATURE:
<223> OTHER INFORMATION: Engineered CAIX-binding polypeptide

<400> SEQUENCE: 306

Val Asp Ala Lys Tyr Ala Lys Glu Asn Leu Phe Ala Gly Trp Glu Ile
1               5                   10                  15

Gly Asp Leu Pro Asn Leu Thr Thr Gly Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 307
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 307

Val Asp Ala Lys Tyr Ala Lys Glu His Leu Phe Ala Gly Trp Glu Ile
1               5                   10                  15

Ser Asp Leu Pro Asn Leu Thr Ala Asn Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 308
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 308

Val Asp Ala Lys Tyr Ala Lys Glu Gln Leu Phe Ala Gly Trp Glu Ile
1               5                   10                  15

Asp Asp Leu Pro Asn Leu Thr Asp Gln Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 309
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 309

Val Asp Ala Lys Tyr Ala Lys Glu Trp Gln Trp Ala Gly Val Glu Ile
1               5                   10                  15

Asn Asp Leu Pro Asn Leu Thr Gln Arg Gln Arg Asp Ala Phe Ile Tyr
            20                  25                  30

Lys Leu Trp Asp Asp Pro Ser Gln Ser Ser Glu Leu Leu Ser Glu Ala
```

Lys Lys Leu Asn Asp Ser Gln Ala Pro Lys
    50              55

<210> SEQ ID NO 310
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 310

Val Asp Ala Lys Tyr Ala Lys Glu Trp Trp Tyr Ala Gly Val Glu Ile
1               5                   10                  15

Ala Asp Leu Pro Asn Leu Thr Gln Gln Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50              55

<210> SEQ ID NO 311
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 311

Val Asp Ala Lys Tyr Ala Lys Glu Gln Trp Trp Ala Gly Trp Glu Ile
1               5                   10                  15

Asp Asp Leu Pro Asn Leu Thr Glu Ile Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50              55

<210> SEQ ID NO 312
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 312

Val Asp Ala Lys Tyr Ala Lys Glu Trp Gln Trp Ala Gly Val Glu Ile
1               5                   10                  15

Asn Glu Leu Pro Asn Leu Thr Gln Arg Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50              55

<210> SEQ ID NO 313
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

```
<400> SEQUENCE: 313

Val Asp Ala Lys Tyr Ala Lys Glu Asn Ile Trp Ala Gly Trp Glu Ile
1               5                   10                  15

Ser Asp Leu Pro Asn Leu Thr Glu Asp Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 314
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 314

Val Asp Ala Lys Tyr Ala Lys Glu His Ile Phe Ala Gly Trp Glu Ile
1               5                   10                  15

Glu Glu Leu Pro Asn Leu Thr Asp Thr Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 315
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 315

Val Asp Ala Lys Tyr Ala Lys Glu Asp Leu Trp Ala Gly Trp Glu Ile
1               5                   10                  15

Thr Asp Leu Pro Asn Leu Thr Glu Trp Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 316
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 316

Val Asp Ala Lys Tyr Ala Lys Glu Asn Ile Phe Ala Gly Trp Glu Ile
1               5                   10                  15

Glu Asp Leu Pro Asn Leu Thr Asp Asn Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 317
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 317

Val Asp Ala Lys Tyr Ala Lys Glu Asn Leu Trp Ala Gly Trp Glu Ile
1               5                   10                  15

Asn Asp Leu Pro Asn Leu Thr Glu Gln Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 318
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 318

Val Asp Ala Lys Tyr Ala Lys Glu Asn Ile Trp Ala Gly Trp Glu Ile
1               5                   10                  15

Asp Asp Leu Pro Asn Leu Thr Val Asn Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 319
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 319

Val Asp Ala Lys Tyr Ala Lys Glu Gln Trp Trp Ala Gly Trp Glu Ile
1               5                   10                  15

Asp Asp Leu Pro Asn Leu Thr Glu Asp Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 320
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 320

Val Asp Ala Lys Tyr Ala Lys Glu His Thr Asn Ala Trp Ala Glu Ile
1               5                   10                  15

His Arg Leu Pro Asn Leu Thr Glu Ser Gln Gln Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 321
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 321

Val Asp Ala Lys Tyr Ala Lys Glu Trp Trp Tyr Ala Gly Glu Glu Ile
1               5                   10                  15

Ala Asp Leu Pro Asn Leu Thr Gln Gln Gln Gln Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 322
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 322

Val Asp Ala Lys Tyr Ala Lys Glu Trp Gln Trp Ala Gly Val Glu Ile
1               5                   10                  15

Asn Glu Leu Pro Asn Leu Thr Trp Gln Gln Arg Gln Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 323
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 323

Val Asp Ala Lys Tyr Ala Lys Glu Trp Gln Trp Ala Gly Val Glu Ile
1               5                   10                  15

Asn Asp Leu Pro Asn Leu Thr Gln Gln Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 324
<211> LENGTH: 58

```
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 324

Val Asp Ala Lys Tyr Ala Lys Glu Trp Arg Trp Ala Gly Val Glu Ile
1               5                   10                  15

Ala Glu Leu Pro Asn Leu Thr Gln Asn Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 325
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 325

Val Asp Ala Lys Tyr Ala Lys Glu His Leu Phe Ala Gly Trp Glu Ile
1               5                   10                  15

Gly Asp Leu Pro Asn Leu Thr Glu Gln Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 326
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 326

Val Asp Ala Lys Tyr Ala Lys Glu Asn Leu Phe Ala Gly Trp Glu Ile
1               5                   10                  15

His Asp Leu Pro Asn Leu Thr Asp Asp Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 327
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 327

Val Asp Ala Lys Tyr Ala Lys Glu Asn Leu Phe Ala Gly Trp Glu Ile
1               5                   10                  15

Asp Asp Leu Pro Asn Leu Thr Glu Val Gln Arg Asn Ala Phe Ile Tyr
            20                  25                  30
```

```
Lys Leu Trp Asp Asp Pro Ser Gln Ser Ser Glu Leu Leu Ser Glu Ala
        35                  40                  45
Lys Lys Leu Asn Asp Ser Gln Ala Pro Lys
    50                  55

<210> SEQ ID NO 328
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 328

Val Asp Ala Lys Tyr Ala Lys Glu Asn Leu Phe Ala Gly Trp Glu Ile
1               5                   10                  15
Thr Asp Leu Pro Asn Leu Thr Ala Ser Gln Arg His Ala Phe Ile Tyr
            20                  25                  30
Lys Leu Trp Asp Asp Pro Ser Gln Ser Ser Glu Leu Leu Ser Glu Ala
        35                  40                  45
Lys Lys Leu Asn Asp Ser Gln Ala Pro Lys
    50                  55

<210> SEQ ID NO 329
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 329

Val Asp Ala Lys Tyr Ala Lys Glu Trp Trp Trp Ala Ala Gly Glu Ile
1               5                   10                  15
Ser Asp Leu Pro Asn Leu Thr Gly Gln Gln Arg Asp Ala Phe Ile Tyr
            20                  25                  30
Lys Leu Trp Asp Asp Pro Ser Gln Ser Ser Glu Leu Leu Ser Glu Ala
        35                  40                  45
Lys Lys Leu Asn Asp Ser Gln Ala Pro Lys
    50                  55

<210> SEQ ID NO 330
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 330

Val Asp Ala Lys Tyr Ala Lys Glu Asn Ile Phe Ala Gly Trp Glu Ile
1               5                   10                  15
Val Asp Leu Pro Asn Leu Thr Glu Ile Gln Arg Asn Ala Phe Ile Tyr
            20                  25                  30
Lys Leu Trp Asp Asp Pro Ser Gln Ser Ser Glu Leu Leu Ser Glu Ala
        35                  40                  45
Lys Lys Leu Asn Asp Ser Gln Ala Pro Lys
    50                  55

<210> SEQ ID NO 331
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide
```

<400> SEQUENCE: 331

Val Asp Ala Lys Tyr Ala Lys Glu Asn Leu Phe Ala Gly Trp Glu Ile
1               5                   10                  15

Arg Asp Leu Pro Asn Leu Thr Glu Ala Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 332
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 332

Val Asp Ala Lys Tyr Ala Lys Glu Asn Trp Trp Ala Gly Trp Glu Ile
1               5                   10                  15

Thr Asp Leu Pro Asn Leu Thr Glu His Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 333
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 333

Val Asp Ala Lys Tyr Ala Lys Glu His Leu Phe Ala Gly Trp Glu Ile
1               5                   10                  15

Gln Asp Leu Pro Asn Leu Thr Glu Asp Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 334
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 334

Val Asp Ala Lys Tyr Ala Lys Glu Asn Ile Trp Ala Gly Trp Glu Ile
1               5                   10                  15

Gly Asp Leu Pro Asn Leu Thr Glu Gln Gln Arg His Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys

<210> SEQ ID NO 335
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 335

Val Asp Ala Lys Tyr Ala Lys Glu Trp Gln Trp Ala Gly Val Glu Ile
1               5                   10                  15

Gln Asp Leu Pro Asn Leu Thr Gly Gln Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 336
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 336

Val Asp Ala Lys Tyr Ala Lys Glu Gln Ile Phe Ala Gly Trp Glu Ile
1               5                   10                  15

Thr Asp Leu Pro Asn Leu Thr Glu Ala Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 337
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 337

Val Asp Ala Lys Tyr Ala Lys Glu Asn Ile Trp Ala Gly Trp Glu Ile
1               5                   10                  15

Gly Asp Leu Pro Asn Leu Thr Asp Gln Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 338
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 338

Val Asp Ala Lys Tyr Ala Lys Glu Trp Ser Trp Ala Ser Val Glu Ile

```
                1               5                   10                  15
            Ala Asp Leu Pro Asn Leu Thr Gln Gln Gln Arg Asp Ala Phe Ile Tyr
                                20                  25                  30

Lys Leu Trp Asp Asp Pro Ser Gln Ser Ser Glu Leu Leu Ser Glu Ala
                        35                  40                  45

Lys Lys Leu Asn Asp Ser Gln Ala Pro Lys
                    50                  55

<210> SEQ ID NO 339
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 339

Val Asp Ala Lys Tyr Ala Lys Glu Asn Ile Phe Ala Gly Trp Glu Ile
1               5                   10                  15

Glu Asp Leu Pro Asn Leu Thr Val His Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 340
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 340

Glu Asn Leu Trp Ala Gly Trp Glu Ile Asp Asp Leu Pro Asn Leu Thr
1               5                   10                  15

His Ser Gln Arg Asn Ala Phe Ile Tyr Lys Leu Trp Asp
            20                  25

<210> SEQ ID NO 341
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 341

Glu Asp Val Asn Ala Trp Gln Glu Ile Ile Lys Leu Pro Asn Leu Thr
1               5                   10                  15

Ile Phe Gln Arg Asp Ala Phe Ile Tyr Lys Leu Trp Asp
            20                  25

<210> SEQ ID NO 342
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 342

Glu Trp Lys Phe Ala Ser Ile Glu Ile Ala Asp Leu Pro Asn Leu Thr
1               5                   10                  15

Gln His Gln Lys Asp Ala Phe Ile Phe Lys Leu Trp Asp
```

-continued

```
                20                  25

<210> SEQ ID NO 343
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 343

Glu His Glu Trp Ala Gly Val Glu Ile Gln Ser Leu Pro Asn Leu Thr
1               5                   10                  15

Thr Gln Gln Lys His Ala Phe Ile Tyr Lys Leu Trp Asp
            20                  25

<210> SEQ ID NO 344
<211> LENGTH: 29
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 344

Glu Asp Arg Tyr Ala Trp Thr Glu Ile His Lys Leu Pro Asn Leu Thr
1               5                   10                  15

Val Arg Gln Gln Asn Ala Phe Ile Tyr Lys Leu Trp Asp
            20                  25

<210> SEQ ID NO 345
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 345

Lys Glu Asn Leu Trp Ala Gly Trp Glu Ile Asp Asp Leu Pro Asn Leu
1               5                   10                  15

Thr His Ser Gln Arg Asn Ala Phe Ile Tyr Lys Leu Trp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 346
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 346

Lys Glu Asp Val Asn Ala Trp Gln Glu Ile Ile Lys Leu Pro Asn Leu
1               5                   10                  15

Thr Ile Phe Gln Arg Asp Ala Phe Ile Tyr Lys Leu Trp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 347
<211> LENGTH: 49
```

```
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 347

Lys Glu Trp Lys Phe Ala Ser Ile Glu Ile Ala Asp Leu Pro Asn Leu
1               5                   10                  15

Thr Gln His Gln Lys Asp Ala Phe Ile Phe Lys Leu Trp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 348
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 348

Lys Glu His Glu Trp Ala Gly Val Glu Ile Gln Ser Leu Pro Asn Leu
1               5                   10                  15

Thr Thr Gln Gln Lys His Ala Phe Ile Tyr Lys Leu Trp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 349
<211> LENGTH: 49
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 349

Lys Glu Asp Arg Tyr Ala Trp Thr Glu Ile His Lys Leu Pro Asn Leu
1               5                   10                  15

Thr Val Arg Gln Gln Asn Ala Phe Ile Tyr Lys Leu Trp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 350
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 350

Val Asp Ala Lys Tyr Ala Lys Glu Asn Leu Trp Ala Gly Trp Glu Ile
1               5                   10                  15

Asp Asp Leu Pro Asn Leu Thr His Ser Gln Arg Asn Ala Phe Ile Tyr
            20                  25                  30

Lys Leu Trp Asp Asp Pro Ser Gln Ser Ser Glu Leu Leu Ala Glu Ala
        35                  40                  45
```

-continued

Lys Lys Leu Asn Asp Ala Gln Ala Pro Lys
    50                  55

<210> SEQ ID NO 351
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 351

Val Asp Ala Lys Tyr Ala Lys Glu Asp Val Asn Ala Trp Gln Glu Ile
1               5                   10                  15

Ile Lys Leu Pro Asn Leu Thr Ile Phe Gln Arg Asp Ala Phe Ile Tyr
            20                  25                  30

Lys Leu Trp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 352
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 352

Val Asp Ala Lys Tyr Ala Lys Glu Trp Lys Phe Ala Ser Ile Glu Ile
1               5                   10                  15

Ala Asp Leu Pro Asn Leu Thr Gln His Gln Lys Asp Ala Phe Ile Phe
            20                  25                  30

Lys Leu Trp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 353
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 353

Val Asp Ala Lys Tyr Ala Lys Glu His Glu Trp Ala Gly Val Glu Ile
1               5                   10                  15

Gln Ser Leu Pro Asn Leu Thr Thr Gln Gln Lys His Ala Phe Ile Tyr
            20                  25                  30

Lys Leu Trp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 354
<211> LENGTH: 58
<212> TYPE: PRT
<213> ORGANISM: ARTIFICIAL SEQUENCE
<220> FEATURE:
<223> OTHER INFORMATION: Engineered CAIX-binding polypeptide

<400> SEQUENCE: 354

-continued

Val Asp Ala Lys Tyr Ala Lys Glu Asp Arg Tyr Ala Trp Thr Glu Ile
1               5                   10                  15

His Lys Leu Pro Asn Leu Thr Val Arg Gln Gln Asn Ala Phe Ile Tyr
            20                  25                  30

Lys Leu Trp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 355
<211> LENGTH: 58
<212> TYPE: PRT
<213> ORGANISM: ARTIFICIAL SEQUENCE
<220> FEATURE:
<223> OTHER INFORMATION: Engineered Taq polymerase binding polypeptide

<400> SEQUENCE: 355

Val Asp Asn Lys Phe Asn Lys Glu Leu Gly Trp Ala Thr Trp Glu Ile
1               5                   10                  15

Phe Asn Leu Pro Asn Leu Asn Gly Val Gln Val Lys Ala Phe Ile Asp
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 356
<211> LENGTH: 58
<212> TYPE: PRT
<213> ORGANISM: ARTIFICIAL SEQUENCE
<220> FEATURE:
<223> OTHER INFORMATION: Engineered polypeptide used as negative control

<400> SEQUENCE: 356

Ala Glu Ala Lys Tyr Ala Lys Glu Leu Gly Trp Ala Thr Trp Glu Ile
1               5                   10                  15

Phe Asn Leu Pro Asn Leu Thr Gly Val Gln Val Lys Ala Phe Ile Asp
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 357
<211> LENGTH: 58
<212> TYPE: PRT
<213> ORGANISM: ARTIFICIAL SEQUENCE
<220> FEATURE:
<223> OTHER INFORMATION: Engineered polypeptide used as negative control

<400> SEQUENCE: 357

Val Asp Asn Lys Phe Asn Lys Glu Leu Gly Trp Ala Thr Trp Glu Ile
1               5                   10                  15

Phe Asn Leu Pro Asn Leu Asn Gly Val Gln Val Lys Ala Phe Ile Asp
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 358
<211> LENGTH: 58
<212> TYPE: PRT
<213> ORGANISM: ARTIFICIAL SEQUENCE
<220> FEATURE:
<223> OTHER INFORMATION: Engineered CAIX binding polypeptide

<400> SEQUENCE: 358

Val Asp Ala Lys Tyr Ala Lys Glu Trp Lys Phe Ala Ser Ile Glu Ile
1               5                   10                  15

Ala Asp Leu Pro Asn Leu Thr Gln His Gln Lys Asp Ala Phe Ile Phe
            20                  25                  30

Lys Leu Trp Asp Asp Pro Ser Gln Ser Ser Glu Leu Leu Ala Glu Ala
        35                  40                  45

Lys Lys Leu Asn Asp Ser Gln Ala Pro Lys
    50                  55

<210> SEQ ID NO 359
<211> LENGTH: 58
<212> TYPE: PRT
<213> ORGANISM: ARTIFICIAL SEQUENCE
<220> FEATURE:
<223> OTHER INFORMATION: Engineered polypeptide with affinity for Z03639

<400> SEQUENCE: 359

Val Asp Asn Lys Phe Asn Lys Glu Arg Val Ile Ala Ile Gly Glu Ile
1               5                   10                  15

Met Arg Leu Pro Asn Leu Asn Ser Leu Gln Val Val Ala Phe Ile Asn
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 360
<211> LENGTH: 356
<212> TYPE: PRT
<213> ORGANISM: Homo sapiens

<400> SEQUENCE: 360

Pro Leu Gly Glu Glu Asp Leu Pro Ser Glu Glu Asp Ser Pro Arg Glu
1               5                   10                  15

Glu Asp Pro Pro Gly Glu Glu Asp Leu Pro Gly Glu Glu Asp Leu Pro
            20                  25                  30

Gly Glu Glu Asp Leu Pro Glu Val Lys Pro Lys Ser Glu Glu Glu Gly
        35                  40                  45

Ser Leu Lys Leu Glu Asp Leu Pro Thr Val Glu Ala Pro Gly Asp Pro
    50                  55                  60

Gln Glu Pro Gln Asn Asn Ala His Arg Asp Lys Glu Gly Asp Asp Gln
65                  70                  75                  80

Ser His Trp Arg Tyr Gly Gly Asp Pro Pro Trp Pro Arg Val Ser Pro
                85                  90                  95

Ala Cys Ala Gly Arg Phe Gln Ser Pro Val Asp Ile Arg Pro Gln Leu
            100                 105                 110

Ala Ala Phe Cys Pro Ala Leu Arg Pro Leu Glu Leu Leu Gly Phe Gln
        115                 120                 125

Leu Pro Pro Leu Pro Glu Leu Arg Leu Arg Asn Asn Gly His Ser Val
    130                 135                 140

Gln Leu Thr Leu Pro Pro Gly Leu Glu Met Ala Leu Gly Pro Gly Arg
```

```
                145                 150                 155                 160
        Glu Tyr Arg Ala Leu Gln Leu His Leu His Trp Gly Ala Ala Gly Arg
                    165                 170                 175

Pro Gly Ser Glu His Thr Val Glu Gly His Arg Phe Pro Ala Glu Ile
                    180                 185                 190

His Val Val His Leu Ser Thr Ala Phe Ala Arg Val Asp Glu Ala Leu
                    195                 200                 205

Gly Arg Pro Gly Gly Leu Ala Val Leu Ala Ala Phe Leu Glu Glu Gly
                    210                 215                 220

Pro Glu Glu Asn Ser Ala Tyr Glu Gln Leu Leu Ser Arg Leu Glu Glu
        225                 230                 235                 240

Ile Ala Glu Glu Gly Ser Glu Thr Gln Val Pro Gly Leu Asp Ile Ser
                            245                 250                 255

Ala Leu Leu Pro Ser Asp Phe Ser Arg Tyr Phe Gln Tyr Glu Gly Ser
                        260                 265                 270

Leu Thr Thr Pro Pro Cys Ala Gln Gly Val Ile Trp Thr Val Phe Asn
                    275                 280                 285

Gln Thr Val Met Leu Ser Ala Lys Gln Leu His Thr Leu Ser Asp Thr
                290                 295                 300

Leu Trp Gly Pro Gly Asp Ser Arg Leu Gln Leu Asn Phe Arg Ala Thr
        305                 310                 315                 320

Gln Pro Leu Asn Gly Arg Val Ile Glu Ala Ser Phe Pro Ala Gly Val
                            325                 330                 335

Asp Ser Ser Pro Arg Ala Ala Glu Pro Val Gln Leu Asn Ser Cys Leu
                        340                 345                 350

Ala Ala Gly Asp
                355

<210> SEQ ID NO 361
<211> LENGTH: 24
<212> TYPE: DNA
<213> ORGANISM: ARTIFICIAL SEQUENCE
<220> FEATURE:
<223> OTHER INFORMATION: Engineered primer

<400> SEQUENCE: 361
tgcttccggc tcgtatgttg tgtg                                          24

<210> SEQ ID NO 362
<211> LENGTH: 21
<212> TYPE: DNA
<213> ORGANISM: ARTIFICIAL SEQUENCE
<220> FEATURE:
<223> OTHER INFORMATION: Engineered primer

<400> SEQUENCE: 362
cggaaccaga gccaccaccg g                                             21

<210> SEQ ID NO 363
<211> LENGTH: 21
<212> TYPE: DNA
<213> ORGANISM: ARTIFICIAL SEQUENCE
<220> FEATURE:
<223> OTHER INFORMATION: Engineered primer
<220> FEATURE:
<221> NAME/KEY: misc_feature
<222> LOCATION: (1)..(1)
<223> OTHER INFORMATION: Biotin

<400> SEQUENCE: 363
```
cggaaccaga gccaccaccg g    21

<210> SEQ ID NO 364
<211> LENGTH: 147
<212> TYPE: DNA
<213> ORGANISM: ARTIFICIAL SEQUENCE
<220> FEATURE:
<223> OTHER INFORMATION: Engineered library oligonucleotide
<220> FEATURE:
<221> NAME/KEY: misc_feature
<222> LOCATION: (39)..(47)
<223> OTHER INFORMATION: n is a, c, g, or t
<220> FEATURE:
<221> NAME/KEY: misc_feature
<222> LOCATION: (51)..(56)
<223> OTHER INFORMATION: n is a, c, g, or t
<220> FEATURE:
<221> NAME/KEY: misc_feature
<222> LOCATION: (63)..(68)
<223> OTHER INFORMATION: n is a, c, g, or t
<220> FEATURE:
<221> NAME/KEY: misc_feature
<222> LOCATION: (84)..(89)
<223> OTHER INFORMATION: n is a, c, g, or t
<220> FEATURE:
<221> NAME/KEY: misc_feature
<222> LOCATION: (93)..(98)
<223> OTHER INFORMATION: n is a, c, g, or t
<220> FEATURE:
<221> NAME/KEY: misc_feature
<222> LOCATION: (108)..(110)
<223> OTHER INFORMATION: n is a, c, g, or t

<400> SEQUENCE: 364
aaataaatct cgaggtagat gccaaatacg ccaaagarnn nnnnnngcr nnnnnngara    60 tynnnnnnyt rcctaactta acsnnnnnnc arnnnnnngc mttcatcnnn aaattatggg   120
atgacccaag ccagagctca ttattta    147

<210> SEQ ID NO 365
<211> LENGTH: 58
<212> TYPE: PRT
<213> ORGANISM: ARTIFICIAL SEQUENCE
<220> FEATURE:
<223> OTHER INFORMATION: Engineered CAIX binding polypeptide

<400> SEQUENCE: 365

Ala Glu Ala Lys Tyr Ala Lys Glu Asn Leu Phe Ala Gly Trp Glu Ile
1               5                   10                  15

Asp Asp Leu Pro Asn Leu Thr Glu Asp Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 366
<211> LENGTH: 58
<212> TYPE: PRT
<213> ORGANISM: ARTIFICIAL SEQUENCE
<220> FEATURE:
<223> OTHER INFORMATION: Engineered CAIX binding polypeptide

<400> SEQUENCE: 366

Ala Glu Ala Lys Tyr Ala Lys Glu Asn Leu Phe Ala Gly Trp Glu Ile
1               5                   10                  15

Ser Asp Leu Pro Asn Leu Thr Asp Tyr Gln Arg Asn Ala Phe Ile Tyr
            20                  25                  30

```
Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 367
<211> LENGTH: 58
<212> TYPE: PRT
<213> ORGANISM: ARTIFICIAL SEQUENCE
<220> FEATURE:
<223> OTHER INFORMATION: Engineered CAIX binding polypeptide

<400> SEQUENCE: 367

Ala Glu Ala Lys Tyr Ala Lys Glu Asn Ile Phe Ala Gly Trp Glu Ile
1               5                   10                  15

Asp Asp Leu Pro Asn Leu Thr Asp Glu Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 368
<211> LENGTH: 58
<212> TYPE: PRT
<213> ORGANISM: ARTIFICIAL SEQUENCE
<220> FEATURE:
<223> OTHER INFORMATION: Engineered CAIX binding polypeptide

<400> SEQUENCE: 368

Ala Glu Ala Lys Tyr Ala Lys Glu Trp Trp Trp Ala Gly Ile Glu Ile
1               5                   10                  15

Ala Asp Leu Pro Asn Leu Thr Gln Gln Gln Arg Asp Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 369
<211> LENGTH: 29
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (2)..(2)
<223> OTHER INFORMATION: Xaa is selected from D, H, N, Q and W
<220> FEATURE:
<221> NAME/KEY: MISC_FEATURE
<222> LOCATION: (3)..(3)
<223> OTHER INFORMATION: Xaa is selected from E, F, I, K, L, Q, R, S, T,
      V, W and Y
<220> FEATURE:
<221> NAME/KEY: MISC_FEATURE
<222> LOCATION: (4)..(4)
<223> OTHER INFORMATION: Xaa is selected from A, F, N, W and Y
<220> FEATURE:
<221> NAME/KEY: MISC_FEATURE
<222> LOCATION: (6)..(6)
<223> OTHER INFORMATION: Xaa is selected from A, G, S and W
<220> FEATURE:
<221> NAME/KEY: MISC_FEATURE
<222> LOCATION: (7)..(7)
<223> OTHER INFORMATION: Xaa is selected from A, E, G, I, Q, T, V and W
```

```
<220> FEATURE:
<221> NAME/KEY: MISC_FEATURE
<222> LOCATION: (10)..(10)
<223> OTHER INFORMATION: Xaa is selected from A, D, E, G, H, I, N, Q, R,
      S, T and V
<220> FEATURE:
<221> NAME/KEY: MISC_FEATURE
<222> LOCATION: (11)..(11)
<223> OTHER INFORMATION: Xaa is selected from D, E, K, R and S
<220> FEATURE:
<221> NAME/KEY: MISC_FEATURE
<222> LOCATION: (16)..(16)
<223> OTHER INFORMATION: Xaa is selected from N and T
<220> FEATURE:
<221> NAME/KEY: MISC_FEATURE
<222> LOCATION: (17)..(17)
<223> OTHER INFORMATION: Xaa is selected from A, D, E, G, H, I, Q, S, T,
      V and W
<220> FEATURE:
<221> NAME/KEY: MISC_FEATURE
<222> LOCATION: (18)..(18)
<223> OTHER INFORMATION: Xaa is selected from A, D, E, F, G, H, I, L, N,
      Q, R, S, T, V, W and Y
<220> FEATURE:
<221> NAME/KEY: MISC_FEATURE
<222> LOCATION: (20)..(20)
<223> OTHER INFORMATION: Xaa is selected from K, Q and R
<220> FEATURE:
<221> NAME/KEY: MISC_FEATURE
<222> LOCATION: (21)..(21)
<223> OTHER INFORMATION: Xaa is selected from D, H, N and Q
<220> FEATURE:
<221> NAME/KEY: MISC_FEATURE
<222> LOCATION: (25)..(25)
<223> OTHER INFORMATION: Xaa is selected from F and Y
<220> FEATURE:
<221> NAME/KEY: MISC_FEATURE
<222> LOCATION: (26)..(26)
<223> OTHER INFORMATION: Xaa is selected from K and S

<400> SEQUENCE: 369

Glu Xaa Xaa Xaa Ala Xaa Xaa Glu Ile Xaa Xaa Leu Pro Asn Leu Xaa
1               5                   10                  15

Xaa Xaa Gln Xaa Xaa Ala Phe Ile Xaa Xaa Leu Trp Asp
            20                  25

<210> SEQ ID NO 370
<211> LENGTH: 29
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (2)..(2)
<223> OTHER INFORMATION: Xaa is selected from D, H, N, Q and W
<220> FEATURE:
<221> NAME/KEY: MISC_FEATURE
<222> LOCATION: (3)..(3)
<223> OTHER INFORMATION: Xaa is selected from F, I, L, Q, R, S, T, V, W
      and Y
<220> FEATURE:
<221> NAME/KEY: MISC_FEATURE
<222> LOCATION: (4)..(4)
<223> OTHER INFORMATION: Xaa is selected from A, F, N, W and Y
<220> FEATURE:
<221> NAME/KEY: MISC_FEATURE
<222> LOCATION: (6)..(6)
<223> OTHER INFORMATION: Xaa is selected from A, G, S and W
<220> FEATURE:
<221> NAME/KEY: MISC_FEATURE
<222> LOCATION: (7)..(7)
<223> OTHER INFORMATION: Xaa is selected from A, E, G, I, V and W
<220> FEATURE:
<221> NAME/KEY: MISC_FEATURE
<222> LOCATION: (10)..(10)
```

```
<223> OTHER INFORMATION: Xaa is selected from A, D, E, G, H, N, Q, R, S,
      T and V
<220> FEATURE:
<221> NAME/KEY: MISC_FEATURE
<222> LOCATION: (11)..(11)
<223> OTHER INFORMATION: Xaa is selected from D, E, R and S
<220> FEATURE:
<221> NAME/KEY: MISC_FEATURE
<222> LOCATION: (16)..(16)
<223> OTHER INFORMATION: Xaa is selected from N and T
<220> FEATURE:
<221> NAME/KEY: MISC_FEATURE
<222> LOCATION: (17)..(17)
<223> OTHER INFORMATION: Xaa is selected from A, D, E, G, I, Q, S, T, V
      and W
<220> FEATURE:
<221> NAME/KEY: MISC_FEATURE
<222> LOCATION: (18)..(18)
<223> OTHER INFORMATION: Xaa is selected from A, D, E, F, G, H, I, L, N,
      Q, R, S, T, V, W and Y
<220> FEATURE:
<221> NAME/KEY: MISC_FEATURE
<222> LOCATION: (20)..(20)
<223> OTHER INFORMATION: Xaa is selected from Q and R
<220> FEATURE:
<221> NAME/KEY: MISC_FEATURE
<222> LOCATION: (21)..(21)
<223> OTHER INFORMATION: Xaa is selected from D, H, N and Q
<220> FEATURE:
<221> NAME/KEY: MISC_FEATURE
<222> LOCATION: (26)..(26)
<223> OTHER INFORMATION: Xaa is selected from K and S

<400> SEQUENCE: 370

Glu Xaa Xaa Xaa Ala Xaa Xaa Glu Ile Xaa Xaa Leu Pro Asn Leu Xaa
1               5                   10                  15

Xaa Xaa Gln Xaa Xaa Ala Phe Ile Tyr Xaa Leu Trp Asp
            20                  25

<210> SEQ ID NO 371
<211> LENGTH: 20
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (1)..(2)
<223> OTHER INFORMATION: BM is a CAIX binding motif
<220> FEATURE:
<221> NAME/KEY: MISC_FEATURE
<222> LOCATION: (7)..(7)
<223> OTHER INFORMATION: Xaa is selected from A and S
<220> FEATURE:
<221> NAME/KEY: MISC_FEATURE
<222> LOCATION: (8)..(8)
<223> OTHER INFORMATION: Xaa is selected from N and E
<220> FEATURE:
<221> NAME/KEY: MISC_FEATURE
<222> LOCATION: (11)..(11)
<223> OTHER INFORMATION: Xaa is selected from A, S and C
<220> FEATURE:
<221> NAME/KEY: MISC_FEATURE
<222> LOCATION: (19)..(19)
<223> OTHER INFORMATION: Xaa is selected from A and S

<400> SEQUENCE: 371

Lys Asp Pro Ser Gln Ser Xaa Xaa Leu Leu Xaa Glu Ala Lys Lys Leu
1               5                   10                  15

Asn Asp Xaa Gln
            20

<210> SEQ ID NO 372
```

```
<211> LENGTH: 24
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (3)..(4)
<223> OTHER INFORMATION: BM is a CAIX binding motif
<220> FEATURE:
<221> NAME/KEY: MISC_FEATURE
<222> LOCATION: (13)..(13)
<223> OTHER INFORMATION: Xaa is selected from S and C

<400> SEQUENCE: 372

Tyr Ala Lys Asp Pro Ser Gln Ser Ser Glu Leu Leu Xaa Glu Ala Lys
1               5                   10                  15

Lys Leu Asn Asp Ser Gln Ala Pro
            20

<210> SEQ ID NO 373
<211> LENGTH: 24
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (3)..(4)
<223> OTHER INFORMATION: BM is a CAIX binding motif
<220> FEATURE:
<221> NAME/KEY: MISC_FEATURE
<222> LOCATION: (13)..(13)
<223> OTHER INFORMATION: Xaa is selected from A and C

<400> SEQUENCE: 373

Phe Asn Lys Asp Pro Ser Gln Ser Ala Asn Leu Leu Xaa Glu Ala Lys
1               5                   10                  15

Lys Leu Asn Asp Ala Gln Ala Pro
            20

<210> SEQ ID NO 374
<211> LENGTH: 29
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (7)..(8)
<223> OTHER INFORMATION: BM is a CAIX binding motif

<400> SEQUENCE: 374

Ala Asp Asn Asn Phe Asn Lys Asp Pro Ser Gln Ser Ala Asn Leu Leu
1               5                   10                  15

Ser Glu Ala Lys Lys Leu Asn Glu Ser Gln Ala Pro Lys
            20                  25

<210> SEQ ID NO 375
<211> LENGTH: 29
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (7)..(8)
<223> OTHER INFORMATION: BM is a CAIX binding motif

<400> SEQUENCE: 375
```

```
Ala Asp Asn Lys Phe Asn Lys Asp Pro Ser Gln Ser Ala Asn Leu Leu
1               5                   10                  15

Ala Glu Ala Lys Lys Leu Asn Asp Ala Gln Ala Pro Lys
                20                  25

<210> SEQ ID NO 376
<211> LENGTH: 29
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (7)..(8)
<223> OTHER INFORMATION: BM is a CAIX binding motif

<400> SEQUENCE: 376

Ala Asp Asn Lys Phe Asn Lys Asp Pro Ser Val Ser Lys Glu Ile Leu
1               5                   10                  15

Ala Glu Ala Lys Lys Leu Asn Asp Ala Gln Ala Pro Lys
                20                  25

<210> SEQ ID NO 377
<211> LENGTH: 32
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (10)..(11)
<223> OTHER INFORMATION: BM is a CAIX binding motif

<400> SEQUENCE: 377

Ala Asp Ala Gln Gln Asn Asn Phe Asn Lys Asp Pro Ser Gln Ser Thr
1               5                   10                  15

Asn Val Leu Gly Glu Ala Lys Lys Leu Asn Glu Ser Gln Ala Pro Lys
                20                  25                  30

<210> SEQ ID NO 378
<211> LENGTH: 27
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (5)..(6)
<223> OTHER INFORMATION: BM is a CAIX binding motif

<400> SEQUENCE: 378

Ala Gln His Asp Glu Asp Pro Ser Gln Ser Ala Asn Val Leu Gly Glu
1               5                   10                  15

Ala Gln Lys Leu Asn Asp Ser Gln Ala Pro Lys
                20                  25

<210> SEQ ID NO 379
<211> LENGTH: 29
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (7)..(8)
<223> OTHER INFORMATION: BM is a CAIX binding motif
```

-continued

```
<400> SEQUENCE: 379

Val Asp Asn Lys Phe Asn Lys Asp Pro Ser Gln Ser Ala Asn Leu Leu
1               5                   10                  15

Ala Glu Ala Lys Lys Leu Asn Asp Ala Gln Ala Pro Lys
            20                  25

<210> SEQ ID NO 380
<211> LENGTH: 29
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (7)..(8)
<223> OTHER INFORMATION: BM is a CAIX binding motif

<400> SEQUENCE: 380

Ala Glu Ala Lys Tyr Ala Lys Asp Pro Ser Glu Ser Ser Glu Leu Leu
1               5                   10                  15

Ser Glu Ala Lys Lys Leu Asn Lys Ser Gln Ala Pro Lys
            20                  25

<210> SEQ ID NO 381
<211> LENGTH: 29
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (7)..(8)
<223> OTHER INFORMATION: BM is a CAIX binding motif

<400> SEQUENCE: 381

Val Asp Ala Lys Tyr Ala Lys Asp Pro Ser Gln Ser Glu Leu Leu
1               5                   10                  15

Ala Glu Ala Lys Lys Leu Asn Asp Ala Gln Ala Pro Lys
            20                  25

<210> SEQ ID NO 382
<211> LENGTH: 29
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (7)..(8)
<223> OTHER INFORMATION: BM is a CAIX binding motif

<400> SEQUENCE: 382

Val Asp Ala Lys Tyr Ala Lys Asp Pro Ser Gln Ser Ser Glu Leu Leu
1               5                   10                  15

Ala Glu Ala Lys Lys Leu Asn Asp Ser Gln Ala Pro Lys
            20                  25

<210> SEQ ID NO 383
<211> LENGTH: 29
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (7)..(8)
<223> OTHER INFORMATION: BM is a CAIX binding motif
```

<400> SEQUENCE: 383

Ala Glu Ala Lys Tyr Ala Lys Asp Pro Ser Gln Ser Ser Glu Leu Leu
1               5                   10                  15

Ser Glu Ala Lys Lys Leu Asn Asp Ser Gln Ala Pro Lys
            20                  25

<210> SEQ ID NO 384
<211> LENGTH: 29
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (7)..(8)
<223> OTHER INFORMATION: BM is a CAIX binding motif

<400> SEQUENCE: 384

Val Asp Ala Lys Tyr Ala Lys Asp Pro Ser Gln Ser Ser Glu Leu Leu
1               5                   10                  15

Ser Glu Ala Lys Lys Leu Asn Asp Ser Gln Ala Pro Lys
            20                  25

<210> SEQ ID NO 385
<211> LENGTH: 29
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (7)..(8)
<223> OTHER INFORMATION: BM is a CAIX binding motif

<400> SEQUENCE: 385

Val Asp Ala Lys Tyr Ala Lys Asp Pro Ser Gln Ser Ser Glu Leu Leu
1               5                   10                  15

Ala Glu Ala Lys Lys Leu Asn Lys Ala Gln Ala Pro Lys
            20                  25

<210> SEQ ID NO 386
<211> LENGTH: 29
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (7)..(8)
<223> OTHER INFORMATION: BM is a CAIX binding motif

<400> SEQUENCE: 386

Ala Glu Ala Lys Tyr Ala Lys Asp Pro Ser Gln Ser Ser Glu Leu Leu
1               5                   10                  15

Ala Glu Ala Lys Lys Leu Asn Lys Ala Gln Ala Pro Lys
            20                  25

<210> SEQ ID NO 387
<211> LENGTH: 16
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (8)..(9)
<223> OTHER INFORMATION: Individual Z variant

```
<220> FEATURE:
<221> NAME/KEY: MISC_FEATURE
<222> LOCATION: (12)..(13)
<223> OTHER INFORMATION: Individual Z variant is Z 03639

<400> SEQUENCE: 387

Ala Gln His Asp Glu Ala Leu Glu Val Asp Tyr Val Tyr Val Pro Gly
1               5                   10                  15

<210> SEQ ID NO 388
<211> LENGTH: 15
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (12)..(13)
<223> OTHER INFORMATION: 2 Consecutive Individual Z Variants

<400> SEQUENCE: 388

Met Gly Ser Ser His His His His His His Leu Gln Val Asp Cys
1               5                   10                  15

<210> SEQ ID NO 389
<211> LENGTH: 14
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (12)..(13)
<223> OTHER INFORMATION: Individual Z Variant

<400> SEQUENCE: 389

Met Gly Ser Ser His His His His His His Leu Gln Val Asp
1               5                   10

<210> SEQ ID NO 390
<211> LENGTH: 8
<212> TYPE: PRT
<213> ORGANISM: Artificial Sequence
<220> FEATURE:
<223> OTHER INFORMATION: Engineered CAIX-binding polypeptide
<220> FEATURE:
<221> NAME/KEY: MISC_FEATURE
<222> LOCATION: (6)..(7)
<223> OTHER INFORMATION: Individual 7 Variant

<400> SEQUENCE: 390

His Glu His Glu His Glu Val Asp
1               5
```

POLYPEPTIDES

CROSS-REFERENCE TO RELATED APPLICATIONS

This application is a U.S. National Stage application of PCT/EP2013/077334 filed Dec. 19, 2013 which claims priority to U.S. Provisional Patent Application No. 61/739,103 filed Dec. 19, 2012, all of which are incorporated by reference in their entirety.

FIELD OF THE INVENTION

The present disclosure relates to a class of engineered polypeptides having a binding affinity for carbonic anhydrase IX (in the following referred to as CAIX). The present disclosure also relates to the use of such a CAIX binding polypeptide as a diagnostic, prognostic and/or therapeutic agent.

BACKGROUND

Carbonic anhydrases (CAs) are a large family of zinc metalloenzymes that catalyze the reversible hydration of carbon dioxide. They participate in a variety of biological processes, including respiration, calcification, acid-base balance, bone resorption, and the formation of aqueous humor, cerebrospinal fluid, saliva, and gastric acid. They show extensive diversity in tissue distribution and in their subcellular localization. CAIX (also known as MN) is a transmembrane protein encoded by the CA9 gene and has been shown to be expressed in cancer tumors.

Tumor Microenvironment

The microenvironment of solid tumors is shaped by a biochemical and physiological interplay between cancer cells on one hand, and supporting stromal and vessel cells on the other hand. Tumors often grow at a rate that exceeds the blood supply capacity of the host vasculature, which would normally impede further development of most normal tissues. Tumors, however, escape this negative feedback and maintain high respiratory rates and are surviving even when oxygen, a principal blood-borne substrate, is scarce. Indeed, low oxygen tension (hypoxia) is a cardinal feature of the tumor milieu (Gatenby and Gillies (2004) Nat Rev Cancer 4: 891-899). Hypoxia is not only a consequence of tumor respiration, but also a trigger for an altered program of gene expression, featuring hypoxia-inducible genes (Gleadle and Ratcliffe (1998) Mol Med Today 4: 122-129; Harris (2002) Nat Rev Cancer 2:38-47), that is involved in progressing cancer towards a more aggressive disease phenotype (Fang et al., (2008) Semin Cancer Biol 18: 330-337). Many of the hypoxia-regulated genes are controlled by hypoxia-inducible factor, a transcription factor that is otherwise inactivated in the presence of oxygen. The targets of hypoxia-inducible factor include genes that encode proteins involved in glucose metabolism, blood vessel growth, oxygen carriage, iron metabolism and numerous other processes.

CAIX Expression and Function

CAIX was originally cloned in the mid 1990s by Pastorek and coworkers (Pastorek et al., (1994) Oncogene 9: 2877-2888). CAIX is a hypoxia-inducible enzyme and a component of the pH regulatory system invoked by cells to combat the deleterious effects of a high rate of glycolytic metabolism (Wykoff et al., (2000) Cancer Res 60: 7075-7083).

CAIX expression, unlike the expression of most other CA isoforms, is associated with many tumors (Pastorek et al., (1994) supra; De Simone and Supuran, (2010) Biochim Biophys Acta 1804: 404-409). Indeed, very few normal tissues (with the notable exception of stomach (Pastorekova et al., (1997) Gastroenterology 112: 398-408)) express significant levels of CAIX, so positive staining for CAIX is now an established marker of tumor hypoxia and a clinical indicator of aggressive cancers (for example breast and bone cancer) with a poor prognosis (reviewed in McDonald et al (2012) Oncotarget 3:84-97).

CAIX functions to help produce and maintain an intracellular pH (pHi) favorable for tumor cell growth and survival, while at the same time participating in the generation of an increasingly acidic extracellular space, facilitating tumor cell invasiveness.

CAIX is membrane tethered and its catalytic domain faces the extracellular environment. The crystal structure of CAIX has been resolved, showing that CAIX exists as a dimer (Alterio et al., (2009) Proc Natl Acad Sci USA 106: 16233-16238; De Simone and Supuran, (2010) supra). The protein contains a proteoglycan-like domain and an intracellular carboxy terminal tail that may be involved in cell-cell adhesion and in regulating the catalytic process. Recent work (Innocenti et al., (2009) Bioorg Med Chem Lett 19: 5825-5828) has proposed that the presence of the proteoglycan domain, rich in acidic amino acid residues, reduces the inhibitory effects of $H^+$ ions on CAIX activity. This is observed as a shift in the pH sensitivity of CAIX activity by half a pH unit towards more acidic values, enabling CAIX to remain catalytically active in the acidic extracellular milieu that is typical of solid tumors.

CAIX and Cancer

CAIX is an especially attractive target for cancer therapy, in part because it is over-expressed in a wide variety of solid tumors, but is expressed in a limited way in normal tissues. In human tissue, strong expression of CAIX is generally limited to the basolateral surface of proliferating crypt enterocytes of the duodenum, jejunum and ileal mucosa (Pastorekova et al (1997) supra; Saarnio et al (1998) J Histochem Cytochem 46:497-504). However, diffuse, weak CAIX expression has also been reported in other tissues.

CAIX is over-expressed in many solid tumors, and there is a well established relationship between the expression of CAIX and patient prognosis. CAIX expression, as detected by immunohistochemical staining of tissue sections, is upregulated and associated with poor prognosis in cancers of the lung, colon, breast, cervix, bladder, kidney, brain, head and neck, and oral cavity (reviewed in McDonald et al (2012) supra). Furthermore, recent studies have examined the expression of CAIX in cohorts of from hundreds to thousands of patients using tissue microarray strategies. Using this high throughput platform, CAIX has been validated as a biomarker of a poor prognosis in breast, lung, ovarian and bladder cancer as well as in astrocytomas (reviewed in McDonald et al (2012), supra).

There is now an increasing focus on the use of CAIX for clinical detection and prognostic evaluation. Initial studies, involving relatively small sample sizes, showed that soluble CAIX was upregulated in serum in patients with solid tumors (Woelber et al (2010) Gynecol Oncol 117:183-188; Hyrsl et al (2009) Neoplasma:56:298-302) and recent studies have shown an association between soluble CAIX and patient prognosis. Preoperative serum CAIX concentrations in vulvar cancer correlate with intratumoral expression, and increased serum CAIX levels are associated with a poor prognosis (Kock et al (2011) Int J Gynecol Cancer 21:141-148). Serum levels of CAIX in metastatic breast cancer were also correlated with a poor prognosis, as well as with the incidence of circulating tumor cells (Muller et al (2011) Breast Cancer Res: 13: R71). Similarly, in NSCLC, high plasma levels of CAIX were associated with significantly shorter overall survival pie et al (2010) Br J Cancer. May 25; 102(11):1627-35).

Pharmacologic interference of CAIX catalytic activity using monoclonal antibodies or CAIX-specific small molecule inhibitors, consequently disrupting pH regulation by cancer cells, has recently been shown to impair primary tumor growth and metastasis.

However, monoclonal antibodies are not always optimal for targeting solid tumors (neither for diagnostic nor for therapeutic pay-load purposes). Therapeutic effect is dependent on an efficient distribution of the drug throughout the tumor, and molecular imaging depends on a high ratio between tumor uptake and surrounding normal tissue.

Since tumor penetration rate (including extravasation) is negatively associated with the size of the molecule, the relatively large antibody molecule inherently has poor tissue distribution and penetration capacity. Moreover, for molecular imaging, the extraordinarily long in vivo half-life of antibodies results in relatively high blood signals and thereby relatively poor tumor-to-blood contrasts.

The continued provision of agents with a high affinity for CAIX remains a matter of substantial interest within the field. Of great interest is also the provision of uses of such molecules in the treatment and diagnosis of disease.

SUMMARY OF THE INVENTION

It is an object of the present disclosure to provide new CAIX binding agents, which could for example be used for diagnostic, prognostic and therapeutic applications.

It is an object of the present disclosure to provide a molecule allowing for efficient therapy targeting various forms of cancer while alleviating the abovementioned and other drawbacks of current therapies.

It is furthermore an object of the present disclosure to provide a molecule suitable for prognostic and diagnostic applications.

These and other objects which are evident to the skilled person from the present disclosure are met by different aspects of the invention as claimed in the appended claims and as generally disclosed herein.

Thus, in the first aspect of the disclosure, there is provided a carbonic anhydrase IX (CAIX) binding polypeptide, comprising a CAIX binding motif, BM, which motif consists of an amino acid sequence selected from i)
$$EX_2X_3X_4AX_6X_7EIX_{10}\ X_{11}\ LPNLX_{16}X_{17}X_{18}QX_{20}\ X_{21}AFIX_{25}X_{26}LWD$$
(SEQ ID NO. 369)

wherein, independently from each other,
$X_2$ is selected from D, H, N, Q and W;
$X_3$ is selected from E, F, I, K, L, Q, R, S, T, V, W and Y;
$X_4$ is selected from A, F, N, W and Y;
$X_6$ is selected from A, G, S and W;
$X_7$ is selected from A, E, G, I, Q, T, V and W;
$X_{10}$ is selected from A, D, E, G, H, I, N, Q, R, S, T and V;
$X_{11}$ is selected from D, E, K, R and S;
$X_{16}$ is selected from N and T;
$X_{17}$ is selected from A, D, E, G, H, I, Q, S, T, V and W;
$X_{18}$ is selected from A, D, E, F, G, H, I, L, N, Q, R, S, T, V, W and Y;
$X_{20}$ is selected from K, Q and R;
$X_{21}$ is selected from D, H, N and Q;
$X_{25}$ is selected from F and Y;
$X_{26}$ is selected from K and S;
and
ii) an amino acid sequence which has at least 89% identity to the sequence defined in i).

The above definition of a class of sequence related, CAIX binding polypeptides is based on a statistical analysis of a number of random polypeptide variants of a parent scaffold, that were selected for their interaction with CAIX in several different selection experiments. The identified CAIX binding motif, or "BM", corresponds to the target binding region of the parent scaffold, which region constitutes two alpha helices within a three-helical bundle protein domain. In the parent scaffold, the varied amino acid residues of the two BM helices constitute a binding surface for interaction with the constant Fc part of antibodies. In the present disclosure, the random variation of binding surface residues and subsequent selection of variants have replaced the Fc interaction capacity with a capacity for interaction with CAIX.

As the skilled person will realize, the function of any polypeptide, such as the CAIX binding capacity of the polypeptide of the present disclosure, is dependent on the tertiary structure of the polypeptide. It is therefore possible to make minor changes to the sequence of amino acids in a polypeptide without affecting the function thereof. Thus, the disclosure encompasses modified variants of the CAIX binding polypeptide, which are such that the CAIX binding characteristics are retained.

In this way, also encompassed by the present disclosure is a CAIX binding polypeptide comprising an amino acid sequence with 89% or greater identity to a polypeptide as defined in i). In some embodiments, the polypeptide may comprise a sequence which is at least 93%, such as at least 97% identical to the polypeptides as defined in i).

In some embodiments, such changes may be made in all positions of the sequences of the CAIX binding polypeptide as disclosed herein. In other embodiments, such changes may be made only in the non-variable positions, also denoted as scaffold amino acid residues. In such cases, changes are not allowed in the variable positions, i.e. positions denoted with an "X" in sequence i). For example, it is possible that an amino acid residue belonging to a certain functional grouping of amino acid residues (e.g. hydrophobic, hydrophilic, polar etc) could be exchanged for another amino acid residue from the same functional group.

The term "% identity", as used throughout the specification, may for example be calculated as follows. The query sequence is aligned to the target sequence using the CLUSTAL W algorithm (Thompson et al, Nucleic Acids Research, 22: 4673-4680 (1994)). A comparison is made over the window corresponding to the shortest of the aligned sequences. The shortest of the aligned sequences may in some instances be the target sequence. In other instances, the query sequence may constitute the shortest of the aligned sequences. The amino acid residues at each position are compared, and the percentage of positions in the query sequence that have identical correspondences in the target sequence is reported as % identity.

In one embodiment of a polypeptide according to the first aspect, sequence i) is defined by:

$$EX_2X_3X_4AX_6X_7EIX_{10}\ X_{11}LPNLX_{16}X_{17}X_{18}QX_{20}\ X_{21}AFIYX_{26}LWD$$
(SEQ ID NO. 370)

wherein, independently from each other,
$X_2$ is selected from D, H, N, Q and W;
$X_3$ is selected from F, I, L, Q, R, S, T, V, W and Y;
$X_4$ is selected from A, F, N, W and Y;
$X_6$ is selected from A, G, S and W;
$X_7$ is selected from A, E, G, I, V and W;
$X_{10}$ is selected from A, D, E, G, H, N, Q, R, S, T and V;
$X_{11}$ is selected from D, E, R and S;
$X_{16}$ is selected from N and T;

$X_{17}$ is selected from A, D, E, G, I, Q, S, T, V and W;
$X_{18}$ is selected from A, D, E, F, G, H, I, L, N, Q, R, S, T, V, W and Y;
$X_{20}$ is selected from Q and R;
$X_{21}$ is selected from D, H, N and Q; and
$X_{26}$ is selected from K and S.

In one embodiment, $X_2$ in sequence i) is selected from H, N, Q and W.

In one embodiment, $X_2$ in sequence i) is selected from D, H, N and Q.

In one embodiment, $X_2$ in sequence i) is selected from H, N and W.

In one embodiment, $X_2$ in sequence i) is selected from H and W.

In one embodiment, $X_2$ in sequence i) is selected from N and W.

In one embodiment, $X_2$ in sequence i) is selected from H and N.

In another embodiment, $X_2$ in sequence i) is H.
In another embodiment, $X_2$ in sequence i) is N.
In yet another embodiment, $X_2$ in sequence i) is W.

In one embodiment, $X_3$ in sequence i) is selected from I, L, Q, R, S and W.

In one embodiment, $X_3$ in sequence i) is selected from I, L, Q, R and W.

In one embodiment, $X_3$ in sequence i) is selected from I, L, Q and W.

In one embodiment, $X_3$ in sequence i) is selected from I, L, R and W.

In one embodiment, $X_3$ in sequence i) is selected from I, L and W.

In one embodiment, $X_3$ in sequence i) is selected from I and L.

In one embodiment, $X_3$ in sequence i) is I.
In one embodiment, $X_3$ in sequence i) is L.

In one embodiment, $X_4$ in sequence i) is selected from A, F, W and Y.

In one embodiment, $X_4$ in sequence i) is selected from A, F and W.

In one embodiment, $X_4$ in sequence i) is selected from F and W.

In one embodiment, $X_4$ in sequence i) is F.
In one embodiment, $X_4$ in sequence i) is W.

In one embodiment, $X_6$ in sequence i) is selected from A, G and S.

In one embodiment, $X_6$ in sequence i) is selected from A and G.

In one embodiment, $X_6$ in sequence i) is selected from G and S.

In one embodiment, $X_6$ in sequence i) is G.

In one embodiment, $X_7$ in sequence i) is selected from G, I, V and W.

In one embodiment, $X_7$ in sequence i) is selected from V and W.

In one embodiment, $X_7$ in sequence i) is selected from I and W.

In one embodiment, $X_7$ in sequence i) W.

In one embodiment, $X_{10}$ in sequence i) is selected from A, D, E, G, H, N, Q, R, S and T.

In one embodiment, $X_{10}$ in sequence i) is selected from A, D, E, G, N, Q, S and T.

In one embodiment, $X_{10}$ in sequence i) is selected from A, D, E, G, N, S and T.

In one embodiment, $X_{10}$ in sequence i) is selected from A, D, E, G, Q, S and T.

In one embodiment, $X_{10}$ in sequence i) is selected from A, D, E, Q, S and T.

In one embodiment, $X_{10}$ in sequence i) is selected from A, D, E, G, S and T.

In one embodiment, $X_{10}$ in sequence i) is selected from A, D, E, S and T.

In one embodiment, $X_{10}$ in sequence i) is selected from D, E, S and T.

In one embodiment, $X_{10}$ in sequence i) is selected from A, D, S and T.

In one embodiment, $X_{10}$ in sequence i) is selected from D, S and T.

In one embodiment, $X_{10}$ in sequence i) is selected from A, D and S.

In one embodiment, $X_{10}$ in sequence i) is selected from D and T.

In one embodiment, $X_{10}$ in sequence i) is selected from D and S.

In one embodiment, $X_{10}$ in sequence i) is D.

In one embodiment, $X_{11}$ in sequence i) is selected from D, E and S.

In one embodiment, $X_{11}$ in sequence i) is selected from D and E.

In one embodiment, $X_{11}$ in sequence i) is D.
In one embodiment, $X_{16}$ in sequence i) is N.
In one embodiment, $X_{16}$ in sequence i) is T.

In one embodiment, $X_{17}$ in sequence i) is selected from A, D, E, I, Q, T and V.

In one embodiment, $X_{17}$ in sequence i) is selected from A, D, E, I, Q and V.

In one embodiment, $X_{17}$ in sequence i) is selected from D, E, I, Q, T and V.

In one embodiment, $X_{17}$ in sequence i) is selected from D, E, I, Q and V.

In one embodiment, $X_{17}$ in sequence i) is selected from D, E, I and Q.

In one embodiment, $X_{17}$ in sequence i) is selected from D, E and Q.

In one embodiment, $X_{17}$ in sequence i) is selected from D, E and I.

In one embodiment, $X_{17}$ in sequence i) is selected from D and E.

In one embodiment, $X_{17}$ in sequence i) is E.
In one embodiment, $X_{17}$ in sequence i) is D.

In one embodiment, $X_{18}$ in sequence i) is selected from A, D, E, F, G, H, I, N, Q, R, S, T and Y.

In one embodiment, $X_{18}$ in sequence i) is selected from A, D, E, F, G, H, N, Q, R, S and Y.

In one embodiment, $X_{18}$ in sequence i) is selected from A, D, F, H, N, Q, R, S and Y.

In one embodiment, $X_{18}$ in sequence i) is selected from D, F, H, Q, R, S and Y.

In one embodiment, $X_{18}$ in sequence i) is selected from D, H, Q, R and Y.

In one embodiment, $X_{18}$ in sequence i) is selected from D, H, Q and Y.

In one embodiment, $X_{18}$ in sequence i) is selected from D, H and Q.

In one embodiment, $X_{18}$ in sequence i) is selected from D, Q and Y.

In one embodiment, $X_{18}$ in sequence i) is selected from D and Q.

In one embodiment, $X_{18}$ in sequence i) is selected from Q and Y.

In one embodiment, $X_{18}$ in sequence i) is selected from H and Q.

In one embodiment, $X_{18}$ in sequence i) is Q.

In one embodiment, $X_{18}$ in sequence i) is selected from A, D, E, F, H, Q, R, S and Y.

In one embodiment, $X_{18}$ in sequence i) is selected from D, E, F, H, Q, R, S and Y.

In one embodiment, $X_{18}$ in sequence i) is selected from D, E, F, H, Q, S and Y.

In one embodiment, $X_{18}$ in sequence i) is selected from D, E, F, Q, S and Y.

In one embodiment, $X_{18}$ in sequence i) is selected from D, E, Q, S and Y.

In one embodiment, $X_{18}$ in sequence i) is selected from D, E, S and Y.

In one embodiment, $X_{18}$ in sequence i) is selected from D, E and Y.

In one embodiment, $X_{20}$ in sequence i) is R.

In one embodiment, $X_{21}$ in sequence i) is selected from D, H and N.

In one embodiment, $X_{21}$ in sequence i) is selected from D and N.

In one embodiment, $X_{21}$ in sequence i) is selected from H and N.

In one embodiment, $X_{21}$ in sequence i) is N.

In one embodiment, $X_{25}$ in sequence i) is Y.

In one embodiment, $X_{26}$ in sequence i) is K.

In one embodiment, $X_{26}$ in sequence i) is S.

In a more specific embodiment defining a sub-class of the CAIX binding polypeptide, sequence i) fulfills at least seven of the twelve conditions I-XII:

I. $X_2$ is N;
II. $X_3$ is selected from I and L;
III. $X_4$ is F;
IV. $X_6$ is G;
V. $X_7$ is W;
VI. $X_{10}$ is selected from D and S;
VII. $X_{11}$ is D;
VIII. $X_{16}$ is T;
IX. $X_{17}$ is selected from E and D;
X. $X_{18}$ is selected from D, Y, E and S;
XI. $X_{21}$ is N; and
XII. $X_{26}$ is K.

In some examples of a CAIX binding polypeptide according to the first aspect, sequence i) fulfils at least eight of the twelve conditions I-XII. More specifically, sequence i) may fulfill at least nine of the twelve conditions I-XII, such at least ten of the twelve conditions I-XII, such at least eleven of the twelve conditions I-XII, such as all of the twelve conditions I-XII.

As described in detail in the experimental section to follow, the selection of CAIX binding polypeptide variants has led to the identification of a number of individual CAIX binding motif (BM) sequences. These sequences constitute individual embodiments of sequence i) according to this aspect. The sequences of individual CAIX binding motifs are presented in FIG. 1 and as SEQ ID NO:1-113 and SEQ ID NO:340-344. Hence, in one embodiment of the CAIX binding polypeptide according to this aspect, sequence i) is selected from the group consisting of SEQ ID NO:1-113 and SEQ ID NO:340-344. In one embodiment, sequence i) is selected from the group consisting of SEQ ID NO:1-113. In one embodiment, sequence i) is selected from the group consisting of SEQ ID NO:1-4 and SEQ ID NO:6-41. In one embodiment, sequence i) is selected from the group consisting of SEQ ID NO:1-4, SEQ ID NO:6 and SEQ ID NO:8-37. In another embodiment, sequence i) is selected from the group consisting of SEQ ID NO:1-14. In yet another embodiment, sequence i) is selected from SEQ ID NO:1-8 and SEQ ID NO:10-13. In yet another embodiment, sequence i) is selected from SEQ ID NO:1-5. In one embodiment, sequence i) is selected from SEQ ID NO:1-4. In one embodiment, sequence i) is selected from SEQ ID NO:1-3.

In some embodiments of the present disclosure, the BM as defined above "forms part of" a three-helix bundle protein domain. This is understood to mean that the sequence of the BM is "inserted" into or "grafted" onto the sequence of the original three-helix bundle domain, such that the BM replaces a similar structural motif in the original domain. For example, without wishing to be bound by theory, the BM is thought to constitute two of the three helices of a three-helix bundle, and can therefore replace such a two-helix motif within any three-helix bundle. As the skilled person will realize, the replacement of two helices of the three-helix bundle domain by the two BM helices has to be performed so as not to affect the basic structure of the polypeptide. That is, the overall folding of the Cα backbone of the polypeptide according to this embodiment of the invention is substantially the same as that of the three-helix bundle protein domain of which it forms a part, e.g. having the same elements of secondary structure in the same order etc. Thus, a BM according to the disclosure "forms part" of a three-helix bundle domain if the polypeptide according to this embodiment of the aspect has the same fold as the original domain, implying that the basic structural properties are shared, those properties e.g. resulting in similar CD spectra. The skilled person is aware of other parameters that are relevant.

In particular embodiments, the CAIX binding motif (BM) thus forms part of a three-helix bundle protein domain. For example, the BM may essentially constitute two alpha helices with an interconnecting loop, within said three-helix bundle protein domain. In particular embodiments, said three-helix bundle protein domain is selected from domains of bacterial receptor proteins. Non-limiting examples of such domains are the five different three-helical domains of Protein A from *Staphylococcus aureus*, such as domain B, and derivatives thereof. In some embodiments, the three-helical bundle protein domain is a variant of protein Z, which is derived from domain B of staphylococcal Protein A.

In embodiments where the CAIX binding polypeptide of the invention forms part of a three-helix bundle protein domain, the CAIX binding polypeptide may comprise an amino acid sequence selected from:

```
iii)
                                          (SEQ ID NO. 371)
K-[BM]-DPSQS XₐXᵦLLXc EAKKL NDXdQ;
``` wherein

[BM] is a CAIX binding motif as defined herein;
$X_a$ is selected from A and S;
$X_b$ is selected from N and E;
$X_c$ is selected from A, S and C;
$X_d$ is selected from A and S; and
iv) an amino acid sequence which has at least 81% identity to a sequence defined by iii).

As discussed above, polypeptides comprising minor changes as compared to the above amino acid sequences without largely affecting the tertiary structure and the function thereof are also within the scope of the present disclosure. Thus, in some embodiments, sequence iv) has at least 83%, such as at least 85%, such as at least 87%, such as at least 89%, such as at least 91%, such as at least 93%, such as at least 95%, such as at least 97% identity to a sequence defined by iii).

In one embodiment, $X_a$ in sequence iii) is A. In an alternative embodiment, $X_a$ in sequence iii) is S.

In one embodiment, $X_b$ in sequence iii) is N. In an alternative embodiment, $X_b$ in sequence iii) is E.

In one embodiment, $X_c$ in sequence iii) is A. In an alternative embodiment, $X_c$ in sequence iii) is S. In yet another alternative embodiment, $X_c$ in sequence iii) is C.

In one embodiment, $X_d$ in sequence iii) is A. In an alternative embodiment, $X_d$ in sequence iii) is S.

In one embodiment, in sequence iii), $X_a$ is A; $X_b$ is N; $X_c$ is A and $X_d$ is A.

In a further embodiment, in sequence iii), $X_a$ is A; $X_b$ is N; $X_c$ is C and $X_d$ is A.

In a further embodiment, in sequence iii), $X_a$ is S; $X_b$ is E; $X_c$ is S and $X_d$ is S.

In a further embodiment, in sequence iii), $X_a$ is S; $X_b$ is E; $X_c$ is C and $X_d$ is S.

In yet a further embodiment, sequence iii) in the definition of CAIX binding polypeptides above is selected from SEQ ID NO:114-226 and SEQ ID NO:345-349. In one embodiment, sequence iii) is selected from the group consisting of SEQ ID NO:114-226. In one embodiment, sequence iii) is selected from the group consisting of SEQ ID NO:114-117 and SEQ ID NO:119-154. In one embodiment, sequence iii) is selected from the group consisting of SEQ ID NO:114-117, SEQ ID NO:119-121 and SEQ ID NO:123-150. In another embodiment, sequence iii) is selected from the group consisting of SEQ ID NO:114-127. In yet another embodiment, sequence iii) is selected from SEQ ID NO:114-121 and SEQ ID NO:123-126. In yet another embodiment, sequence iv is selected from SEQ ID NO:114-118. In one embodiment, sequence iv is selected from SEQ ID NO:114-117. In one embodiment, sequence iv is selected from SEQ ID NO:114-116.

Also, in a further embodiment, there is provided a CAIX binding polypeptide as defined above, which comprises an amino acid sequence selected from:

v)
(SEQ ID NO. 372)
YAK-[BM]-DPSQS SELLX$_c$ EAKKL NDSQA P;

wherein [BM] is a CAIX binding motif as defined above and $X_c$ is selected from S and C; and vi) an amino acid sequence which has at least 83% identity to a sequence defined by v).

Alternatively, there is provided a CAIX binding polypeptide as defined above, which comprises an amino acid sequence selected from:

vii)
(SEQ ID NO. 373)
FNK-[BM]-DPSQS ANLLX$_c$ EAKKL NDAQA P;

wherein [BM] is a CAIX binding motif as defined above and $X_c$ is selected from A and C; and viii) an amino acid sequence which has at least 83% identity to a sequence defined by vii).

As discussed above, polypeptides comprising minor changes as compared to the above amino acid sequences without largely affecting the tertiary structure and the function thereof are also within the scope of the present disclosure. Thus, in some embodiments, the CAIX binding polypeptides as defined above may for example have a sequence which is at least 84%, at least 86%, at least 88%, at least 90%, at least 92%, at least 94%, at least 96%, or at least 98% identical to a sequence defined by v) or vii).

In some embodiments, the CAIX binding motif may form part of a polypeptide comprising an amino acid sequence selected from (SEQ ID NO. 374)
ADNNFNK-[BM]-DPSQSANLLSEAKKLNESQAPK;

(SEQ ID NO. 375)
ADNKFNK-[BM]-DPSQSANLLAEAKKLNDAQAPK;

(SEQ ID NO. 376)
ADNKFNK-[BM]-DPSVSKEILAEAKKLNDAQAPK;

(SEQ ID NO. 377)
ADAQQNNFNK-[BM]-DPSQSTNVLGEAKKLNESQAPK;

(SEQ ID NO. 378)
AQHDE-[BM]-DPSQSANVLGEAQKLNDSQAPK;

(SEQ ID NO. 379)
VDNKFNK-[BM]-DPSQSANLLAEAKKLNDAQAPK;

(SEQ ID NO. 380)
AEAKYAK-[BM]-DPSESSELLSEAKKLNKSQAPK;

(SEQ ID NO. 381)
VDAKYAK-[BM]-DPSQSSELLAEAKKLNDAQAPK;

(SEQ ID NO. 382)
VDAKYAK-[BM]-DPSQSSELLAEAKKLNDSQAPK;

(SEQ ID NO. 383)
AEAKYAK-[BM]-DPSQSSELLSEAKKLNDSQAPK;

(SEQ ID NO. 384)
VDAKYAK-[BM]-DPSQSSELLSEAKKLNDSQAPK;

(SEQ ID NO. 385)
VDAKYAK-[BM]-DPSQSSELLAEAKKLNKAQAPK;
and (SEQ ID NO. 386)
AEAKYAK-[BM]-DPSQSSELLAEAKKLNKAQAPK.

In one embodiment, the CAIX binding polypeptide comprises an amino acid sequence selected from any one of SEQ ID NO:365-368.

In one embodiment, the CAIX binding polypeptide comprises an amino acid sequence selected from:

ix)
(SEQ ID NO. 384)
VDAKYAK-[BM]-DPSQSSELLSEAKKLNDSQAPK;

wherein [BM] is an CAIX binding motif as defined above; and x) an amino acid sequence which has at least 84% identity to the sequence defined in ix).

Again, polypeptides comprising minor changes as compared to the above amino acid sequences without largely affecting the tertiary structure and the function thereof are also within the scope of the present disclosure. Thus, in some embodiments, the CAIX binding polypeptides as defined above may for example have a sequence which is at least 86%, at least 87%, at least 89%, at least 91%, at least 93%, at least 94%, at least 96%, or at least 98% identical to the sequence defined by ix).

Sequence ix) in such a polypeptide may be selected from any one of SEQ ID NO:227-339 and SEQ ID NO:350-354. In one embodiment, sequence ix) is selected from the group consisting of SEQ ID NO:227-339. In one embodiment, sequence ix) is selected from the group consisting of SEQ ID NO:227-230 and SEQ ID NO:232-267. In one embodiment, sequence ix) is selected from the group consisting of SEQ ID NO:227-230, SEQ ID NO:232-234 and SEQ ID NO:236-263. In another embodiment, sequence ix) is selected from the group consisting of SEQ ID NO:227-240. In yet another embodiment, sequence ix) is selected from SEQ ID NO:227-234 and SEQ ID NO:236-239. In yet another embodiment, sequence ix) is selected from SEQ ID NO:227-231. In one embodiment, sequence ix) is selected from SEQ ID NO:227-230. In one embodiment, sequence ix) is selected from SEQ ID NO:227-229.

The terms "CAIX binding" and "binding affinity for CAIX" as used in this specification refer to a property of a polypeptide which may be tested for example by the use of surface plasmon resonance (SPR) technology. For example as described in the examples below, CAIX binding affinity may be tested in an experiment in which CAIX, or a fragment thereof, is immobilized on a sensor chip of the instrument, and the sample containing the polypeptide to be tested is passed over the chip. Alternatively, the polypeptide to be tested is immobilized on a sensor chip of the instrument, and a sample containing CAIX, or a fragment thereof, is passed over the chip. The skilled person may then interpret the results obtained by such experiments to establish at least a qualitative measure of the binding affinity of the polypeptide for CAIX. If a quantitative measure is desired, for example to determine a $K_D$ value for the interaction, surface plasmon resonance methods may also be used. Binding values may for example be defined in a Biacore (GE Healthcare) or ProteOn XPR 36 (Bio-Rad) instrument. CAIX is suitably immobilized on a sensor chip of the instrument, and samples of the polypeptide whose affinity is to be determined are prepared by serial dilution and injected in random order. $K_D$ values may then be calculated from the results using for example the 1:1 Langmuir binding model of the BIAevaluation 4.1 software, or other suitable software, provided by the instrument manufacturer.

In one embodiment, the CAIX binding polypeptide is capable of binding to CAIX such that the $K_D$ value of the interaction is at most $1\times10^{-6}$ M, such as at most $1\times10^{-7}$ M, such as at most $1\times10^{-8}$ M, such as at most $1\times10^{-9}$ M.

The skilled person will understand that various modifications and/or additions can be made to a CAIX binding polypeptide according to any aspect disclosed herein in order to tailor the polypeptide to a specific application without departing from the scope of the present disclosure.

For example, in one embodiment there is provided a CAIX binding polypeptide as described herein, which polypeptide has been extended by and/or comprises additional amino acids at the C terminal and/or N terminal end. Such a polypeptide should be understood as a polypeptide having one or more additional amino acid residues at the very first and/or the very last position in the polypeptide chain, i.e. at the N- and/or C-terminus of sequence i) or ii). Thus, a CAIX binding polypeptide may comprise any suitable number of additional amino acid residues, for example at least one additional amino acid residue. Each additional amino acid residue may individually or collectively be added in order to, for example, improve production, purification, stabilization in vivo or in vitro, coupling, or detection of the polypeptide. Such additional amino acid residues may comprise one or more amino acid residues added for the purpose of chemical coupling. One example of this is the addition of a cysteine residue. Such additional amino acid residues may also provide a "tag" for purification or detection of the polypeptide, such as a $His_6$ tag, a $(HisGlu)_3$ tag ("HEHEHE" tag) or a "myc" (c-myc) tag or a "FLAG" tag for interaction with antibodies specific to the tag or immobilized metal affinity chromatography (IMAC) in the case of the $His_6$-tag.

The further amino acids as discussed above may be coupled to the CAIX binding polypeptide by means of chemical conjugation (using known organic chemistry methods) or by any other means, such as expression of the CAIX binding polypeptide as a fusion protein or joined in any other fashion, either directly or via a linker, for example an amino acid linker.

The further amino acids as discussed above may for example comprise one or more polypeptide domain(s). A further polypeptide domain may provide the CAIX binding polypeptide with another function, such as for example yet another binding function, or an enzymatic function, or a toxic function (e.g. an immunotoxin), or a fluorescent signaling function, or combinations thereof.

A further polypeptide domain may moreover provide another CAIX binding moiety with the same CAIX binding function. Thus, in a further embodiment, there is provided a CAIX binding polypeptide in a multimeric form. Said multimer is understood to comprise at least two CAIX binding polypeptides as disclosed herein as monomer units, the amino acid sequences of which may be the same or different. Multimeric forms of the polypeptides may comprise a suitable number of domains, each having a CAIX binding motif, and each forming a monomer within the multimer. These domains may have the same amino acid sequence, but alternatively, they may have different amino acid sequences. In other words, the CAIX binding polypeptide of the invention may form homo- or heteromultimers, for example homo- or heterodimers. In one embodiment, there is provided a CAIX binding polypeptide, wherein said monomeric units are covalently coupled together. In another embodiment, said CAIX binding polypeptide monomer units are expressed as a fusion protein. In one embodiment, there is provided a CAIX binding polypeptide in dimeric form.

Additionally, "heterogenic" fusion polypeptides or proteins, or conjugates, in which a CAIX binding polypeptide described herein, or multimer thereof, constitutes a first domain, or first moiety, and the second and further moieties have other functions than binding CAIX, are also contemplated and fall within the ambit of the present disclosure. The second and further moiety/moieties of the fusion polypeptide or conjugate in such a protein suitably have a desired biological activity.

Thus, in a second aspect of the present disclosure, there is provided a fusion protein or a conjugate, comprising a first moiety consisting of a CAIX binding polypeptide according to the first aspect, and a second moiety consisting of a polypeptide having a desired biological activity. In another embodiment, said fusion protein or conjugate may additionally comprise further moieties, comprising desired biological activities that can be either the same or different from the biological activity of the second moiety.

Non-limiting examples of such a desired biological activity comprise a therapeutic activity, a binding activity, and an enzymatic activity. In one embodiment, the second moiety having a desired biological activity is a therapeutically active polypeptide. Non-limiting examples of binding activities are binding activities which increase the in vivo half-life of the fusion protein or conjugate. In one particular embodiment, said binding activity is albumin binding activity which increase the in vivo half-life of the fusion protein or conjugate. In one embodiment, said albumin binding activity comprises the albumin binding domain of streptococcal protein G or a derivative thereof.

Non-limiting examples of therapeutically active polypeptides are biomolecules, such as molecules selected from the group consisting of human endogenous enzymes, hormones, growth factors, chemokines, cytokines and lymphokines.

In one embodiment of this aspect of the present disclosure, there is provided a CAIX binding polypeptide, fusion protein or conjugate which further comprises a cytotoxic agent. Non-limiting examples of cytotoxic agents are agents selected from the group consisting of auristatin, anthracycline, calicheamycin, combretastatin, doxorubicin, duocarmycin, the CC-1065 anti-tumorantibiotic, ecteinsascidin, geldanamycin, maytansinoid, methotrexate, mycotoxin, taxol, ricin, bouganin, gelonin, pseudomonas exotoxin 38 (PE38), diphtheria toxin (DT), and their analogues, and derivates thereof and combinations thereof. A skilled person would appreciate that the non-limiting examples of cytotoxic agents include all possible variant of said agents, for example the agent auristatin includes for example auristatin E, auristatin F, auristatin PE, and derivates thereof.

As the skilled person understands, the CAIX binding polypeptide according to the first aspect may be useful in a fusion protein or as a conjugate partner to any other moiety. Therefore, the above lists of therapeutically active polypeptides and cytotoxic agents should not be construed as limiting in any way.

Other possibilities for the creation of fusion polypeptides or conjugates are also contemplated. Thus, an CAIX binding polypeptide according to the first aspect of the invention may be covalently coupled to a second or further moiety or moieties, which in addition to or instead of target binding exhibit other functions. One example is a fusion between one or more CAIX binding polypeptide(s) and an enzymatically active polypeptide serving as a reporter or effector moiety.

With regard to the description above of fusion proteins or conjugates incorporating an CAIX binding polypeptide according to the invention, it is to be noted that the designation of first, second and further moieties is made for clarity reasons to distinguish between CAIX binding polypeptide or polypeptides according to the invention on the one hand, and moieties exhibiting other functions on the other hand. These designations are not intended to refer to the actual order of the different domains in the polypeptide chain of the fusion protein or conjugate. Thus, for example, said first moiety may without restriction appear at the N-terminal end, in the middle, or at the C-terminal end of the fusion protein or conjugate.

The above aspects furthermore encompass polypeptides in which the CAIX binding polypeptide according to the first aspect, or the CAIX binding polypeptide as comprised in a fusion protein or conjugate according to the second aspect, further comprises a label, such as a label selected from the group consisting of fluorescent dyes and metals, chromophoric dyes, chemiluminescent compounds and bioluminescent proteins, enzymes, radionuclides and particles. Such labels may for example be used for detection of the polypeptide.

For example, in embodiments where the labeled CAIX binding polypeptide comprises a CAIX binding polypeptide according to the first aspect of the disclosure and a label, the labeled polypeptide may for example be used for indirect labeling of CAIX expressing tumors cells as well as metastatic cells.

In other embodiments, the labeled CAIX binding polypeptide is present as a moiety in a fusion protein or conjugate also comprising a second moiety having a desired biological activity. The label may in some instances be coupled only to the CAIX binding polypeptide, and in some instances both to the CAIX binding polypeptide and to the second moiety of the conjugate or fusion protein. Furthermore, it is also possible that the label may be coupled to a second moiety only and not the CAIX binding moiety. Hence, in yet another embodiment there is provided a CAIX binding polypeptide comprising a second moiety, wherein said label is coupled to the second moiety only.

When reference is made to a labeled polypeptide, this should be understood as a reference to all aspects of polypeptides as described herein, including fusion proteins and conjugates comprising a CAIX binding polypeptide and a second and optionally further moieties. Thus, a labeled polypeptide may contain only the CAIX binding polypeptide and e.g. a therapeutic radionuclide, which may be chelated or covalently coupled to the CAIX binding polypeptide, or contain the CAIX binding polypeptide, a therapeutic radionuclide and a second moiety such as a small molecule having a desired biological activity, for example a therapeutic efficacy.

In embodiments where the CAIX binding polypeptide, fusion protein or conjugate is radiolabeled, such a radiolabeled polypeptide may comprise a radionuclide. A majority of radionuclides have a metallic nature and metals are typically incapable of forming stable covalent bonds with elements presented in proteins and peptides. For this reason, labeling of proteins and peptides with radioactive metals is performed with the use of chelators, i.e. multidentate ligands, which form non-covalent compounds, called chelates, with the metal ions. In an embodiment of the CAIX binding polypeptide, fusion protein or conjugate, the incorporation of a radionuclide is enabled through the provision of a chelating environment, through which the radionuclide may be coordinated, chelated or complexed to the polypeptide.

One example of a chelator is the polyaminopolycarboxylate type of chelator. Two classes of such polyaminopolycarboxylate chelators can be distinguished: macrocyclic and acyclic chelators.

In one embodiment, the CAIX binding polypeptide, fusion protein or conjugate comprises a chelating environment provided by a polyaminopolycarboxylate chelator conjugated to the CAIX binding polypeptide via a thiol group of a cysteine residue or an epsilon amine group of a lysine residue.

The most commonly used macrocyclic chelators for radioisotopes of indium, gallium, yttrium, bismuth, radioactinides and radiolanthanides are different derivatives of DOTA (1,4,7,10-tetraazacyclododecane-1,4,7,10-tetraacetic acid). In one embodiment, a chelating environment of the CAIX binding polypeptide, fusion protein or conjugate is provided by DOTA or a derivative thereof. More specifically, in one embodiment, the chelating polypeptides encompassed by the present disclosure are obtained by reacting the DOTA derivative 1,4,7,10-tetraazacyclododecane-1,4,7-trisacetic acid-10-maleimidoethylacetamide (maleimidomonoamide-DOTA) with said polypeptide.

Additionally, 1,4,7-triazacyclononane-1,4,7-triacetic acid (NOTA) and derivatives thereof may be used as chelators. Hence, in one embodiment, there is provided a CAIX binding polypeptide, fusion protein or conjugate, wherein the polyaminopolycarboxylate chelator is 1,4,7-triazacyclononane-1,4,7-triacetic acid or a derivative thereof.

The most commonly used acyclic polyaminopolycarboxylate chelators are different derivatives of DTPA (diethylenetriamine-pentaacetic acid). Hence, polypeptides having a chelating environment provided by diethylenetriaminepentaacetic acid or derivatives thereof are also encompassed by the present disclosure.

In a third aspect of the present disclosure, there is provided a polynucleotide encoding a CAIX binding polypeptide or a fusion protein as described herein. Also encompassed by this disclosure is a method of producing a polypeptide or fusion protein as described above comprising expressing a polynucleotide; an expression vector comprising the polynucleotide; and a host cell comprising the expression vector.

Also encompassed is a method of producing a polypeptide, comprising culturing said host cell under conditions permissive of expression of said polypeptide from its expression vector, and isolating the polypeptide.

The CAIX binding polypeptide of the present disclosure may alternatively be produced by non-biological peptide synthesis using amino acids and/or amino acid derivatives having protected reactive side-chains, the non-biological peptide synthesis comprising
- step-wise coupling of the amino acids and/or the amino acid derivatives to form a polypeptide according to the first aspect having protected reactive side-chains,
- removal of the protecting groups from the reactive side-chains of the polypeptide, and
- folding of the polypeptide in aqueous solution.

In another aspect there is provided a composition comprising a CAIX binding polypeptide, fusion protein or conjugate as described herein and at least one pharmaceutically acceptable excipient or carrier. In one embodiment, said composition further comprises at least one additional active agent, such as at least two additional active agents, such as at least three additional active agents. Non-limiting examples of additional active agents that may prove useful in such a combination are immunostimulatory agents, radionuclides, toxic agents, enzymes, factors recruiting effector cells (e.g. T or NK cells) and photosensitizers. In one embodiment, the at least one additional active agent may be an inhibitor of a hypoxia induced protein, such as an inhibitor of HIF-1α. The enzyme activity of CAIX has been suggested to be of potential significance for tumor progression because it is thought to be active in the acidification of the extracellular microenvironment surrounding cancer cells, thus facilitating tumor growth and invasion. Hence, in another embodiment, said at least one additional active agent may be a pH modulating agent. In yet another embodiment, said at least one additional active agent is selected from the group comprising angiogenesis inhibiting factors, cell division inhibiting factors and cytotoxic agents.

It should be understood that the CAIX binding polypeptide according to the present disclosure may be useful as a therapeutic, diagnostic or prognostic agent in its own right or as a means for targeting other therapeutic or diagnostic agents, with e.g. direct or indirect effects on CAIX. A direct therapeutic effect may for example be accomplished by inhibiting CAIX signaling. CAIX may also serve as a valuable marker to predict the prognosis of certain cancers, such as lung cancer, brain cancer, renal cancer and other. For example, in lung tumors the presence of CAIX has specifically been linked to the expression of proteins involved in angiogenesis, apoptosis inhibition and cell-cell adhesion disruption, which are all characteristic features of advanced cancer disease and poor clinical outcome.

Hence, in another aspect of the present disclosure, there is provided a CAIX binding polypeptide, fusion protein, conjugate or composition as described herein for use as a medicament, a diagnostic agent or a prognostic agent.

In one embodiment, there is provided a CAIX binding polypeptide, fusion protein or conjugate or composition as described herein, for use as a medicament to modulate CAIX function in vivo. As used herein, the term "modulate" refers to changing the activity, such as rendering CAIX function hypomorph, partially inhibiting or fully inhibiting CAIX function.

In one embodiment, there is provided a CAIX binding polypeptide, fusion protein, conjugate or composition for use in the treatment, diagnosis or prognosis of a CAIX related condition, such as cancer. In one embodiment, there is provided a CAIX binding polypeptide, fusion protein, conjugate or composition for use in prognosis or diagnosis together with at least one cell proliferation marker. Non-limiting examples of cell proliferation marker are cell proliferation markers selected from the group consisting of Ki-67, AgNOR, choline, claspin, cyclin A, CYR61, Cdk1, Histone H3, HsMCM2, IL-2, Ki-S1, Ki-S2, Ligl, MCM2, MCM6, MCM7, mitosin, p120, PCNA, PDPK, PLK, STK1, TK-1, topoisomerase II alpha, TPS.

The term "cancer" or hyperproliferative disease as used herein refers to tumor diseases and/or cancer, such as metastatic or invasive cancers, for example lung cancer, non small cell lung (NSCL) cancer, bronchioloalviolar cell lung cancer, bone cancer, pancreatic cancer, skin cancer, cancer of the head or neck, cutaneous or intraocular melanoma, rectal cancer, cancer of the anal region, stomach cancer, gastric cancer, colon cancer, colorectal cancer, cancer of the small intestines, esophageal cancer, liver cancer, pancreas cancer, breast cancer, ovarian cancer, uterine cancer, carcinoma of the fallopian tubes, carcinoma of the endometrium, carcinoma of the cervix, carcinoma of the vagina, carcinoma of the vulva, Hodgkin's Disease, cancer of the endocrine system, cancer of the thyroid gland, cancer of the parathyroid gland, cancer of the adrenal gland, sarcoma of soft tissue, cancer of the urethra, cancer of the penis, prostate cancer, bladder cancer, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, or cancer of unknown origin, or other hyperplastic or neoplastic CAIX related condition, including refractory versions of any of the above cancers or a combination of one or more of the above cancers or hyperproliferative diseases. Non-limiting examples of CAIX related conditions are cancers selected from the group consisting of kidney cancer, lung cancer, colon cancer, breast cancer, cervical cancer, bladder cancer, ovarian cancer, vulval cancer, brain cancer, head and neck cancer, soft tissue sarcoma, astrocytomas, cancer of the oral cavity and any cancer manifested by solid tumors with hypoxia and CAIX expression.

In a related aspect, there is provided a method of detecting CAIX, comprising providing a sample suspected to contain CAIX, contacting said sample with a CAIX binding polypeptide, fusion protein, conjugate or a composition as described herein, and detecting the binding of the CAIX binding polypeptide, fusion protein, conjugate or composition to indicate the presence of CAIX in the sample. In one embodiment, said method further comprises an intermediate washing step for removing non-bound polypeptide, fusion protein, conjugate or composition, after contacting the sample.

In one embodiment, there is provided a method, such as a diagnostic or prognostic method, for determining the presence of CAIX in a subject, the method comprising the steps:

contacting the subject, or a sample isolated from the subject, with a CAIX binding polypeptide, fusion protein, conjugate or a composition as described herein, and obtaining a value corresponding to the amount of the CAIX binding polypeptide, fusion protein, conjugate or composition that has bound in said subject or to said sample.

In one embodiment, said method further comprises an intermediate washing step for removing non-bound polypeptide, fusion protein, conjugate or composition, after contacting the subject or sample and before obtaining a value.

In one embodiment, said method further comprises a step of comparing said value to a reference. Said reference may be scored by a numerical value, a threshold or a visual indicator, for example based on a color reaction. The skilled person will appreciate that different ways of comparison to a reference are known in the art may be suitable for use.

In one embodiment of such a method, said subject is a mammalian subject, such as a human subject.

In one embodiment, said method is performed in vivo.

In one embodiment, said method is performed in vitro.

In a related aspect, there is provided a method of treatment of a CAIX related condition, comprising administering to a subject in need thereof an effective amount of a CAIX binding polypeptide, fusion protein, conjugate or composition as described herein. Consequently, in the method of treatment, the subject is treated with a CAIX binding polypeptide or a CAIX binding combination according to the invention. In a more specific embodiment of said method, the CAIX binding polypeptide, fusion protein, conjugate or composition as described herein modulates CAIX function in vivo.

In one embodiment, said CAIX related condition is cancer, such as a cancer selected from the group consisting of kidney cancer, lung cancer, colon cancer, breast cancer, cervical cancer, bladder cancer, ovarian cancer, vulval cancer, brain cancer, head and neck cancer, soft tissue sarcoma, astrocytomas, cancer of the oral cavity and any cancer manifested by solid tumors with hypoxia and CAIX expression.

While the invention has been described with reference to various exemplary aspects and embodiments, it will be understood by those skilled in the art that various changes may be made and equivalents may be substituted for elements thereof without departing from the scope of the invention. In addition, many modifications may be made to adapt a particular situation or molecule to the teachings of the invention without departing from the essential scope thereof. Therefore, it is intended that the invention not be limited to any particular embodiment contemplated, but that the invention will include all embodiments falling within the scope of the appended claims.

BRIEF DESCRIPTION OF THE FIGURES

FIG. 1A-1M is a listing of the amino acid sequences of examples of CAIX binding motifs comprised in CAIX binding polypeptides of the invention (SEQ ID NO:1-113 and SEQ ID NO:340-344), examples of 49-mer CAIX binding polypeptides according to the invention (SEQ ID NO:114-226 and SEQ ID NO:345-349), examples of 58-mer CAIX binding polypeptides according to the invention (SEQ ID NO:227-339, SEQ ID NO:350-354 and SEQ ID NO:365-368) as well as the amino acid sequences of Z-variants Z03639, Z03638, Z01155, Z08693, Z01157 (SEQ ID NO:355-359) and that of CAIX (SEQ ID NO:360) used for selection, screening and characterization for illustration of the invention.

FIG. 6A-6D shows the confirmation of binding specificity of $^{99m}Tc$-$(HE)_3$-Z09781 (A), $^{99m}Tc$-$(HE)_3$-Z09782 (B), $^{99m}Tc$-$(HE)_3$-Z09783 (C), and $^{99m}Tc$-$(HE)_3$-Z09784 (D) to the CAIX-expressing cell line SK-RC-52, determined as described in Example 7. Cell-associated radioactivity was calculated as percentage of total added radioactivity.

EXAMPLES

Summary

Figure 2:
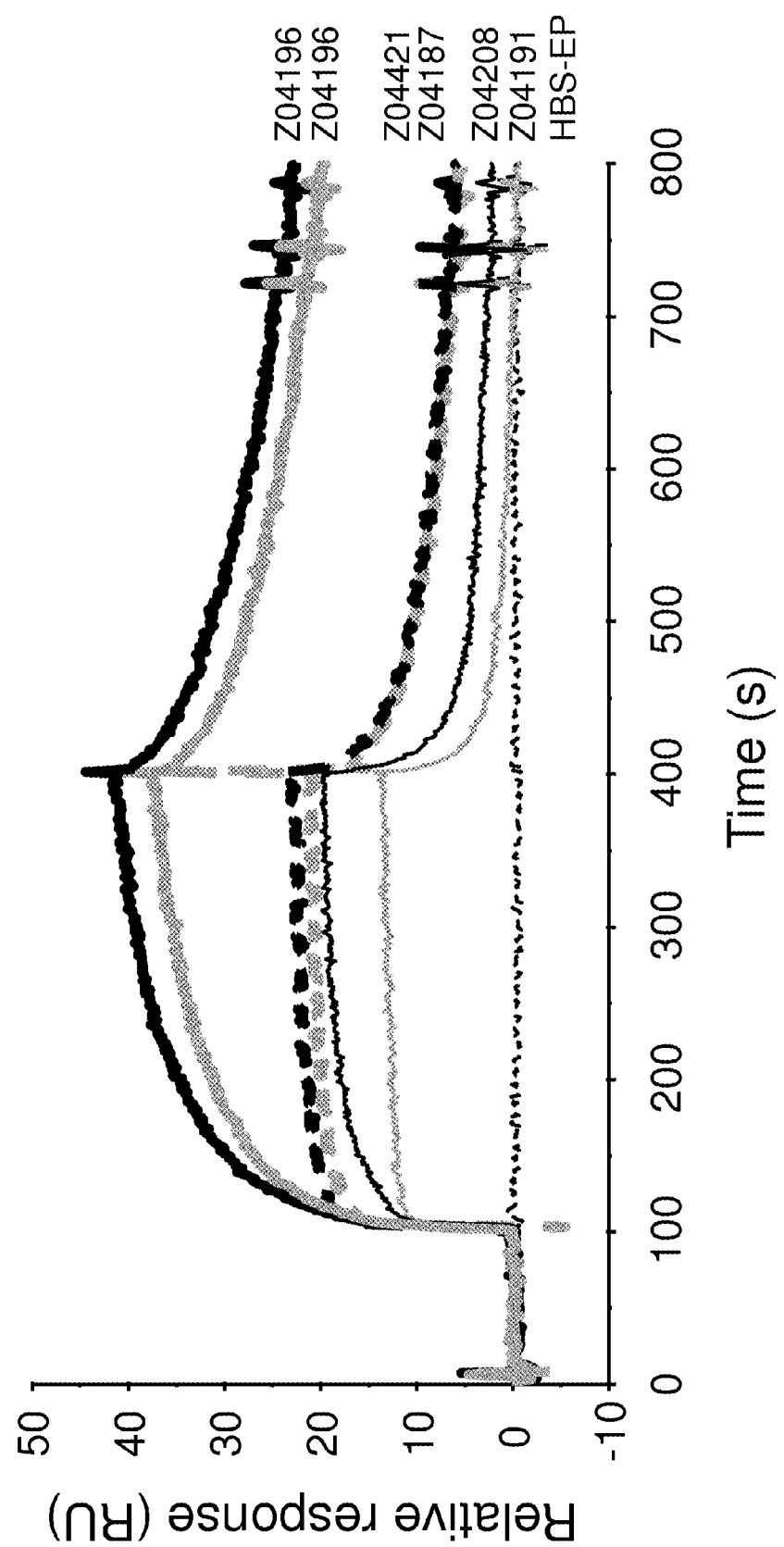
FIG. 2 shows the result of binding analysis performed in a Biacore instrument as described in Example 2. Sensorgrams were obtained by injection of the indicated Z variants (in $His_6$-$(Z\#\#\#\#\#)_2$-Cys format) Z04187 (SEQ ID NO:350), Z04191 (SEQ ID NO:351), Z04196 (SEQ ID NO:352), Z04208 (SEQ ID NO:353), Z04421 (SEQ ID NO:354) and HBS-EP over human CAIX (SEQ ID NO:360) immobilized on a surface on a CM5 chip.

The following Examples disclose the development of novel Z variant molecules targeted to carbonic anhydrase IX (CAIX) based on phage display technology. The CAIX binding polypeptides described herein were sequenced, and their amino acid sequences are listed in FIG. 1 with the sequence identifiers SEQ ID NO:227-339, SEQ ID NO:350-354 and SEQ ID NO:365-368. Also, the deduced binding motifs of these selected binding variants are listed in FIG. 1 with sequence identifiers SEQ ID NO:1-113 and SEQ ID NO:340-344.

The following materials where used throughout this work except where otherwise noted:
*Escherichia coli* strain RRIΔM15 (Rüther, Nucleic Acids Res 10:5765-5772, 1982)
*Escherichia coli* strain XL1-Blue (Agilent Technologies, cat. no. 200268)
Human CAIX (R&D Systems, cat. no. 2188-CA)

Example 1

Selection and Screening of CAIX Binding Z Variants

Materials and Methods
Biotinylation of Target Protein:
Human CAIX was subjected to a buffer exchange to phosphate buffered saline (PBS, 10 mM phosphate, 137 mM NaCl, 2.68 mM KCl, pH 7.4) using a dialysis cassette (Slide-a-lyzer 3.5 K, 3500 MWCO, Pierce, cat. no. 66333) according to the manufacturer's instructions.

Human CAIX was biotinylated according to the manufacturer's recommendations at room temperature (RT) for 30 min using No-Weigh EZ-Link Sulfo-NHS-LC-Biotin (Pierce, cat. no. 21327) at a 20× molar excess. Subsequent buffer exchange to PBS was performed as described above according to the manufacturer's instructions.

Phage Display Selection of CAIX Binding Z Variants:
A library of random variants of protein Z displayed on bacteriophage, constructed in phagemid pAY02047 essentially as described in Grönwall et al (J Biotechnol, 128:162-183, 2007), were used to select CAIX binding polypeptides. The library, Zlib004Naive.I, utilizes the Taq DNA polymerase binding molecule Z03639 (SEQ ID NO:346) (described in Gunneriusson et al, Protein Eng 12:873-878, 1999, where it was denoted $Z_{TaqS1-1}$) as fusion partner. The library had an actual size of $1.4 \times 10^{10}$ variants.

Phage stocks were prepared in a 20 l fermenter. Cells from a glycerol stock containing the phagemid library Zlib004Naive.I were inoculated in 20 l of TSB-YE (Tryptic Soy Broth-Yeast Extract; 30 g/l TSB, 5 g/l yeast extract) supplemented with 2% glucose and 100 μg/ml ampicillin. The cultivations were grown at 37° C. in a fermenter (Belach Bioteknik, BR20). When the cells reached an optical density (OD) of 0.7-0.8, approximately 2.6 l of the cultivation was infected using a 10× molar excess of M13K07 helper phage (New England Biolabs, cat. no. N0315S). The cells were incubated for 30 min, whereupon the fermenter was filled up to 20 l with TSB-YE supplemented with 0.1 mM IPTG (isopropyl-β-D-1-thiogalactopyranoside, for induction of expression), 25 μg/ml kanamycin and 12.5 μg/ml carbenicillin, and cells were grown at 30° C. for 22 h. The cells in the cultivation were pelleted by centrifugation at 15,900 g and the phage particles remaining in the medium were precipitated twice in PEG/NaCl (polyethylene glycol/sodium chloride), filtered and dissolved in PBS and glycerol as described in Grönwall et al, supra. Phage stocks were stored at −80° C. before use.

Selections were performed in five cycles against biotinylated human CAIX divided in two different tracks. Phage stock preparation, selection procedure and amplification of phage between selection cycles were performed essentially as described for selection against another target in WO2009/077175. PBS supplemented with 0.1% gelatine and 0.1% Tween20 was used as selection buffer during first 4 cycles and PBS supplemented with 0.1% gelatine and 0.5% Tween20 during the 5$^{th}$ cycle. In order to reduce the amount of background binders, pre-selection was performed by incubation of phage stock with DYNABEADS M-280 Streptavidin (SA-beads, Dynal, cat. no. 112.06) for 1 hour at RT. All tubes and beads used in the selection were pre-blocked with selection buffer. Selection was performed in solution in RT followed by catch of target-phage complexes on SA-beads where 1 mg beads per 4 μg biotinylated CAIX was used. *E. coli* strain RRIΔM15 was used for phage amplification. In cycle 1 of the selections, 100 nM was used, and two washes with PBST 0.1% (PBS supplemented with 0.1% Tween-20) were performed where the first one lasted for 25 min and the second 1 min. An increased stringency, using a lowered target concentration and an increased number of washes, was applied in the subsequent cycles. In cycle 2, 50 nM biotinylated CAIX was used and in cycle 3-5, 20 nM biotinylated CAIX was used. In cycle 2, 3 and 4; 2 or 4, 4 or 8, 5 or 12 washes were performed, respectively, using PBST 0.1%. In the last and 5$^{th}$ cycle, 3 washes were performed during 2 min followed by 1 wash during 7 min and at last 1 wash during 2 min, all using PBST 0.5%. After the wash, the bound phages were eluted with 500 μl 0.1 M glycine-HCl, pH 2.2 followed by immediate neutralization with 50 μl 1 M Tris-HCl, pH 8.0 and 450 μl PBS.

ELISA Screening of Z Variants:
To verify that the selected Z variant molecules could indeed interact with CAIX, an ELISA assay was performed. The Z variants were produced by inoculating single colonies from the selections into 1 ml TSB-YE medium supplemented with 100 μg/ml ampicillin and 0.1 mM IPTG in deep-well plates (Nunc, cat. no. 278752). The plates were incubated for 18-24 h at 37° C. Cells were pelleted by centrifugation, re-suspended in 400 μl PBST 0.05% and frozen at −80° C. to release the periplasmic fraction of the cells. Frozen samples were subsequently thawed in a water bath and cells were pelleted by centrifugation. The periplasmic supernatant contained the Z variants as fusions to the Taq DNA polymerase binding molecule Z03639, expressed as AQHDEALE-[Z#####]-VDYV-[Z03639]-YVPG (SEQ ID NO. 387). Z##### refers to individual, 58 amino acid residue Z variants.

Half-area 96-well ELISA plates (Costar, cat. no. 3690) were coated with 50 μl/well of coating buffer (50 mM sodium carbonate, pH 9.6) containing 1 μg/ml of a Z variant molecule specific for Z03639 (His$_6$-(Z01157)$_2$) and incubated over-night at 4° C. The solution was poured off and the wells were blocked with 100 μl of PBS-T 0.1 supplemented with 2% non-fat dry milk solution (Semper AB) for 1 h at RT under slow shaking. The blocking solution was discarded and 50 μl periplasmic solution was added to the wells and incubated for 1.5 h at RT under slow shaking. The supernatants were poured off and the wells were washed 4 times with PBST 0.05%. Then, 50 μl of biotinylated human CAIX at a concentration of 0.5 or 1 μg/ml in PBST 0.05 was added to each well. The plates were incubated for 1.5 h at RT followed by washes as described above. Streptavidin-HRP (Horseradish peroxidase; Dako, cat. no. P0397) diluted 1:5,000 in PBST 0.05%, was added to the wells and the plates were incubated for 1 h. After washing as described above, 50 μl ImmunoPure TMB substrate (Pierce, cat. no. 34021) was added to the wells and the plates were treated according to the manufacturer's recommendations. All steps from blocking to reading were performed in a Tecan Genesis Freedom 200 robot (Tecan Group LTD). Absorbance of the wells was read at 450 nm in an ELISA reader Tecan Ultra 384 (Tecan) and evaluated with Magellan v. 5.0 software (Tecan).

As negative control, PBST 0.05% was used instead of the periplasmic fraction followed by the biotinylated CAIX. Sequencing was performed for the clones with positive absorbance values against biotinylated human CAIX.

Sequencing:

Based on the ELISA screening, a part of all clones regarded as positive were picked for sequencing. PCR fragments were amplified in two steps from single colonies using a standard PCR program and the primers AFFI-21 (5'-tgcttccggctcgtatgttgtgtg; SEQ ID NO:361) and AFFI-22 (5'-cggaaccagagccaccaccgg; SEQ ID NO:362). Sequencing of amplified fragments was performed using the biotinylated oligonucleotide AFFI-72 (5'-biotin-cggaaccagagccaccac-cgg; SEQ ID NO:363) and a BIGDYE Terminator v3.1 Cycle Sequencing Kit (Applied Biosystems, cat. no. 4336919), used in accordance with the manufacturer's protocol. The sequencing reactions were purified by binding to magnetic streptavidin coated beads (Detach Streptavidin Beads, Nordiag, cat. no. 2012-01) using a Magnatrix 8000 (NorDiag), and analyzed on ABI PRISM 3100 Genetic Analyzer (PE Applied Biosystems). The sequencing results were imported and analyzed with an ALD LIMS NAUTI-LUS 2003 R2 B3 software (Thermo Electronics Corp.).

Results

Phage Display Selection of CAIX Binding Z Variants:

Individual clones were obtained after four and five cycles of phage display selections against biotinylated human CAIX.

ELISA Screening of Z Variants:

The clones obtained after four and five cycles of selection were produced in 96-well plates and screened for human CAIX binding activity in ELISA. All clones giving a response with signals corresponding to at least 2× the negative control were considered as positive binders to CAIX.

Sequencing:

Sequencing was performed for the clones with positive absorbance values against CAIX in the ELISA screening. Each variant was given a unique identification number #####, and individual variants are referred to as Z#####. The amino acid sequences of the 58 amino acid residues long Z variants are listed in FIG. 1A-1L and in the sequence listing as SEQ ID NO:350-354. The deduced CAIX binding motifs of these Z variants are listed in FIG. 1A-1L and in the sequence listing as SEQ ID NO:340-344. The amino acid sequences of the 49 amino acid residues long polypeptides predicted to constitute the complete three-helix bundle within each of these Z variants are listed in FIG. 1A-1L and in the sequence listing as SEQ ID NO:345-349.

Example 2

Production and Characterization of CAIX Binding Z Variants

Materials and Methods

Subcloning of Z Variants:

The DNA of five CAIX binding Z variants, Z04187 (SEQ ID NO:350), Z04191 (SEQ ID NO:351), Z04196 (SEQ ID NO:352), Z04208 (SEQ ID NO:353), and Z04421 (SEQ ID NO:354), were amplified from the library vector pAY02047. A subcloning strategy for construction of dimeric Z variant molecules with N-terminal $His_6$ tag and C-terminal Cys was applied using standard molecular biology techniques and as described in detail in WO 2009/077175 for Z variants binding another target. The Z gene fragments were sub-cloned into the expression vector pAY01449 resulting in the encoded sequence MGSSHHHHHHLQ-[Z#####][Z#####]-VDC (SEQ ID NO: 388).

Cultivation and Purification:

*E. coli* BL21(DE3) cells (Novagen) were transformed with plasmids containing the dimeric gene fragment of each respective CAIX binding Z variant and cultivated at 37° C. in 800 ml of TSB-YE medium supplemented with 50 μg/ml kanamycin. At OD600=2, IPTG was added to induce protein expression at a final concentration of 0.5 mM and the cultivation was incubated at 37° C. for another 5 h. The cells were harvested by centrifugation.

Approximately 1.5 g of each cell pellet was re-suspended in 35 ml of binding buffer (20 mM sodium phosphate, 0.5 M NaCl, 20 mM imidazole, pH 7.4) supplemented with 29 U/ml BENZONASE (Merck, cat. no. 1.01654.0001) and the cells were disrupted by ultrasonication. Cell debris was removed by centrifugation and each supernatant was applied on a 1 ml His GraviTrap IMAC column (GE Healthcare, cat. no. 11-0033-99). Contaminants were removed by washing with wash buffer (20 mM sodium phosphate, 0.5 M NaCl, 60 mM imidazole, pH 7.4) and the CAIX binding Z variants were subsequently eluted with elution buffer (20 mM sodium phosphate, 0.5 M NaCl, 500 mM imidazole, pH 7.4). A fraction, corresponding to approximately 1 mg, of each purified CAIX binding Z variant was reduced with the addition of 1 M DTT to a final concentration of 30 mM. The reduced dimers were transferred to 0.2 M sodium acetate, pH 5.5, by size exclusion chromatography. N-Ethylmaleim-ide (Pierce, cat. no. 23030) was added in a 10-fold molar excess to react with the C-terminal cysteine, and the dimers were then transferred to PBS (2.68 mM KCl, 0.47 mM $KH_2PO_4$, 137 mM NaCl, 8.1 mM $Na_2HPO_4$, pH 7.4.) by size exclusion chromatography. Protein concentrations were determined by measuring the absorbance at 280 nm, using a NANODROP ND-1000 spectrophotometer, and using the extinction coefficient of the respective protein. The purity of the CAIX binding Z dimers was analyzed by SDS-PAGE stained with Coomassie Blue. The identity of each purified CAIX binding Z dimer was confirmed using HPLC-MS analysis.

CD Analysis:

The purified Z variants in dimer format were thawed and diluted to 0.5 mg/ml in PBS. For each diluted Z variant, a CD spectrum at 250-195 nm was obtained at 20° C. In addition, a variable temperature measurement (VTM) was performed to determine the melting temperature (Tm). In the VTM, the absorbance was measured at 221 nm while the temperature was raised from 20 to 90° C., with a temperature slope of 5° C./min. The CD measurements were performed on a Jasco J-810 spectropolarimeter (Jasco Scandinavia AB) using a cell with an optical path-length of 1 mm.

Biacore Binding Analysis:

The interactions of five NEM treated $His_6$-tagged dimeric CAIX-binding Z variants with human CAIX were analyzed in a Biacore 2000 instrument (GE Healthcare). Human CAIX was immobilized in a flow cell on the carboxylated dextran layer of a CM5 chip surface (GE Healthcare). The immobilization was performed using amine coupling chemistry according to the manufacturer's protocol. One flow cell surface on the chip was activated and deactivated for use as blank during analyte injections. The analytes, i.e. dimeric Z variants diluted in HBS-EP running buffer (GE Healthcare) to a final concentration of 1 μM, were injected at a flow-rate of 10 µl/min for 5 minutes. After 5 minutes of dissociation, the surfaces were regenerated with one injection of 10 mM HCl. The results were analyzed in BiaEvaluation software (GE Healthcare). Curves of the blank surface were subtracted from the curves of the ligand surface.

Immunofluorescence Staining for Flow Cytometry Analysis:

Colorectal carcinoma cells LS174T, expressing CAIX on their surface, were cultured in EMEM (Lonza) supplemented with 10% fetal calf serum (FCS), 1% glutamine, 1% non-essential amino acids, 1% sodium pyruvate and 1% Penicillin-Streptomycin (PEST). On the day of assay, LS174T cells were trypsinated, counted and $0.1$–$0.2 \times 10^6$ cells were added to 5 ml falcon tubes. The cells were pelleted by centrifugation at 1200 rpm and supernatant removed. The cells were stained with different purified Z variants in $His_6$-(Z#####)$_2$-Cys-NEM form. For screening, 100 µl of the different binders diluted to 10 µg/ml in PBS supplemented with 2% FCS (PBS 2% FCS) was added and cells were incubated for two hours at 4° C. PBS was used as background control and an unrelated Z variant (Z03638 (SEQ ID NO:356)) was used as negative control. The cells were washed once by filling up the tube with PBS and pelleting the cells by centrifugation. The pelleted cells were resuspended in 100 µl of goat anti-Z variant Ig (cat. no. 20.1000.01.0005; Affibody AB, Sweden), 5 µg/ml and incubated for one hour at 4° C. The goat anti-CAIX specific antibody MAB2188 (R&D systems) was used as a positive control at a concentration of 5 µg/ml. Cells were subsequently washed in PBS as described and resuspended in 100 µl of Alexa488-labeled anti-goat antibody (Invitrogen) at a concentration of 10 µg/ml. After 45 minutes of incubation at 4° C. cells were washed in PBS, resuspended in 300 µl of PBS and subjected to flow cytometry analysis using a FACSCantoII (BD Biosciences).

After the flow cytometry analysis, cells were added to glass slides and fixed in 2% formaldehyde in PBS for 15 minutes at RT. After washing carefully in PBS, the slides were dried and mounted with anti-fading solution (Vectashield, Vector laboratories). The staining was analyzed with a Leica DM-LA UV microscope (Leica Microsystems).

Results

Cultivation and Purification:

The five CAIX binding Z variants, Z04187, Z04191, Z04196, Z04208 and Z04421, constructed as dimers and with an N-terminal $His_6$-tag and a C-terminal Cys, expressed well in *E. coli*. The amount of IMAC-purified protein from approximately 1.5 g bacterial pellets, determined spectrophotometrically by measuring the absorbance at 280 nm, ranged from 15 mg to 24 mg for the different CAIX binding Z dimers.

SDS-PAGE analysis of each final protein preparation showed that these predominantly contained respective CAIX binding Z dimer. The correct molecular weight of each CAIX binding Z variant was confirmed by HPLC-MS analysis.

CD Analysis:

The CD spectrums showed that the Z variant molecules had a helical structures at 20° C. This result was also verified in the variable temperature measurements where the melting temperatures (Tm) were determined (Table 1).

TABLE 1

Melting temperatures for a selection of Z variants.

| Z variant | Tm (° C.) |
|---|---|
| $His_6$-(Z04187)$_2$-Cys-NEM | 51 |
| $His_6$-(Z04191)$_2$-Cys-NEM | 60 |
| $His_6$-(Z04196)$_2$-Cys-NEM | 61 |
| $His_6$-(Z04208)$_2$-Cys-NEM | 62 |
| $His_6$-(Z04421)$_2$-Cys-NEM | 51 |

Biacore Binding Analysis:

The binding of five dimeric Z variants (Z04187, Z04191, Z04196, Z04208 and Z04421) to human CAIX was tested in a Biacore instrument by injecting the Z variants over a surface containing CAIX. The ligand immobilization level on the surface was 590 RU human CAIX. All tested Z variants showed binding to CAIX. The resulting curves are displayed in FIG. 2, where Z04196 showed the slowest dissociation curve to human CAIX.

Figure 3:
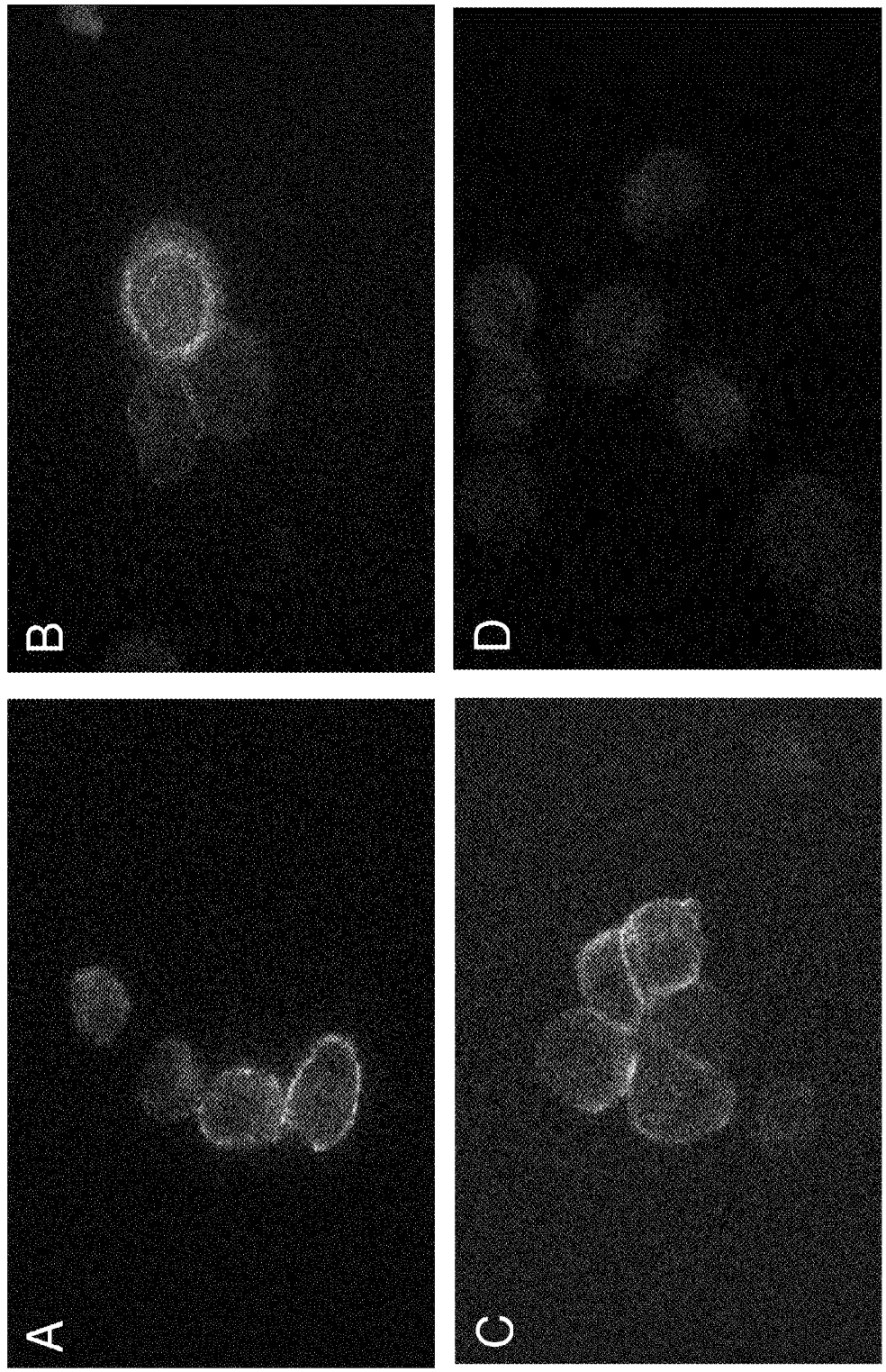
FIG. 3 shows the result of immunofluorescence staining of CAIX on LS174T cells as described in Example 2. The cells were stained with $His_6$-$(Z04421)_2$-Cys-NEM (A), $His_6$-$(Z04187)_2$-Cys-NEM (B), $His_6$-$(Z04208)_2$-Cys-NEM (C) and negative Z variant $His_6$-Z01155-Cys-NEM (D). The resulting images show membrane specific staining on LS174T cells.

Immunofluorescence Staining for Flow Cytometry Analysis:

LS174T cells were stained with the primary binders $His_6$-(Z04187)$_2$-Cys-NEM, $His_6$-(Z04191)$_2$-Cys-NEM, $His_6$-(Z04196)$_2$-Cys-NEM, $His_6$-(Z04208)$_2$-Cys-NEM and $His_6$-(Z04421)$_2$-Cys-NEM. A CAIX specific antibody was included as a positive control. All binders were positive in the flow cytometry analysis with a shift in mean fluorescence intensity (MFI). Examination of the cells by fluorescence microscopy showed a membrane specific staining on LS174T cells with varying intensity. FIG. 3 shows membrane staining with $His_6$-(Z04187)$_2$-Cys-NEM, $His_6$-(Z04208)$_2$-Cys-NEM and $His_6$-(Z04421)$_2$-Cys-NEM. An unrelated Z variant in monomer format, $His_6$-Z01155-Cys-NEM (SEQ ID NO:357), was used as negative control (FIG. 3).

Example 3

Design and Construction of a Maturated Library of CAIX Binding Z Variants

In this Example, a maturated library was constructed. The library was used for selections of CAIX binding polypeptides. Selections from maturated libraries are usually expected to result in binders with increased affinity (Orlova et al Cancer Res 2006, 66(8):4339-48). In this study, randomized double stranded linkers were generated by the SLONOMICS technology, which enables incorporation of randomized sets of trinucleotide building blocks using ligations and restrictions of the subsequently built up double stranded DNA.

Materials and Methods

Library design: The library was based on a selection of sequences of the human CAIX binding Z variants described in Examples 1 and 2. In the new library, 13 variable positions in the Z molecule scaffold were biased towards certain amino acid residues, according to a strategy mainly based on the Z variant sequences defined in SEQ ID NO:350-354 (Z04187, Z04191, Z04196, Z04208 and Z04421). A SLONOMAX library of double-stranded DNA, containing the 147 bp partially randomized helix 1 and 2 of the amino acid sequence 5'-AA ATA AAT CTC GAG GTA GAT GCC AAA TAC GCC AAA GAR NNN NNN NNN GCR NNN NNN GAR ATY NNN NNN YTR CCT AAC TTA ACS NNN NNN CAR NNN NNN GCM TTC ATC NNN AAA TTA TGG GAT GAC CCA AGC CAG AGC TCA TTA TTT A-3' (SEQ ID NO:364; randomized codons are illustrated as NNN) flanked with restriction sites XhoI and SacI, was ordered from Sloning BioTechnology GmbH (Pucheim, Germany). The theoretical distributions of amino acid residues in the new library including 12 variable Z positions are given in Table 2.

TABLE 2

Library design.

| Amino acid position in the Z variant molecule | Randomization (amino acid abbreviations) | No of amino acids | Proportion |
|---|---|---|---|
| 9 | N, D, Q, E, H, W | 6 | 1/6 |
| 10 | A, R, N, D, Q, E, G, H, I, L, F, S, T, W, Y, V | 16 | 1/16 |
| 11 | A, N, F, W, Y | 5 | 1/5 |
| 13 | A, G, S, W | 4 | 1/4 |
| 14 | A, R, N, D, Q, E, G, H, I, L, F, S, T, W, Y, V | 16 | 1/16 |
| 17 | A, R, N, D, Q, E, G, H, I, L, F, S, T, W, Y, V | 16 | 1/16 |
| 18 | R, D, E, S | 4 | 1/4 |
| 24 | A, R, N, D, Q, E, G, H, I, L, F, S, T, W, Y, V | 16 | 1/16 |
| 25 | A, R, N, D, Q, E, G, H, I, L, F, S, T, W, Y, V | 16 | 1/16 |
| 27 | R, Q | 2 | 1/2 |
| 28 | N, D, Q, E, H | 5 | 1/5 |
| 32 | F, Y | 2 | 1/2 |

Library Construction:

The library was amplified using Ampli Taq Gold polymerase (Applied Biosystems, cat. no. 4311816) during 12 cycles of PCR and pooled products were purified with QIAquick PCR Purification Kit (QIAGEN, cat. no. 28106) according to the supplier's recommendations. The purified pool of randomized library fragments was digested with restriction enzymes XhoI and SacI (New England Biolabs, cat. no. R0146L, and cat. no. R0156L) and concentrated using a PCR Purification Kit. Subsequently, the product was run on a preparative 1% agarose gel electrophoresis and purified using QIAGEN gel extraction Kit (QIAGEN, cat. no. 28706) according to the supplier's recommendations.

The phagemid vector pAY02592 (essentially as pAffi1 described in Grönwall et al supra) was restricted with the same enzymes, purified using phenol/chloroform extraction and ethanol precipitation. The restricted fragments and the restricted vector were ligated in a molar ratio of 5:1 with T4 DNA ligase (New England Biolabs, cat. no. M0202S) for 2 hours at RT, followed by overnight incubation at 4° C. The ligated DNA was recovered by phenol/chloroform extraction and ethanol precipitation, followed by dissolution in 10 mM Tris-HCl, pH 8.5. Thus, the resulting library vector pAY02592 encoded a library of Z variants each fused to an albumin binding domain (ABD) derived from streptococcal protein G.

The ligation reactions (approximately 150 ng DNA/transformation) were electroporated into electrocompetent E. coli RRIΔM15 cells (100 μl). Immediately after electroporation, approximately 1 ml of SOC medium (TSB-YE media, 1% glucose, 50 μM MgCl$_2$, 50 μM MgSO$_4$, 50 μM NaCl and 12.5 μM KCl) was added. The transformed cells were incubated at 37° C. for 50 min. Samples were taken for titration and for determination of the number of transformants. The cells were thereafter pooled and cultivated overnight at 36° C. in 10 l of TSB-YE medium, supplemented with 2% glucose and 100 μg/ml ampicillin. The cells were pelleted for 15 min at 4,000 g and resuspended in a PBS/glycerol solution (approximately 40% glycerol). The cells were aliquoted and stored at −80° C. Clones from the library of Z variants were sequenced in order to verify the content and to evaluate the outcome of the constructed library vis-à-vis the library design. Sequencing was performed as described in Example 1 and the amino acid distribution was verified.

Preparation of Phage Stock:

Phage stock containing the phagemid library was prepared in a 20 l fermenter. Cells from a glycerol stock containing the phagemid library were inoculated in 20 l of a defined proline free medium [dipotassium hydrogenphosphate 7 g/l, trisodium citrate dihydrate 1 g/l, uracil 0.02 g/l, YNB (Difco™ Yeast Nitrogen Base w/o amino acids, Becton Dickinson) 6.7 g/l, glucose monohydrate 5.5 g/l, L-alanine 0.3 g/l, L arginine monohydrochloride 0.24 g/l, L-asparagine monohydrate 0.11 g/l, L cysteine 0.1 g/l, L-glutamic acid 0.3 g/l, L-glutamine 0.1 g/l, glycine 0.2 g/l, L-histidine 0.05 g/l, L-isoleucine 0.1 g/l, L-leucine 0.1 g/l, L-lysine monohydrochloride 0.25 g/l, L-methionine 0.1 g/l, L-phenylalanine 0.2 g/l, L serine 0.3 g/l, L-threonine 0.2 g/l, L-tryptophane 0.1 g/l, L-tyrosine 0.05 g/l, L-valine 0.1 g/l] supplemented with 100 μg/ml ampicillin. The cultivations were grown at 37° C. in a fermenter (Belach Bioteknik, BR20) until OD600 reached 0.75. All the following steps were performed as described in Example 1 for the library Zlib004Naive.I. After cultivation, the cells were pelleted by centrifugation at 15,900 g and the phage particles remaining in the medium were thereafter precipitated twice in PEG/NaCl, filtered and dissolved in PBS and glycerol as described in Example 1. Phage stocks were stored at −80° C. until use in selection.

Results

Library Construction:

The new library was designed based on a set of CAIX binding Z variants with verified binding properties (Example 1 and 2). The theoretical size of the designed library was 1.0×10$^{10}$ Z variants. The actual size of the library, determined by titration after transformation to E. coli. RRIΔM15 cells, was 1.3×10$^{10}$ transformants.

The library quality was tested by sequencing of 94 transformants and by comparing their actual sequences with the theoretical design. The contents of the actual library compared to the designed library were shown to be satisfying. The locked position in the designed amino acid sequence (W in position 35) was reflected in the actual sequence in that only the expected amino acid occurred in that position. A maturated library of potential binders to human CAIX binding polypeptides was thus successfully constructed.

Example 4

Selection, Screening and Characterization of Z Variants from a Maturated Library Materials and Methods Phage Display Selection of CAIX Binding Polypeptides:

The target protein human CAIX was biotinylated as described in Example 1. Phage display selections were performed against CAIX essentially as described in Example 1 using the new library of Z variant molecules described in Example 3. E. coli XL1-Blue was used for phage amplification in the first cycle and RRIΔM15 in the following cycles. Selection was initially performed in two parallel tracks. In one track, the time of selection was 2-3 h, while in the other track, 10 min selection time was used. In the latter track, the target was immobilized on SA-beads before selection. These two tracks (1 and 2) were further divided in the second cycle, resulting in totally six tracks (1a-c and 2a-c), differing in target concentration and wash conditions. Selection was performed in a total of four cycles in PBST 0.1% supplemented with 3% Bovine serum albumin (BSA). In cycle 1 of the selections, 50 nM human CAIX was used and three washes with PBST 0.1% were performed. An increased stringency, using a lowered target concentration and an increased number of washes, was applied in the subsequent three cycles. In cycle 2 and 3; 13, 13, or 10 nM CAIX were used and in cycle 4; 4.4, 4.4 or 0.5 nM CAIX were used. In cycle 2 and 3: 6, 11 or 11 washes were performed; in cycle 4; 9, 18 or 18 washes were performed using PBST 0.1%.

Sequencing of Potential Binders:

Individual clones from the different selection tracks were picked for sequencing. All clones run in the ELISA screening were sequenced. Amplification of gene fragments and sequence analysis of gene fragments were performed essentially as described in Example 1.

ELISA Screening of Z Variants:

Single colonies containing Z variants (expressed as Z variant ABD fusion proteins as described in Example 3) were randomly picked from the selected clones of the CAIX maturated library and grown in 1 ml cultivations as described in Example 1. Periplasmic proteins were released by 6 repeated freeze-thawing cycles. ELISA screenings were performed essentially as described in Example 1 with the following exceptions. Half-area 96-well ELISA plates were coated with 2 µg/ml of an ABD specific goat antibody (produced in-house) diluted in coating buffer. The antibody solution was poured off and the wells were blocked with 100 µl of PBSC (PBS supplemented with 0.5% casein; Sigma, cat. no. C8654) for 1.5 h at RT. Biotinylated human CAIX was used at a concentration of 0.25 µg/ml (6 nM) diluted in PBSC and incubation was performed for 1 h. Streptavidin conjugated HRP was obtained from Thermo Scientific (cat. no. N100) and diluted 1:30,000 in PBSC before addition to the wells and incubated for 45 min. After washing as described above, 50 µl ImmunoPure TMB substrate (Thermo Scientific, cat. no. 34021) was added to the wells and the plates were treated according to the manufacturer's recommendations. Absorbance of the wells was measured at 450 nm using a multi-well plate reader, Victor³ (Perkin Elmer). A Z variant binding an irrelevant protein was used as negative control and a blank was created by omitting the periplasmic step.

ELISA $K_D$ Analysis of CAIX Binders:

A selection of CAIX binders was subjected to an analysis of the response against a dilution series of biotinylated human CAIX using ELISA as described above. All periplasm samples were diluted 1:1 in PBST 0.05%. Biotinylated protein was added at a concentration of 1 µg/ml (24 nM) and diluted stepwise 1:5 down to 1.6 ng/ml (38 pM). All Z variants were also assayed with no target protein added as a background control. A periplasm sample containing no Z variant was also included as a negative control. Obtained values were analyzed using GraphPad Prism 5 and non-linear regression.

Results

Phage Display Selection of CAIX Binding Polypeptides:

Selection was performed in totally six parallel tracks containing four cycles each. The different selection tracks differed in selection time, target concentration and wash conditions as follows: 1a) 2-3 h selection time, high concentration, few washes, 1 b) 2-3 h selection time, high concentration, intense wash, 1c) 2-3 h selection time, low concentration, intense wash, 2a) 10 min selection time, high concentration, few washes, 2b) 10 min selection time, high concentration, intense wash, and 2c) 10 min selection time, low concentration, intense wash. In each round all tracks gave sufficient amounts of phage particles in the eluate. Most phage particles were found in tracks 1a and b, representing the highest target concentration and 2-3 h selection time.

Sequencing:

Randomly picked clones (279) were sequenced. Each individual Z variant was given an identification number, Z#####, as described in Example 1. In total, 113 new unique Z variant molecules were identified. Among the sequenced clones, 25 sequences occurred two or more times.

The amino acid sequences of the 58 amino acid residues long Z variants are listed in FIG. 1 and in the sequence listing as SEQ ID NO:227-339. The deduced CAIX binding motifs of these Z variants are listed in FIG. 1 and in the sequence listing as SEQ ID NO:1-113. The amino acid sequences of the 49 amino acid residues long polypeptides predicted to constitute the complete three-helix bundle within each of these Z variants are listed in FIG. 1 and in sequence listing as SEQ ID NO:114-226.

ELISA Screening of Z Variants:

Clones obtained after four selection cycles were produced in 96-well plates and screened for human CAIX binding activity using ELISA. All randomly picked clones were analyzed. 113 of the 201 unique Z variants were found to give an approximately response of 3× the negative control or higher (0.3-3.0 AU) against human CAIX at a concentration of 0.25 µg/ml. Clones from all selection tracks showed positive signals. The negative controls had absorbances of approximately 0.1 AU.

ELISA $K_D$ Analysis of CAIX Binders:

A subset of Z variants was selected based on the result in the ELISA experiment described above (absorbance over 1.0 AU) and subjected to a target titration in ELISA format. Periplasma samples were incubated with a serial dilution of biotinylated CAIX. A periplasm sample with no Z variant was also assayed as a negative control. Obtained values were analyzed and their respective $K_D$ values were calculated (Table 3).

TABLE 3

Calculated $K_D$ values from ELISA titration analysis of Z variants.

| Z variant | SEQ ID NO: | $K_D$ ELISA |
| --- | --- | --- |
| Z06919 | 232 | 2.9E−09 |
| Z06920 | 268 | 8.0E−09 |
| Z06923 | 270 | 8.6E−09 |
| Z06924 | 241 | 6.7E−09 |
| Z06925 | 271 | 9.9E−09 |
| Z06931 | 276 | 6.1E−09 |
| Z06932 | 242 | 7.9E−09 |
| Z06933 | 243 | 4.3E−09 |
| Z06934 | 244 | 5.8E−09 |
| Z06936 | 227 | 1.8E−09 |
| Z06941 | 281 | Interrupted |
| Z06942 | 228 | 1.9E−09 |
| Z06943 | 245 | Ambiguous |
| Z06944 | 282 | 1.4E−08 |
| Z06949 | 284 | 1.4E−08 |
| Z06954 | 264 | 3.4E−09 |
| Z06955 | 286 | 7.7E−09 |
| Z06959 | 233 | 2.7E−09 |
| Z06960 | 265 | 3.9E−09 |

TABLE 3-continued

Calculated $K_D$ values from ELISA titration analysis of Z variants.

| Z variant | SEQ ID NO: | $K_D$ ELISA |
|---|---|---|
| Z06961 | 234 | 2.7E-09 |
| Z06962 | 235 | 2.9E-09 |
| Z06967 | 289 | 9.0E-09 |
| Z06971 | 246 | 5.9E-09 |
| Z06976 | 229 | 2.5E-09 |
| Z06977 | 266 | 4.1E-09 |
| Z06984 | 236 | 2.9E-09 |
| Z06985 | 247 | 3.7E-09 |
| Z06986 | 237 | 2.1E-09 |
| Z06993 | 248 | 6.5E-09 |
| Z06994 | 294 | 1.5E-08 |
| Z06996 | 296 | 1.0E-08 |
| Z06999 | 238 | 2.7E-09 |
| Z07000 | 249 | 5.8E-09 |
| Z07010 | 250 | 3.5E-09 |
| Z07012 | 251 | 4.0E-09 |
| Z07013 | 252 | 4.4E-09 |
| Z07022 | 304 | 1.1E-08 |
| Z07024 | 305 | 1.1E-08 |
| Z07034 | 310 | 9.4E-09 |
| Z07052 | 316 | 9.2E-09 |
| Z07064 | 253 | 6.1E-09 |
| Z07066 | 254 | 8.3E-09 |
| Z07072 | 255 | 8.4E-09 |
| Z07074 | 256 | 6.8E-09 |
| Z07077 | 257 | 3.6E-09 |
| Z07081 | 258 | 4.3E-09 |
| Z07082 | 259 | 5.2E-09 |
| Z07084 | 231 | 1.1E-08 |
| Z07087 | 325 | 1.2E-08 |
| Z07089 | 239 | 2.7E-09 |
| Z07090 | 260 | 4.0E-09 |
| Z07091 | 230 | 1.8E-09 |
| Z07095 | 267 | 4.5E-09 |
| Z07096 | 240 | 2.5E-09 |
| Z07100 | 261 | 6.4E-09 |
| Z07103 | 333 | 1.5E-08 |
| Z07104 | 262 | 4.3E-09 |
| Z07112 | 263 | 5.6E-09 |

Example 5

Subcloning, Production and Characterization of a Subset of CAIX Binding Z Variants Materials and Methods Subcloning of Z Variant Molecules into Expression Vectors:

Based on sequence analysis and the performance in the titration ELISA against human CAIX, 12 clones were selected for subcloning into the expression vector pAY01448. The best primary binder was included in the subcloning. Monomer Z variant fragments were amplified from the phagemid vector pAY02592 and the subcloning into pAY01448 was performed as described in Example 2, resulting in a vector encoding the protein sequence MGSSH-HHHHHLQ-[Z#####]-VD (SEQ ID NO. 389).

Protein Expression and Purification:

E. coli BL21(DE3) cells (Novagen) were transformed with plasmids containing the gene fragment of each respective CAIX-binding Z variant and cultivated at 37° C. in 800 ml of TSB-YE medium supplemented with 50 µg/ml kanamycin. At OD600=2, IPTG was added to induce protein expression at a final concentration of 0.17 mM and the cultivation was incubated at 37° C. for another 5 h. The cells were harvested by centrifugation.

Approximately 1.5 g of each cell pellet was re-suspended in 35 ml of binding buffer (20 mM sodium phosphate, 0.5 M NaCl, 20 mM imidazole, pH 7.4) supplemented with 29 U/ml Benzonase® (Merck) and the cells were disrupted by ultrasonication. Cell debris was removed by centrifugation and each supernatant was applied on a 1 ml His GraviTrap IMAC column (GE Healthcare). Contaminants were removed by washing with wash buffer (20 mM sodium phosphate, 0.5 M NaCl, 60 mM imidazole, pH 7.4) and the CAIX binding Z variants were subsequently eluted with elution buffer (20 mM sodium phosphate, 0.5 M NaCl, 500 mM imidazole, pH 7.4). Each Z variant was transferred to PBS (2.68 mM KCl, 0.47 mM $KH_2PO_4$, 137 mM NaCl, 8.1 mM $Na_2HPO_4$, pH 7.4.) by size exclusion chromatography. Protein concentrations were determined by measuring the absorbance at 280 nm, using a NANODROP ND-1000 spectrophotometer, and using the extinction coefficient of the respective protein. The purity of each CAIX binding Z variant was analyzed by SDS-PAGE stained with Coomassie Blue. The identity of each purified CAIX binding Z variant was confirmed using HPLC-MS analysis.

Immunofluorescence Staining for Flow Cytometry Analysis:

SK-RC-52 cells (renal clear cell carcinoma cell line; kindly provided by Active Biotech, Sweden) were cultured in RPMI-1640 (Lonza) with the addition of 10% FCS, 1% glutamine and 1% PEST (penicillin-streptomycin). On the day of assay, SK-RC-52 cells were trypsinated, counted and $0.1-0.2 \times 10^6$ cells added to 5 ml falcon tubes. The cells were pelleted by centrifugation at 1200 rpm and supernatant removed. The cells were stained with following maturated Z variants in monomer format; Z06919, Z06936, Z06942, Z06959, Z06961, Z06976, Z06984, Z06986, Z06999, Z07084, Z07089 and Z07091. For screening, 100 µl of 12 different binders diluted in PBS 2% FCS to 10 µg/ml was added and cells were incubated for two hours at 4° C. Alternatively, the binders were titrated for EC50 value calculations at four different concentrations: 2, 0.5, 0.05 and 0.003 µg/ml. Z variant Z08693, which corresponds to Z variant Z04196 identified in Example 1 but for the amino acid substitution A54S, was included in the assay for comparison. A Z variant binding to an unrelated target was used as negative control and PBS was used as background control. The cells were washed once by filling up the tube with PBS and pelleting the cells by centrifugation. The pelleted cells were resuspended in 100 µl of a goat anti-Z variant-specific Ig, 5 µg/ml and incubated for one hour at 4° C. A goat anti-CAIX specific antibody, MAB2188 (R&D systems), was included as a positive control at a concentration of 5 µg/ml. Cells were subsequently washed in PBS as described and resuspended in 100 µl of Alexa488-labeled anti-goat antibody (Invitrogen) at a concentration of 10 µg/ml. After 45 minutes of incubation at 4° C., cells were washed in PBS, resuspended in 300 µl of PBS and subjected to FACS analysis using a FACSCantoII. The MFI was recorded.

Immunofluorescence Staining for Microscopy:

SK-RC-52 cells were seeded onto multiwell slides (Histolab, eight wells/slide) and cultured in complete medium overnight in the incubator. The next day, the cells were fixed in 2% formaldehyde in PBS for 15 minutes at RT. The formaldehyde was removed by careful washing using approximately 2-3 ml PBS per slide. The cells were stained with maturated Z variants, with an unrelated binder (negative control) or with PBS 2% FCS (background control). 50 µl of the binders diluted to 0.5 µg/ml in PBS 2% FCS were added to selected wells on the multi well slides. The cells were incubated at RT for 2 hours and then carefully washed three times with PBS. The Z variants were detected by incubation with goat anti-Z variant Ig (5 µg/ml in PBS 2% FCS) for 1.5 hours. A CAIX specific antibody, MAB2188 (R&D systems) was included as a positive control at a concentration of 10 µg/ml. After 1 hours incubation with Alexa488-labeled anti-goat antibody (10 µg/ml in PBS 2% FCS), the slides were washed carefully in PBS, dried and mounted with anti-fading solution (Vectashield, Vector laboratories). The staining was analyzed with a Leica DM-LA UV microscope equipped with a digital camera. Representative pictures were taken of each individual binder.

Biacore Binding Analysis:

The interactions of four $His_6$-tagged CAIX-binding Z variants (Z06936, Z06942, Z06976 and Z07084) with human CAIX were analyzed in a Biacore 2000 instrument essentially as described in Example 2. The analytes, i.e. the Z variants, were each diluted in HBS-EP running buffer to final concentrations of 10, 30, 90, 270 and 810 nM and injected at a flow-rate of 30 µl/min for 5 minutes. After 5 minutes of dissociation, the surfaces were regenerated with two injections of 1 ml Glycine, pH 3. The results were analyzed using the BiaEvaluation software.

Results

Protein Expression and Purification:

Binder Z08693, corresponding to binder Z04196 from the primary selection but containing the amino acid substitution A54 S, and 12 matured CAIX binding Z variants: Z06919 (SEQ ID NO:232), Z06936 (SEQ ID NO:227), Z06942 (SEQ ID NO:228), Z06959 (SEQ ID NO:233), Z06961 (SEQ ID NO:234), Z06976 (SEQ ID NO:229), Z06984 (SEQ ID NO:236), Z06986 (SEQ ID NO:237), Z06999 (SEQ ID NO:238), Z07084 (SEQ ID NO:231), Z07089 (SEQ ID NO:239), and Z07091 (SEQ ID NO:230), with an N-terminal $His_6$ tag, expressed well in *E. coli*. The amount of IMAC-purified protein from approximately 1.5 g bacterial pellets, determined spectrophotometrically by measuring the absorbance at 280 nm, ranged from 2 mg to 22 mg for the different CAIX binding Z variants.

SDS-PAGE analysis of each final protein preparation showed that these predominantly contained respective CAIX binding Z variant. The correct molecular weight of each CAIX binding Z variant was confirmed by HPLC-MS.

Figure 4:
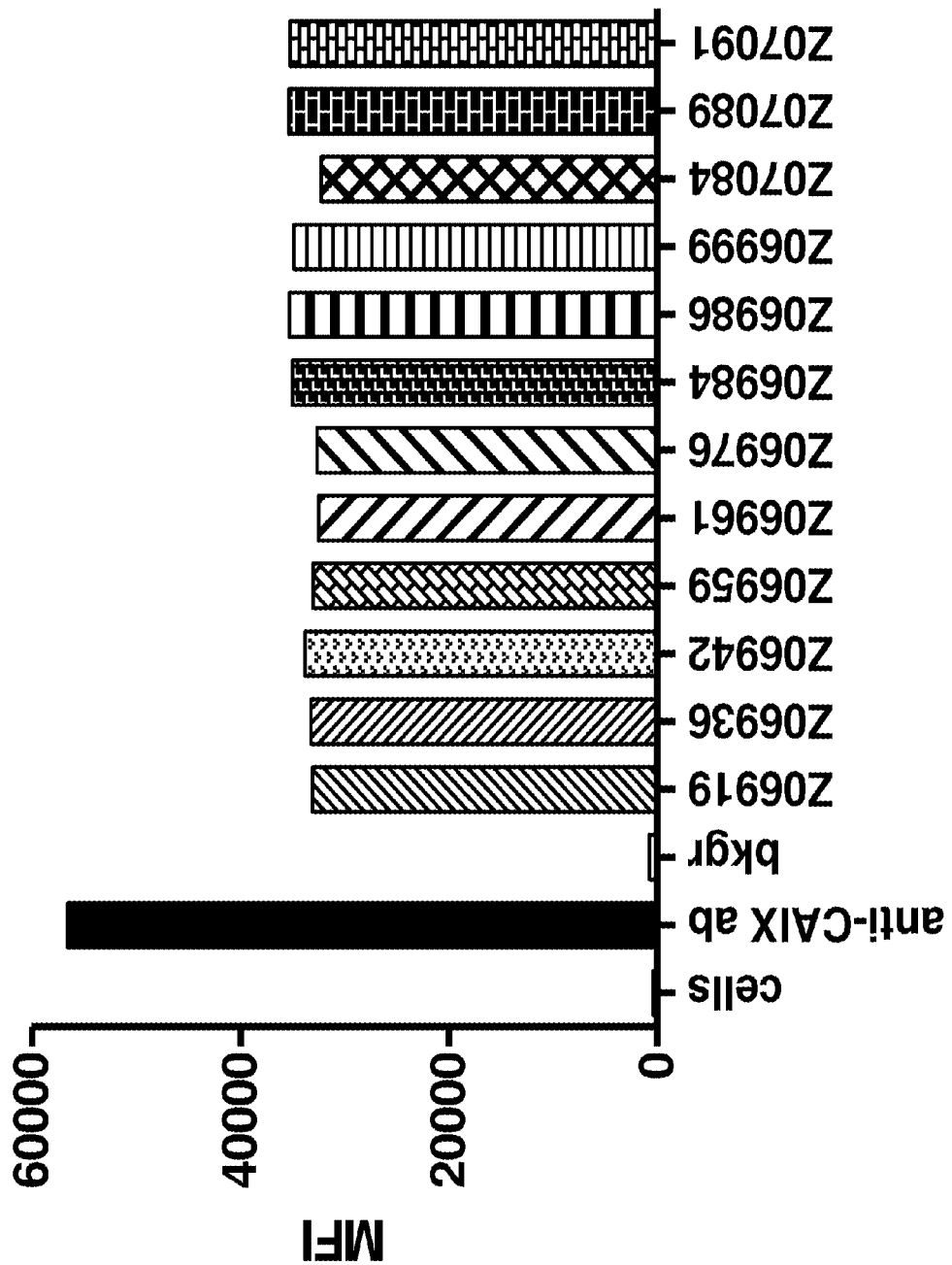
FIG. 4 shows the result of staining of CAIX on SK-RC-52 cells as described in Example 5. The 12 indicated Z variants from maturation and a CAIX specific antibody were tested for binding to SK-RC-52 cells. The flow cytometry analysis showed that all 12 Z variants bound to SK-RC-52 cells with a similar intensity. MFI: mean fluorescence intensity.

Immunofluorescence Staining for Flow Cytometry Analysis and Microscopy:

SK-RC-52 cells were stained with 12 different maturated binders Z06919, Z06936, Z06942, Z06959, Z06961, Z06976, Z06984, Z06986, Z06999, Z07084, Z07089 and Z07091. The CAIX specific antibody MAB2188 was included as positive control. The intensity of staining was analyzed with flow cytometry. The geometric mean fluorescence intensity (MFI) for the 12 different binders, respectively, is shown in FIG. 4. All the CAIX specific Z variants seemed to bind equally well to SK-RC-52 cells with approximately half the MFI value compared to the control antibody. However, the antibody has two binding sites and it is considerably larger (150 kDa), thus there are more sites available for binding of the fluorescently labeled second step antibody (anti-goat Ig Alexa488) compared to the relatively small Z variants (6 kDa). To separate the binding of the 12 Z variants from each other, a titration was performed. The EC50 values were calculated using Graph Pad Prism and a nonlinear regression formula. The EC50 values of the binders were between 10 and 20 nM except for Z07084 which had an EC50 of 37 nM (Table 4). The calculated EC50 value for Z08693 was around 1800 nM indicating that the maturation resulted in an increase in binding ability of approximately 100 times.

TABLE 4

EC50 values of one primary and 12 maturated CAIX specific Z variants.

| Z variant | EC50 (nM) |
| --- | --- |
| $His_6$-Z08693 | 1820 |
| $His_6$-Z06919 | 20 |
| $His_6$-Z06936 | 15 |
| $His_6$-Z06942 | 14 |
| $His_6$-Z06959 | 18 |
| $His_6$-Z06961 | 17 |
| $His_6$-Z06976 | 13 |
| $His_6$-Z06984 | 11 |
| $His_6$-Z06986 | 12 |
| $His_6$-Z06999 | 16 |
| $His_6$-Z07084 | 37 |
| $His_6$-Z07089 | 12 |
| $His_6$-Z07091 | 18 |

Figure 5:
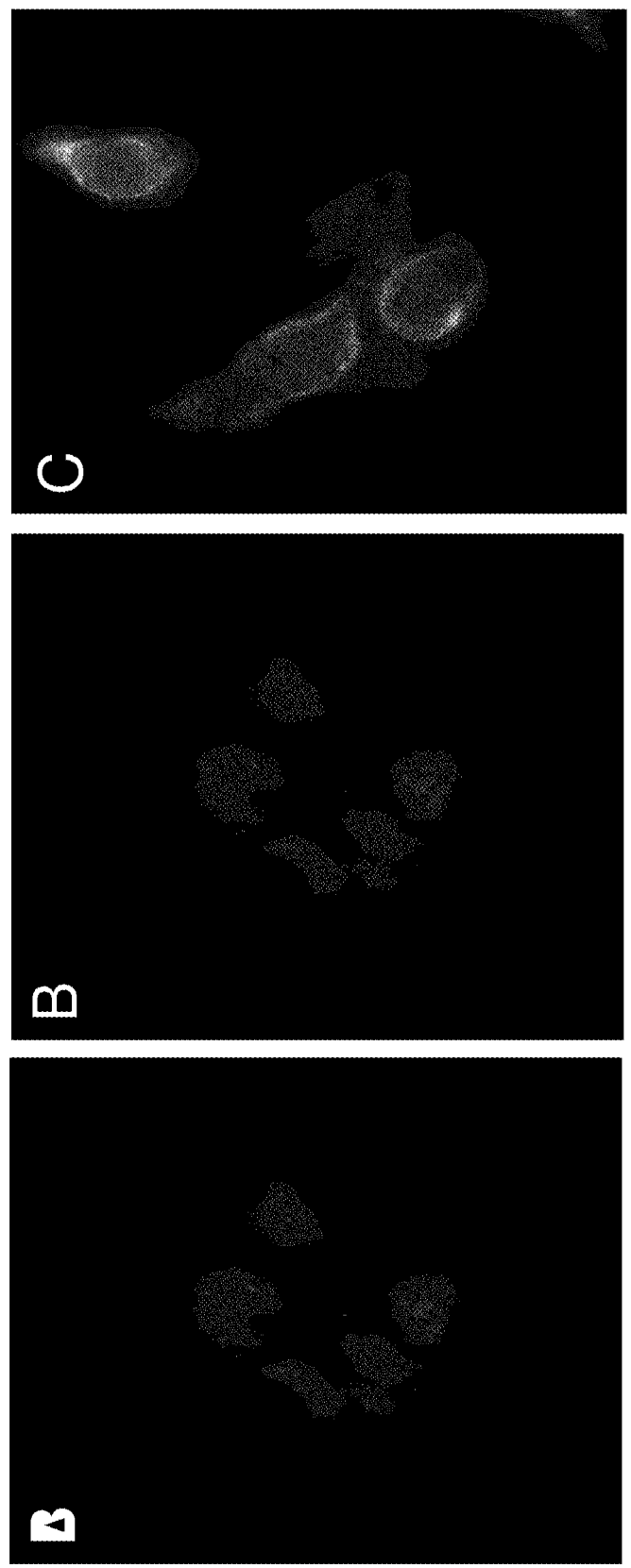
FIG. 5 shows the result of immunofluorescence staining of CAIX on SK-RC-52 cells as described in Example 5. The cells were stained with Z06936 (SEQ ID NO:227) (A), negative Z variant (B) and CAIX specific antibody (C). The resulting images show membrane specific staining on SK-RC-52 cells.

The specificity of the binding was investigated with fluorescence microscopy and all binders bound to the cell surface of SK-RC-52 cells in a similar pattern as the positive control. FIG. 5 shows membrane staining of Z06936 (SEQ ID NO:227), representative of all 12 binders. Thus, the binding was morphologically correct.

Biacore Binding Analysis:

The interactions of $His_6$-tagged CAIX-binding Z variants Z06936, Z06942, Z06976 and Z07084 with human CAIX were analyzed in a Biacore instrument by injecting various concentrations of the Z variants over a surface containing immobilized CAIX. A summary of the apparent kinetic parameters ($K_D$, $k_a$ ($k_{on}$) and $k_d$ ($k_{off}$)) for binding of the Z variants to CAIX using a 1:1 interaction model is given in Table 5 below.

TABLE 5

Relative kinetic parameters for binding of Z variants to CAIX.

| Analyte | $k_a$ (1/Ms) | $k_d$ (1/s) | $K_D$ (M) |
| --- | --- | --- | --- |
| $His_6$-Z06936 | $7.77 \times 10^4$ | $2.08 \times 10^{-3}$ | $2.7 \times 10^{-8}$ |
| $His_6$-Z06942 | $1.67 \times 10^5$ | $1.88 \times 10^{-3}$ | $1.1 \times 10^{-8}$ |
| $His_6$-Z06976 | $9.04 \times 10^4$ | $2.92 \times 10^{-3}$ | $3.2 \times 10^{-8}$ |
| $His_6$-Z07084 | $5.98 \times 10^5$ | $1.06 \times 10^{-2}$ | $1.8 \times 10^{-8}$ |

Example 6

Radiolabeling and Characterization of CAIX Binding Z Variants

This Example describes production, radiolabeling and characterization of four CAIX binding Z variants, Z09781 (SEQ ID NO:365), Z09782 (SEQ ID NO:366), Z09783 (SEQ ID NO:367) and Z09784 (SEQ ID NO:368), with CAIX binding motifs (BM) identical to the BM of Z06936 (SEQ ID NO:227), Z06942 (SEQ ID NO:228), Z06976 (SEQ ID NO:229) and Z07084 (SEQ ID NO:231) respectively, but with the Z polypeptide starting by "AE" instead of "VD", as well as being preceded by an N-terminal $(HE)_3$-tag instead of an $His_6$-tag.

Materials and Methods

Cloning and Production of Z Variants:

A subcloning strategy for construction of Z variant molecules with an N-terminal HEHEHE tag was applied using standard molecular biology techniques and as described in detail in WO 2009/077175 for Z variants binding another target. The Z gene fragments were subcloned into the expression vector pAY03086 resulting in the encoded sequence HEHEHE-[Z#####]-VD (SEQ ID NO. 390). Production in *E. coli* and purification by IMAC was performed essentially as described in Example 5. Additional purification was performed using reverse phase chromatography (RPC) and buffer was exchanged to PBS.

Labeling of Z Variants [$^{99m}$Tc(CO)$_3$]$^+$ and $^{125}$I:

Radiolabeling of (HE)$_3$-Z09781, (HE)$_3$-Z09782, (HE)$_3$-Z09783 and (HE)$_3$-Z09784 variants with [$^{99m}$Tc(CO)$_3$]$^+$ was performed as described earlier by Orlova et al (J. Nucl. Med., 47:512-519, 2006) and Tolmachev et al (Bioconjugate Chem, 21:2013-2022, 2010). Briefly, 400-500 µl (~3 GBq) of $^{99m}$TcO$_4^-$ eluate in 0.9% NaCl (pertechnetate eluted from an UltraTechneKow generator (Covidien)) was added to a lyophilized IsoLink kit (Covidien, Mansfield, Mass., USA). The mixture was incubated at 100° C. for 30 min. Thereafter, 40 µl of the mixture was transferred to vials containing 100 µg of respective Z variant in 40 µl of PBS. Incubation was performed at 50° C. for a total of 120 min.

The radiochemical labeling yields were analyzed by thin layer chromatography after 60 and 120 min incubation using ITLC 150-771 DARK GREEN strips (Tec-Control Chromatography strips, Biodex Medical Systems) and applying 1 µl of sample followed by elution with PBS.

Indirect radioiodination of (HE)$_3$-Z09781, (HE)$_3$-Z09782, (HE)$_3$-Z09783 and (HE)$_3$-Z09784 variants using N-succinimidyl-para-(trimethylstannyl)-benzoate (PerkinElmer, Waltham, Mass., USA) was performed as described previously by Orlova et al (J Nucl Med. 50:417, 2009).

The radiolabeled Z variants were purified using NAP-5 columns (GE Healthcare) pre-equilibrated with PBS, which was subsequently also used for elution. The purity of each preparation was evaluated using thin layer chromatography as described above.

LIGANDTRACER Binding Analysis:

The CAIX-expressing renal clear cell carcinoma cell line SK-RC-52 was seeded on a local area of a cell culture dish (Nunclon™, Size 100620, NUNC NS, Roskilde, Denmark). The binding of $^{99m}$Tc-labeled Z variants to living cells was monitored in real-time at 4° C. using a LIGANDTRACER Yellow (Ridgeview Instruments, Sweden) and established methods (Björkelund et al Appl Radiat Isot. 68:2372-6, 2010). In order to cover the concentration spans needed for proper affinity estimations, each radiolabeled Z variant was added at different concentrations: $^{99m}$Tc-(HE)$_3$-Z09781 (30, 90, and 150 nM), $^{99m}$Tc-(HE)$_3$-Z09782 (6 and 18 nM), $^{99m}$Tc-(HE)$_3$-Z09783 (2, 6, and 18 nM), and $^{99m}$Tc-(HE)$_3$-Z09784 (6, 12, and 24 nM). The kinetic parameters were determined using the LIGANDTRACER software.

Results

Radiolabeling:

All Z variants were efficiently labeled with $^{99m}$Tc and $^{125}$I, respectively. The coupling of [$^{99m}$Tc(CO)$_3$.(H$_2$O)$_3$] to (HE)$_3$-tagged Z variants was time dependent. Incubation of the Z variants with carbonyl-technetium complex at 50° C. provided 50-65% yield after 60 min and 70-80% yield after 120 min. After purification with disposable NAP-5 columns, the radiochemical purity of the technetium-labeled variants was more than 99.5%. The overall yield of $^{125}$I-PIB-(HE)$_3$-labeled Z variants was 14-28%. The radiochemical purity of the $^{125}$I-iodinated Z variants after purification using NAP-5 columns was more than 97%.

LIGANDTRACER Binding Analysis:

The kinetic measurements of $^{99m}$Tc-labeled Z variants to CAIX-expressing SK-RC-52 cells in vitro using LIGANDTRACER Yellow confirmed that their high affinity to CAIX was preserved after radiolabeling. Data analysis indicated that the binding of radiolabeled conjugates to living CAIX-expressing cells is mediated by two binding events for the $^{99m}$Tc-labeled (HE)$_3$-Z09781, (HE)$_3$-Z09783 and (HE)$_3$-Z09784 constructs. A summary of the apparent kinetic parameters ($K_D$, $k_a$ ($k_{on}$) and $k_d$ ($k_{off}$)) for binding of the Z variants to CAIX expressing cells is given in Table 6.

TABLE 6

Relative kinetic parameters for binding of Z variants to CAIX expressing cells.

| Z variant | $k_{a1}$ (1/Ms) | $k_{d1}$ (1/s) | $K_{D1}$ (M) |
|---|---|---|---|
| $^{99m}$Tc-(HE)$_3$-Z09781 | 7.4 × 10$^3$ | 1.0 × 10$^{-5}$ | 1.3 × 10$^{-9}$ |
| $^{99m}$Tc-(HE)$_3$-Z09782 | 3.3 × 10$^3$ | 1.9 × 10$^{-5}$ | 6.1 × 10$^{-9}$ |
| $^{99m}$Tc-(HE)$_3$-Z09783 | 5.9 × 10$^3$ | 2.7 × 10$^{-5}$ | 4.5 × 10$^{-9}$ |
| $^{99m}$Tc-(HE)$_3$-Z09784 | 1.2 × 10$^4$ | 1.1 × 10$^{-4}$ | 9.1 × 10$^{-9}$ |
| | $k_{a2}$ (1/MS) | $k_{d2}$ (1/s) | $K_{D2}$ (M) |
| $^{99m}$Tc-(HE)$_3$-Z09781 | 1.3 × 10$^4$ | 1.7 × 10$^{-3}$ | 1.3 × 10$^{-7}$ |
| $^{99m}$Tc-(HE)$_3$-Z09782 | n.a. | n.a | n.a |
| $^{99m}$Tc-(HE)$_3$-Z09783 | 3.8 × 10$^3$ | 2.3 × 10$^{-4}$ | 6.1 × 10$^{-8}$ |
| $^{99m}$Tc-(HE)$_3$-Z09784 | 3.4 × 10$^4$ | 2.5 × 10$^{-3}$ | 7.5 × 10$^{-8}$ |

Example 7

In Vitro Binding Specificity and Cellular Processing of Radiolabeled CAIX Binding Z Variants Binding specificity and cellular processing studies of $^{99m}$Tc-labeled (HE)$_3$-Z09781, (HE)$_3$-Z09782, (HE)$_3$-Z09783 and (HE)$_3$-Z09784 variants were performed using the renal clear cell carcinoma SK-RC-52 cell line.

Materials and Methods

The specificity of $^{99m}$Tc-labeled Z variants for the CAIX-receptor and their cellular processing was assessed as described by Wållberg and Orlova (Cancer Biother. Radiopharm., 23: 435-442, 2008). Briefly, for each radiolabeled Z variant, a separate set of triple dishes containing a monolayer of SK-RC-52 cells (~1×10$^6$ cells/dish) were pre-saturated with a 100-fold excess of the same unlabeled Z variant polypeptide or one of the other three Z variants included in the study. Incubation with unlabeled Z variants was performed for 15 min before addition of the radiolabeled conjugates: 13 nM $^{99m}$Tc-(HE)$_3$-Z09781, 61 nM $^{99m}$Tc-(HE)$_3$-Z09782, 45 nM $^{99m}$Tc-(HE)$_3$-Z09783, and 90 nM $^{99m}$Tc-(HE)$_3$-Z09784, respectively, followed by incubation for 1 h in a humidified incubator (5% CO$_2$, 37° C.). Thereafter, the medium was collected, the cells were washed with cold serum-free medium and trypsin-EDTA solution (0.25% trypsin, 0.02% EDTA in buffer, Biochrom AG, Berlin, Germany) was added. Detached cells were collected after 10 min. The radioactivity of cells and media was measured using an automated gamma counter with a 3-in NaI (TI) detector (1480 WIZARD, Wallac Oy, Turku, Finland) and the percentage of cell-bound radioactivity was calculated.

To evaluate the cellular processing, SK-RC-52 cells were incubated with the radiolabeled Z variants at 37° C. and 5% CO$_2$. At designated time points (1, 2, 4, 8 and 24 h), a set of three dishes was removed from the incubator, the media was collected and cells were washed with ice cold serum-free medium. Cells were then treated with 0.5 ml of 0.2 M glycine buffer, pH 2, containing 4 M urea, for 5 min on ice. The acidic solution was collected and cells were washed with 0.5 ml glycine buffer. The acidic fractions were pooled.

The cells were then incubated with 0.5 ml 1 M NaOH at 37° C. for at least 20 min. The cell debris was collected and the dishes were additionally washed with 0.5 ml of NaOH solution. The alkaline fractions were pooled. The radioactivity in the acidic solution was considered as membrane bound, and in the alkaline fractions as internalized.

Results

A significant (p<0.005) decrease in binding of $^{99m}$Tc-labled Z variants to CAIX-expressing SK-RC-52 cells after saturation of the receptors using unlabeled Z variants was observed, suggesting that binding of the radiolabeled variants was receptor mediated (FIG. 6A-6D). Moreover, it was possible to block the binding of each variant using each of the three other variants included in the study, indicating that they all bind to the same site on CAIX (FIG. 6A-6D).

The cellular processing study showed that internalization of all radio-conjugates was relatively low and increased slightly throughout the assay. The amount of internalized radioactivity by SK-RC-52 cells after 24 h incubation is shown in Table 7.

TABLE 7

Cellular processing of Z variants by SK-RC-52 cells.

| Z variant | Fraction internalized radioactivity after 24 h |
|---|---|
| $^{99m}$Tc-(HE)$_3$-Z09781 | 17% |
| $^{99m}$Tc-(HE)$_3$-Z09782 | 25% |
| $^{99m}$Tc-(HE)$_3$-Z09783 | 25% |
| $^{99m}$Tc-(HE)$_3$-Z09784 | 43% |

Example 8

In Vivo Evaluation of Radiolabeled CAIX Binding Z Variants

Z09781 (SEQ ID NO:365), was selected for in vivo biodistribution and imaging studies.

Materials and Methods

Animals and Cells:

Biodistribution studies were performed in female NMRI nu/nu mice. Two weeks before the study, 10×10$^6$ cells from renal clear cell carcinoma (SK-RC-52 cell line) were implanted in the right hind legs of NMRI nu/nu mice. Average tumor weight was 0.30±0.14 g at the time of experiment, and the average animal weight was 17.1±1.3 g.

Biodistribution Study Using $^{99m}$Tc-(HE)$_3$-Z09781:

In order to determine the optimal injection dose, three groups of mice (n=4) were injected intravenously (tail vein) with three different doses (0.3 µg, 1 µg, and 5 µg, respectively) of $^{99m}$Tc-(HE)$_3$-Z09781 in 100 µl PBS and sacrificed at 4 h post injection. Another three groups of mice (n=4) were injected with 1 µg to follow the clearance profile of $^{99m}$Tc-(HE)$_3$-Z09781 at 1, 4 and 8 h post injection. To check the specificity of xenograft targeting of $^{99m}$Tc-(HE)$_3$-Z09781, a group of mice (n=4) was subcutaneously pre-injected with 500 µg of unlabeled (His)$_6$-Z06936 (parent Z variant to (HE)$_3$-Z09781) and sacrificed at 4 h post injection.

Blood, lung, liver, spleen, stomach, colon, duodenum, kidney, salivary glands, muscle, bone, intestines, tumor, and the remaining carcass were collected. Organs and tissue samples were weighed, and their radioactivity was measured. The tissue uptake values were calculated as percent of injected dose per gram tissue (% ID/g) except for the intestine and the carcass, which was calculated as % ID per whole sample.

Biodistribution Study Using $^{125}$I-(HE)$_3$-Z09781:

Two groups of mice (n=3) were injected intravenously with 1 µg of $^{125}$I-(HE)$_3$-Z09781 in 100 µl PBS. The mice were sacrificed at 6 and 8 h post injection.

Organs were collected and analyzed as described above.

In Vivo Imaging:

Imaging was performed to obtain a visual confirmation of the biodistribution data. Two SK-RC-52 xenograft bearing mice were each injected with 10 MBq (3 µg) of $^{99m}$Tc-Z09781. Mice were sacrificed by cervical dislocation at 4 h post injection. The imaging experiment was performed using an Infinia γ-camera (GE Healthcare) equipped with a Low-Energy High Resolution (LEHR) collimator.

Results

Figure 7:
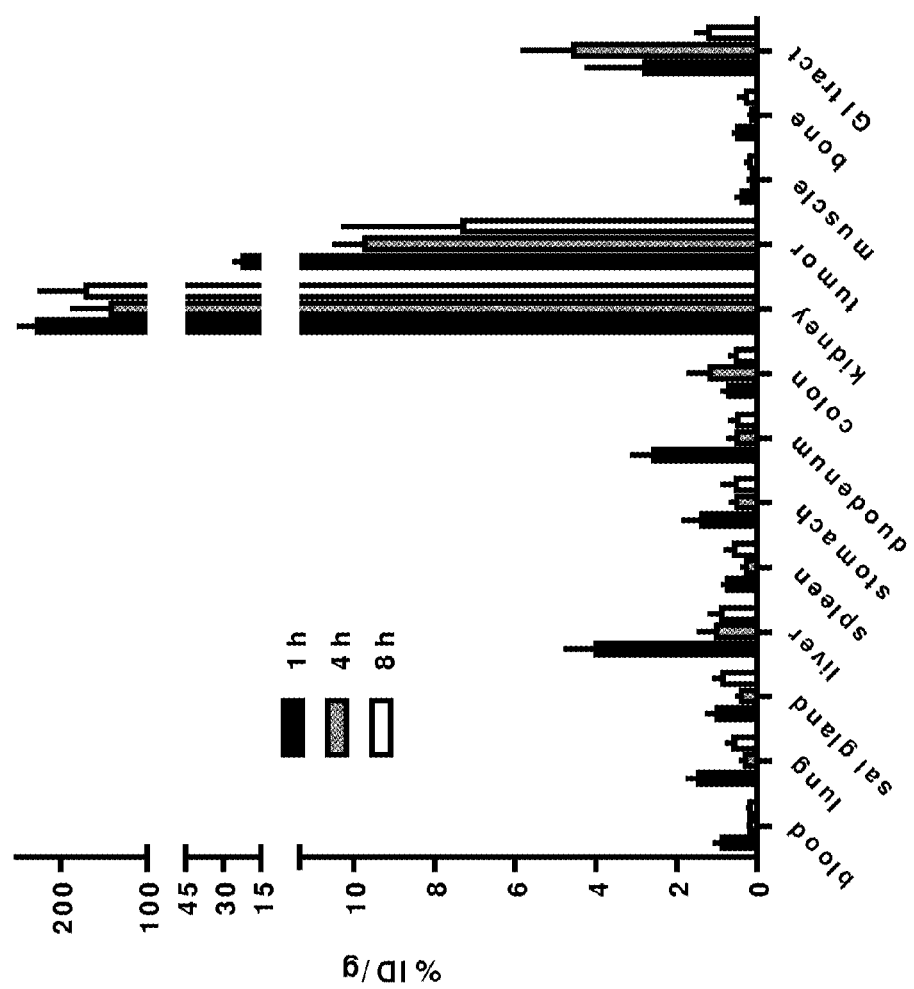
FIG. 7 shows the result of the biodistribution study described in Example 8, at 1, 4 and 8 h after injection of $^{99m}Tc$-$(HE)_3$-Z09781 in NMRI nu/nu mice bearing SK-RC-52 xenografts. The concentration of radioactivity is expressed as % ID/g (except for GI tract), and the data presented is the average (n=4 per time point)±standard deviation. Data for the gastrointestinal tract (GI) with content and carcass are presented as % of injected radioactivity per whole sample.

Biodistribution Studies of Radiolabeled Z Variant:

There was no significant difference (p>0.05) in the biodistribution after injection of the three different doses (0.3, 1 or 5 µg) of $^{99m}$Tc-(HE)$_3$-Z09781 into female NMRI nu/nu mice bearing SK-RC-52 xenografts. The injected dose of 1 µg provided slightly higher tumor-to-spleen ratio and was therefore selected for further in vivo studies. The biodistribution of $^{99m}$Tc-(HE)$_3$-Z09781 (1 µg) in female NMRI nu/nu mice bearing SK-RC-52 xenografts at 1, 4 and 8 h post injection is shown in FIG. 7. The clearance of the radioconjugates from body was via kidneys with subsequent re-absorption. The highest level of renal radioactivity was at 1 h post injection. $^{99m}$Tc-(HE)$_3$-Z$_{09781}$ showed a rapid blood clearance already at 1 h post injection. The blood-associated radioactivity decreased about 4 times between 1 and 4 h but did not decrease further at 8 h after injection.

The tumor uptake of radioactivity was the highest at 1 h (22.3±3.2% ID/g), which decreased about two times (9.7±0.7% ID/g) at 4 h but then remained constant up to 8 h after injection. Overall, the tumor-to-blood and tumor-to-organ (except for tumor-to-colon) ratios of $^{99m}$Tc-(HE)$_3$-Z09781 were the highest at 4 h, and had decreased slightly at 8 h after injection.

The in vivo specificity test showed that the tumor uptake 4 h after injection of $^{99m}$Tc-(HE)$_3$-Z09781 (9.7±0.7% ID/g) in non-saturated CAIX expressing xenografts was significantly (p<0.05) higher than the uptake in xenografts pre-saturated with unlabeled (His)$_6$-Z06936 variant (0.4±0.1% ID/g).

Figure 8:
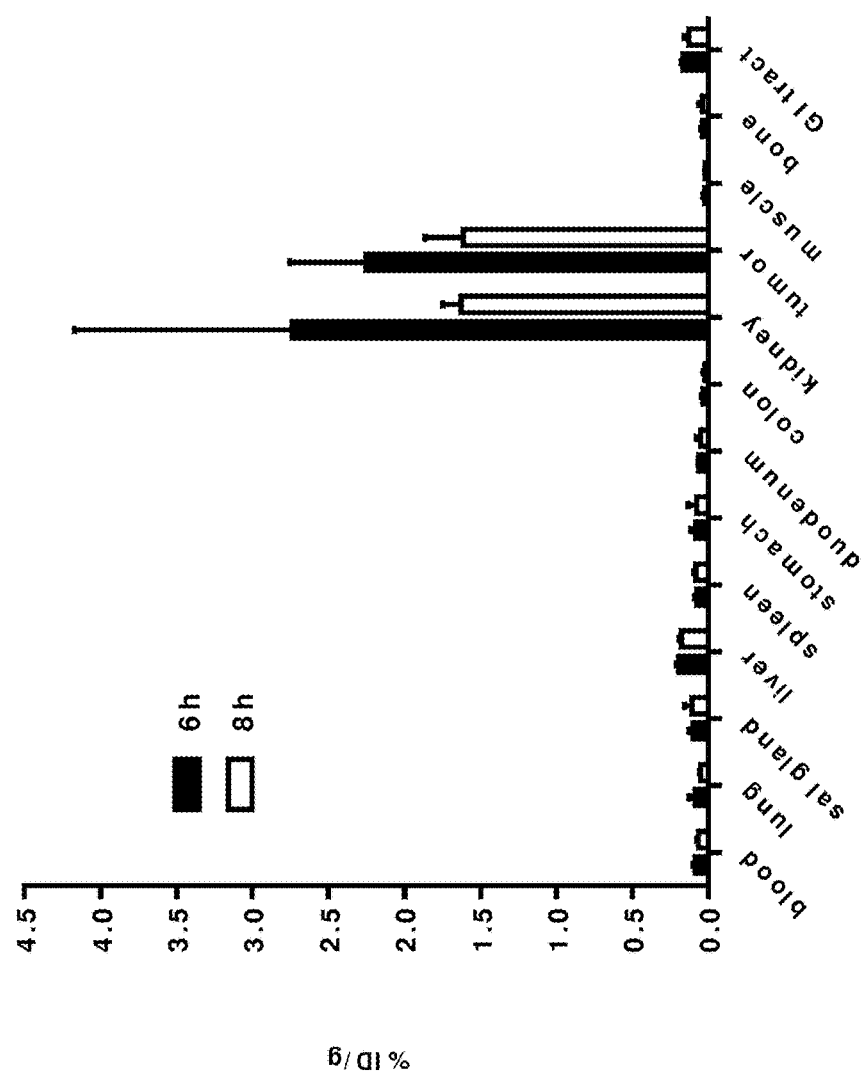
FIG. 8 shows the result of the biodistribution study described in Example 8, at 6 and 8 h after injection of $^{125}I$-$(HE)_3$-Z09781 in NMRI nu/nu mice bearing SK-RC-52 xenografts. Data is presented as in FIG. 7, but n=3 per time point.

The biodistribution of $^{125}$I-(HE)$_3$-Z09781 in female NMRI nu/nu mice bearing SK-RC-52 xenografts at 6 and 8 h post injection is shown in FIG. 8. There was no significant difference between the biodistribution and the tumor uptake as well as the tumor-to-blood and the tumor-to-organ ratio of $^{125}$I-(HE)$_3$-Z09781 at 6 and 8 h post injection. Tumor-to-lung, -kidney, -muscle, and -bone ratios of $^{125}$I-(HE)$_3$-Z09781 were higher than for $^{99m}$Tc-(HE)$_3$-Z09781. However, the total tumor uptake was appreciably higher for $^{99m}$Tc-(HE)$_3$-Z09781.

Figure 9:
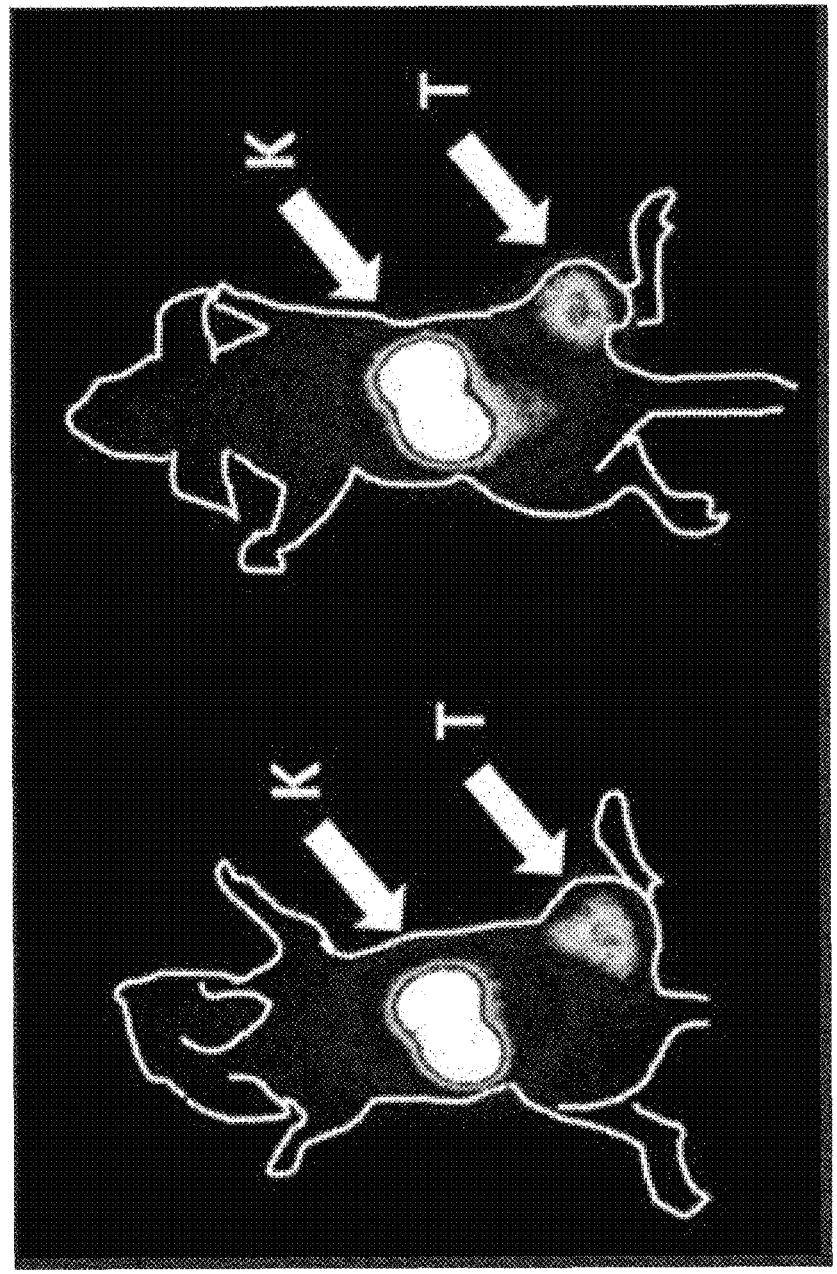
FIG. 9 shows images from gamma-camera imaging of CAIX-expressing xenografts 4 h after injection of $^{99m}Tc$-$(HE)_3$-Z09781, as described in Example 8. Arrows indicate tumors (T) and kidneys (K).

In Vivo Imaging:

The gamma camera images (4 h post injection) confirmed the feasibility of in vivo imaging of CAIX-expressing xenografts using $^{99m}$Tc-(HE)$_3$-Z09781 (FIG. 9). The collected images clearly visualized the tumor and were in good agreement with the biodistribution data. The kidney was the only organ with a prominent radioactivity uptake.

Itemized Listing of Embodiments

1. CAIX binding polypeptide, comprising a CAIX binding motif BM, which motif consists of an amino acid sequence selected from:

i)
(SEQ ID NO. 369)
$EX_2X_3X_4AX_6X_7EIX_{10}$ $X_{11}LPNLX_{16}X_{17}X_{18}QX_{20}$ $X_{21}AFIX_{25}X_{26}LWD$ wherein, independently from each other,
$X_2$ is selected from D, H, N, Q and W;
$X_3$ is selected from E, F, I, K, L, Q, R, S, T, V, W and Y;
$X_4$ is selected from A, F, N, W and Y;
$X_6$ is selected from A, G, S and W;
$X_7$ is selected from A, E, G, I, Q, T, V and W;
$X_{10}$ is selected from A, D, E, G, H, I, N, Q, R, S, T and V;
$X_{11}$ is selected from D, E, K, R and S;
$X_{16}$ is selected from N and T;
$X_{17}$ is selected from A, D, E, G, H, I, Q, S, T, V and W;
$X_{18}$ is selected from A, D, E, F, G, H, I, L, N, Q, R, S, T, V, W and Y;
$X_{20}$ is selected from K, Q and R;
$X_{21}$ is selected from D, H, N and Q;
$X_{25}$ is selected from F and Y;
$X_{26}$ is selected from K and S; and ii) an amino acid sequence which has at least 89% identity to the sequence defined in i).

2. CAIX binding polypeptide according to item 1, wherein sequence i) is defined by:

(SEQ ID NO. 370)
$EX_2X_3X_4AX_6X_7EIX_{10}$ $X_{11}LPNLX_{16}X_{17}X_{18}QX_{20}$ $X_{21}AFIYX_{26}LWD$ wherein, independently from each other,
$X_2$ is selected from D, H, N, Q and W;
$X_3$ is selected from F, I, L, Q, R, S, T, V, W and Y;
$X_4$ is selected from A, F, N, W and Y;
$X_6$ is selected from A, G, S and W;
$X_7$ is selected from A, E, G, I, V and W;
$X_{10}$ is selected from A, D, E, G, H, N, Q, R, S, T and V;
$X_{11}$ is selected from D, E, R and S;
$X_{16}$ is selected from N and T;
$X_{17}$ is selected from A, D, E, G, I, Q, S, T, V and W;
$X_{18}$ is selected from A, D, E, F, G, H, I, L, N, Q, R, S, T, V, W and Y;
$X_{20}$ is selected from Q and R;
$X_{21}$ is selected from D, H, N and Q; and
$X_{26}$ is selected from K and S.

3. CAIX binding polypeptide according to item 1 or 2, wherein $X_2$ in sequence i) is selected from H, N, Q and W.

4. CAIX binding polypeptide according to item 1 or 2, wherein $X_2$ in sequence i) is selected from D, H, N and Q.

5. CAIX binding polypeptide according to item 3, wherein $X_2$ in sequence i) is selected from H, N and W.

6. CAIX binding polypeptide according to item 5, wherein $X_2$ in sequence i) is selected from H and W.

7. CAIX binding polypeptide according to item 5, wherein $X_2$ in sequence i) is selected from N and W.

8. CAIX binding polypeptide according to item 4 or 5, wherein $X_2$ in sequence i) is selected from H and N.

9. CAIX binding polypeptide according to item 6 or 8, wherein $X_2$ in sequence i) is H.

10. CAIX binding polypeptide according to item 7 or 8, wherein $X_2$ in sequence i) is N.

11. CAIX binding polypeptide according to item 6 or 7, wherein $X_2$ in sequence i) is W.

12. CAIX binding polypeptide according to any preceding item, wherein $X_3$ in sequence i) is selected from I, L, Q, R, S and W.

13. CAIX binding polypeptide according to item 12, wherein $X_3$ in sequence i) is selected from I, L, Q, R and W.

14. CAIX binding polypeptide according to item 13, wherein $X_3$ in sequence i) is selected from I, L, Q and W.

15. CAIX binding polypeptide according to item 13, wherein $X_3$ in sequence i) is selected from I, L, R and W.

16. CAIX binding polypeptide according to item 14 or 15, wherein $X_3$ in sequence i) is selected from I, L and W.

17. CAIX binding polypeptide according to item 16, wherein $X_3$ in sequence i) is selected from I and L.

18. CAIX binding polypeptide according to item 17, wherein $X_3$ in sequence i) is I.

19. CAIX binding polypeptide according to item 17, wherein $X_3$ in sequence i) is L.

20. CAIX binding polypeptide according to any preceding item, wherein $X_4$ in sequence i) is selected from A, F, W and Y.

21. CAIX binding polypeptide according to item 20, wherein $X_4$ in sequence i) is selected from A, F and W.

22. CAIX binding polypeptide according to item 21, wherein $X_4$ in sequence i) is selected from F and W.

23. CAIX binding polypeptide according to item 22, wherein $X_4$ in sequence i) is F.

24. CAIX binding polypeptide according item 22, wherein $X_4$ in sequence i) is W.

25. CAIX binding polypeptide according to any preceding item, wherein $X_6$ in sequence i) is selected from A, G and S.

26. CAIX binding polypeptide according to item 25, wherein $X_6$ in sequence i) is selected from A and G.

27. CAIX binding polypeptide according to item 25, wherein $X_6$ in sequence i) is selected from G and S.

28. CAIX binding polypeptide according to item 26 or 27, wherein $X_6$ in sequence i) is G.

29. CAIX binding polypeptide according to any preceding item, wherein $X_7$ in sequence i) is selected from G, I, V and W.

30. CAIX binding polypeptide according to item 29, wherein $X_7$ in sequence i) is selected from V and W.

31. CAIX binding polypeptide according to item 29, wherein $X_7$ in sequence i) is selected from I and W.

32. CAIX binding polypeptide according to item 30 or 31, wherein $X_7$ in sequence i) W.

33. CAIX binding polypeptide according to any preceding item, wherein $X_{10}$ in sequence i) is selected from A, D, E, G, H, N, Q, R, S and T.

34. CAIX binding polypeptide according to item 33, wherein $X_{10}$ in sequence i) is selected from A, D, E, G, N, Q, S and T.

35. CAIX binding polypeptide according to item 34, wherein $X_{10}$ in sequence i) is selected from A, D, E, G, N, S and T.

36. CAIX binding polypeptide according to item 34, wherein $X_{10}$ in sequence i) is selected from A, D, E, G, Q, S and T.

37. CAIX binding polypeptide according to item 36, wherein $X_{10}$ in sequence i) is selected from A, D, E, Q, S and T.

38. CAIX binding polypeptide according to item 35 or 36, wherein $X_{10}$ in sequence i) is selected from A, D, E, G, S and T.

39. CAIX binding polypeptide according to item 37 or 38, wherein $X_{10}$ in sequence i) is selected from A, D, E, S and T.

40. CAIX binding polypeptide according to item 39, wherein $X_{10}$ in sequence i) is selected from D, E, S and T.

41. CAIX binding polypeptide according to item 39, wherein $X_{10}$ in sequence i) is selected from A, D, S and T.

42. CAIX binding polypeptide according to item 40 or 41, wherein $X_{10}$ in sequence i) is selected from D, S and T.

43. CAIX binding polypeptide according to item 41, wherein $X_{10}$ in sequence i) is selected from A, D and S.

44. CAIX binding polypeptide according to item 42, wherein $X_{10}$ in sequence i) is selected from D and T.

45. CAIX binding polypeptide according to item 42 or 43, wherein $X_{10}$ in sequence i) is selected from D and S.

46. CAIX binding polypeptide according to item 44 or 45, wherein $X_{10}$ in sequence i) is D.

47. CAIX binding polypeptide according to any preceding item, wherein $X_{11}$ in sequence i) is selected from D, E and S.

48. CAIX binding polypeptide according to item 47, wherein $X_{11}$ in sequence i) is selected from D and E.

49. CAIX binding polypeptide according to item 48, wherein $X_{11}$ in sequence i) is D.

50. CAIX binding polypeptide according to any preceding item, wherein $X_{16}$ in sequence i) is N.

51. CAIX binding polypeptide according to any one of items 1-49, wherein $X_{16}$ in sequence i) is T.

52. CAIX binding polypeptide according to any preceding item, wherein $X_{17}$ in sequence i) is selected from A, D, E, I, Q, T and V.

53. CAIX binding polypeptide according to item 52, wherein $X_{17}$ in sequence i) is selected from A, D, E, I, Q and V.

54. CAIX binding polypeptide according to item 52, wherein $X_{17}$ in sequence i) is selected from D, E, I, Q, T and V.

55. CAIX binding polypeptide according to item 53 or 54, wherein $X_{17}$ in sequence i) is selected from D, E, I, Q and V.

56. CAIX binding polypeptide according to item 55, wherein $X_{17}$ in sequence i) is selected from D, E, I and Q.

57. CAIX binding polypeptide according to item 56, wherein $X_{17}$ in sequence i) is selected from D, E and Q.

58. CAIX binding polypeptide according to item 56, wherein $X_{17}$ in sequence i) is selected from D, E and I.

59. CAIX binding polypeptide according to item 57 or 58, wherein $X_{17}$ in sequence i) is selected from D and E.

60. CAIX binding polypeptide according to item 59, wherein $X_{17}$ in sequence i) is E.

61. CAIX binding polypeptide according to item 59, wherein $X_{17}$ in sequence i) is D.

62. CAIX binding polypeptide according to any preceding item, wherein $X_{18}$ in sequence i) is selected from A, D, E, F, G, H, I, N, Q, R, S, T and Y.

63. CAIX binding polypeptide according to item 62, wherein $X_{18}$ in sequence i) is selected from A, D, E, F, G, H, N, Q, R, S and Y.

64. CAIX binding polypeptide according to item 63, wherein $X_{18}$ in sequence i) is selected from A, D, F, H, N, Q, R, S and Y.

65. CAIX binding polypeptide according to item 64, wherein $X_{18}$ in sequence i) is selected from D, F, H, Q, R, S and Y.

66. CAIX binding polypeptide according to item 65, wherein $X_{18}$ in sequence i) is selected from D, H, Q, R and Y.

67. CAIX binding polypeptide according to item 66, wherein $X_{18}$ in sequence i) is selected from D, H, Q and Y.

68. CAIX binding polypeptide according to item 67, wherein $X_{18}$ in sequence i) is selected from D, H and Q.

69. CAIX binding polypeptide according to item 67, wherein $X_{18}$ in sequence i) is selected from D, Q and Y.

70. CAIX binding polypeptide according to item 68 or 69, wherein $X_{18}$ in sequence i) is selected from D and Q.

71. CAIX binding polypeptide according to item 69, wherein $X_{18}$ in sequence i) is selected from Q and Y.

72. CAIX binding polypeptide according to item 68, wherein $X_{18}$ in sequence i) is selected from H and Q.

73. CAIX binding polypeptide according to any one of items 70-72, wherein $X_{18}$ in sequence i) is Q.

74. CAIX binding polypeptide according to item 62, wherein $X_{18}$ in sequence i) is selected from A, D, E, F, H, Q, R, S and Y.

75. CAIX binding polypeptide according to item 74, wherein $X_{18}$ in sequence i) is selected from D, E, F, H, Q, R, S and Y.

76. CAIX binding polypeptide according to item 75, wherein $X_{18}$ in sequence i) is selected from D, E, F, H, Q, S and Y.

77. CAIX binding polypeptide according to item 76, wherein $X_{18}$ in sequence i) is selected from D, E, F, Q, S and Y.

78. CAIX binding polypeptide according to item 77, wherein $X_{18}$ in sequence i) is selected from D, E, Q, S and Y.

79. CAIX binding polypeptide according to item 78, wherein $X_{18}$ in sequence i) is selected from D, E, S and Y.

80. CAIX binding polypeptide according to item 79, wherein $X_{18}$ in sequence i) is selected from D, E and Y.

81. CAIX binding polypeptide according to any preceding item, wherein $X_{20}$ in sequence i) is R.

82. CAIX binding polypeptide according to any preceding item, wherein $X_{21}$ in sequence i) is selected from D, H and N.

83. CAIX binding polypeptide according to item 82, wherein $X_{21}$ in sequence i) is selected from D and N.

84. CAIX binding polypeptide according to item 82, wherein $X_{21}$ in sequence i) is selected from H and N.

85. CAIX binding polypeptide according to item 83 or 84, wherein $X_{21}$ in sequence i) is N.

86. CAIX binding polypeptide according to any preceding item, wherein $X_{25}$ in sequence i) is Y.

87. CAIX binding polypeptide according to any preceding item, wherein $X_{26}$ in sequence i) is K.

88. CAIX binding polypeptide according to any preceding item, wherein $X_{26}$ in sequence i) is S.

89. CAIX binding polypeptide according to any preceding item, wherein sequence i) fulfills at least seven of the twelve conditions I-XII:
I. $X_2$ is N;
II. $X_3$ is selected from I and L;
III. $X_4$ is F;
IV. $X_6$ is G;
V. $X_7$ is W;
VI. $X_{10}$ is selected from D and S;
VII. $X_{11}$ is D;
VIII. $X_{16}$ is T;
IX. $X_{17}$ is selected from E and D;
X. $X_{18}$ is selected from D, Y, E and S;
XI. $X_{21}$ is N; and
XII. $X_{26}$ is K.

90. CAIX binding polypeptide according to item 89, wherein sequence i) fulfills at least eight of the twelve conditions I-XII.

91. CAIX binding polypeptide according to item 90, wherein sequence i) fulfills at least nine of the twelve conditions I-XII.

92. CAIX binding polypeptide according to item 91, wherein sequence i) fulfills at least ten of the twelve conditions I-XII.

93. CAIX binding polypeptide according to item 92, wherein sequence i) fulfills at least eleven of the twelve conditions I-XII.

94. CAIX binding polypeptide according to item 93, wherein sequence i) fulfills all of the twelve conditions I-XII.

95. CAIX binding polypeptide according to any preceding item, wherein sequence i) is selected from SEQ ID NO:1-113 and SEQ ID NO:340-344.

96. CAIX binding polypeptide according to item 95, wherein sequence i) is selected from SEQ ID NO:1-113.

97. CAIX binding polypeptide according to item 96, wherein sequence i) is selected from SEQ ID NO:1-4 and SEQ ID NO:6-41.

98. CAIX binding polypeptide according to item 97, wherein sequence i) is selected from SEQ ID NO:1-4, SEQ ID NO:6 and SEQ ID NO:8-37.

99. CAIX binding polypeptide according to item 96, wherein sequence i) is SEQ ID NO:1-14.

100. CAIX binding polypeptide according to item 99, wherein sequence i) is SEQ ID NO:1-8 and SEQ ID NO:10-13.

101. CAIX binding polypeptide according to item 100, wherein sequence i) is SEQ ID NO:1-5.

102. CAIX binding polypeptide according to item 98 or 101, wherein sequence i) is SEQ ID NO:1-4.

103. CAIX binding polypeptide according to item 102, wherein sequence i) is SEQ ID NO:1-3.

104. CAIX binding polypeptide according to any preceding item, wherein said CAIX binding motif forms part of a three-helix bundle protein domain.

105. CAIX binding polypeptide according to item 104, wherein said CAIX binding motif essentially forms part of two helices with an interconnecting loop, within said three-helix bundle protein domain.

106. CAIX binding polypeptide according to item 105, wherein said three-helix bundle protein domain is selected from bacterial receptor domains.

107. CAIX binding polypeptide according to item 106, wherein said three-helix bundle protein domain is selected from domains of protein A from *Staphylococcus aureus* or derivatives thereof.

108. CAIX binding polypeptide according to any preceding item, which comprises an amino acid sequence selected from:

iii)
(SEQ ID NO. 371)
K-[BM]-DPSQS X$_a$X$_b$LLX$_c$ EAKKL NDX$_d$Q;

wherein
[BM] is an CAIX binding motif as defined in any one of items 1-103;
X$_a$ is selected from A and S;
X$_b$ is selected from N and E;
X$_c$ is selected from A, S and C;
X$_d$ is selected from A and S; and iv) an amino acid sequence which has at least 81% identity to a sequence defined by iii).

109. CAIX binding polypeptide according to item 108, wherein X$_a$ in sequence iii) is A.

110. CAIX binding polypeptide according to item 108, wherein X$_a$ in sequence iii) is S.

111. CAIX binding polypeptide according to any one of items 108-110, wherein X$_b$ in sequence iii) is N.

112. CAIX binding polypeptide according to any one of items 108-110, wherein X$_b$ in sequence iii) is E.

113. CAIX binding polypeptide according to any one of items 108-112, wherein X$_c$ in sequence iii) is A.

114. CAIX binding polypeptide according to any one of items 108-112, wherein X$_c$ in sequence iii) is S.

115. CAIX binding polypeptide according to any one of items 108-112, wherein X$_c$ in sequence iii) is C.

116. CAIX binding polypeptide according to any one of items 108-115, wherein X$_d$ in sequence iii) is A.

117. CAIX binding polypeptide according to any one of items 108-115, wherein X$_d$ in sequence iii) is S.

118. CAIX binding polypeptide according to item 108, wherein, in sequence iii), X$_a$ is A; X$_b$ is N; X$_c$ is A and X$_d$ is A.

119. CAIX binding polypeptide according to item 108, wherein, in sequence iii), X$_a$ is A; X$_b$ is N; X$_c$ is C and X$_d$ is A.

120. CAIX binding polypeptide according to item 108, wherein, in sequence iii), X$_a$ is S; X$_b$ is E; X$_c$ is S and X$_d$ is S.

121. CAIX binding polypeptide according to item 108, wherein, in sequence iii), X$_a$ is S; X$_b$ is E; X$_c$ is C and X$_d$ is S.

122. CAIX binding polypeptide according to any one of items 108-121, wherein sequence iii) is selected from any one of SEQ ID NO:114-226 and SEQ ID NO:345-349.

123. CAIX binding polypeptide according to item 122, wherein sequence iii) is selected from any one of SEQ ID NO:114-226.

124. CAIX binding polypeptide according to item 123, wherein sequence iii) is selected from any one of SEQ ID NO:114-117 and SEQ ID NO:119-154.

125. CAIX binding polypeptide according to item 124, wherein sequence iii) is selected from any one of SEQ ID NO:114-117, SEQ ID NO:119, SEQ ID NO:121-150.

126. CAIX binding polypeptide according to item 123, wherein sequence iii) is selected from any one of SEQ ID NO:114-127.

127. CAIX binding polypeptide according to item 126, wherein sequence iii) is selected from any one of SEQ ID NO:114-121, and SEQ ID NO:123-126.

128. CAIX binding polypeptide according to item 127, wherein sequence iii) is SEQ ID NO:114-118.

129. CAIX binding polypeptide according to item 125 or 128, wherein sequence iii) is SEQ ID NO:114-117.

130. CAIX binding polypeptide according to item 129, wherein sequence iii) is SEQ ID NO:114-116.

131. CAIX binding polypeptide according to any one of items 1-108, which comprises an amino acid sequence selected from:

v)
(SEQ ID NO. 372)
YAK-[BM]-DPSQS SELLX$_c$ EAKKL NDSQA P;

wherein [BM] is an CAIX binding motif as defined in any one of items 1-103 and X$_c$ is selected from A, S and C; and vi) an amino acid sequence which has at least 83% identity to a sequence defined by v).

132. CAIX binding polypeptide according to any one of items 1-108, which comprises an amino acid sequence selected from:

```
vii)
                                       (SEQ ID NO. 373)
FNK-[BM]-DPSQS ANLLX_c EAKKL NDAQA P;
``` wherein [BM] is an CAIX binding motif as defined in any one of items 1-103 and $X_c$ is selected from A and C; and
viii) an amino acid sequence which has at least 83% identity to a sequence defined by vii).

133. CAIX binding polypeptide according to item 108, which comprises an amino acid sequence selected from:

```
                                       (SEQ ID NO. 374)
ADNNFNK-[BM]-DPSQSANLLSEAKKLNESQAPK;

(SEQ ID NO. 375)
ADNKFNK-[BM]-DPSQSANLLAEAKKLNDAQAPK;

(SEQ ID NO. 376)
ADNKFNK-[BM]-DPSVSKEILAEAKKLNDAQAPK;

(SEQ ID NO. 377)
ADAQQNNFNK-[BM]-DPSQSTNVLGEAKKLNESQAPK;

(SEQ ID NO. 378)
AQHDE-[BM]-DPSQSANVLGEAQKLNDSQAPK;

(SEQ ID NO. 379)
VDNKFNK-[BM]-DPSQSANLLAEAKKLNDAQAPK;

(SEQ ID NO. 380)
AEAKYAK-[BM]-DPSESSELLSEAKKLNKSQAPK;

(SEQ ID NO. 381)
VDAKYAK-[BM]-DPSQSSELLAEAKKLNDAQAPK;

(SEQ ID NO. 382)
VDAKYAK-[BM]-DPSQSSELLAEAKKLNDSQAPK;

(SEQ ID NO. 383)
AEAKYAK-[BM]-DPSQSSELLSEAKKLNDSQAPK;

(SEQ ID NO. 384)
VDAKYAK-[BM]-DPSQSSELLSEAKKLNDSQAPK;

(SEQ ID NO. 385)
VDAKYAK-[BM]-DPSQSSELLAEAKKLNKAQAPK;
and

AEAKYAK-[BM]-DPSQSSELLAEAKKLNKAQAPK;
``` wherein [BM] is an CAIX binding motif as defined in any one of items 1-103.

134. CAIX binding polypeptide according to item 133, which comprises an amino acid sequence selected from SEQ ID NO:365-368.

135. CAIX binding polypeptide according to any one of items 1-133, which comprises an amino acid sequence selected from:

```
ix)
                                       (SEQ ID NO. 384)
VDAKYAK-[BM]-DPSQSSELLSEAKKLNDSQAPK;
``` wherein [BM] is an CAIX binding motif as defined in any one of items 1-103; and
x) an amino acid sequence which has at least 83% identity to the sequence defined in ix).

136. CAIX binding polypeptide according to item 135, in which sequence ix) is selected from SEQ ID NO:227-339 and SEQ ID NO:350-354.

137. CAIX binding polypeptide according to item 136, in which sequence ix) is selected from SEQ ID NO:227-339.

138. CAIX binding polypeptide according to item 137, in which sequence ix) is selected from SEQ ID NO:227-230 and SEQ ID NO:232-267.

139. CAIX binding polypeptide according to item 138, in which sequence ix) is selected from SEQ ID NO:227-230, SEQ ID NO:232 and SEQ ID NO:234-263.

140. CAIX binding polypeptide according to item 137, in which sequence ix) is selected from SEQ ID NO:227-240.

141. CAIX binding polypeptide according to item 140, in which sequence ix) is selected from SEQ ID NO:227-234 and SEQ ID NO:236-239.

142. CAIX binding polypeptide according to item 141, in which sequence ix) is SEQ ID NO:227-231.

143. CAIX binding polypeptide according to item 138 or 142, in which sequence ix) is SEQ ID NO:227-230.

144. CAIX binding polypeptide according to item 143, in which sequence ix) is SEQ ID NO:227-229.

145. CAIX binding polypeptide according to any preceding item, which is capable of binding to CAIX such that the $K_D$ value of the interaction is at most $1\times10^{-6}$ M, such as at most $1\times10^{-7}$ M, such as at most $1\times10^{-8}$ M, such as at most $1\times10^{-9}$ M.

146. CAIX binding polypeptide according to any preceding item which comprises additional amino acids at the C-terminal and/or N-terminal end.

147. CAIX binding polypeptide according to item 146, wherein said additional amino acid(s) improve(s) production, purification, stabilization in vivo or in vitro, coupling or detection of the polypeptide.

148. CAIX binding polypeptide according to any preceding item in multimeric form, comprising at least two CAIX binding polypeptide monomer units, whose amino acid sequences may be the same or different.

149. CAIX binding polypeptide according to item 148, wherein said CAIX binding polypeptide monomer units are covalently coupled together.

150. CAIX binding polypeptide according to item 149, wherein the CAIX binding polypeptide monomer units are expressed as a fusion protein.

151. CAIX binding polypeptide according to item 148, in dimeric form.

152. Fusion protein or conjugate comprising
a first moiety consisting of CAIX binding polypeptide according to any preceding item; and
a second moiety consisting of a polypeptide having a desired biological activity.

153. Fusion protein or conjugate according to item 152, wherein said desired biological activity is a therapeutic activity.

154. Fusion protein or conjugate according to item 152, wherein said desired biological activity is a binding activity.

155. Fusion protein or conjugate according to item 154, wherein said binding activity is albumin binding activity which increases in vivo half-life of the fusion protein or conjugate.

156. Fusion protein or conjugate according to item 155, wherein said albumin binding activity comprises the albumin binding domain of streptococcal protein G or a derivative thereof.

157. Fusion protein or conjugate according to item 152, wherein said desired biological activity is an enzymatic activity.

158. Fusion protein or conjugate according to item 153, wherein the second moiety having a desired biological activity is a therapeutically active polypeptide.

159. Fusion protein or conjugate according to any one of items 152, 153 and 157, wherein the second moiety having a desired biological activity is selected from the group consisting of human endogenous enzymes, hormones, growth factors, chemokines, cytokines and lymphokines.

160. CAIX binding polypeptide, fusion protein or conjugate according to any preceding item, further comprising a cytotoxic agent.

161. CAIX binding polypeptide, fusion protein or conjugate according to item 160, wherein said cytotoxic agent is selected from the group consisting of auristatin, anthracycline, calicheamycin, combretastatin, doxorubicin, duocarmycin, the CC-1065 anti-tumorantibiotic, ecteinsascidin, geldanamycin, maytansinoid, methotrexate, mycotoxin, taxol, ricin, bouganin, gelonin, pseudomonas exotoxin 38 (PE38), diphtheria toxin (DT), and their analogues, and derivates thereof and combinations thereof.

162. CAIX binding polypeptide, fusion protein or conjugate according to any preceding item, further comprising a label.

163. CAIX binding polypeptide, fusion protein or conjugate according to item 162, wherein said label is selected from the group consisting of fluorescent dyes and metals, chromophoric dyes, chemiluminescent compounds and bioluminescent proteins, enzymes, radionuclides and particles.

164. CAIX binding polypeptide, fusion protein or conjugate according to any preceding item, comprising a chelating environment provided by a polyaminopolycarboxylate chelator conjugated to the CAIX binding polypeptide via a thiol group of a cysteine residue or an amine group of a lysine residue.

165. CAIX binding polypeptide, fusion protein or conjugate according to item 164, wherein the polyaminopolycarboxylate chelator is 1,4,7,10-tetraazacyclododecane-1,4,7,10-tetraacetic acid or a derivative thereof.

166. CAIX binding polypeptide, fusion protein or conjugate according to item 165, wherein the 1,4,7,10-tetraazacyclododecane-1,4,7,10-tetraacetic acid derivative is 1,4,7,10-tetraazacyclododecane-1,4,7-tris-acetic acid-10-maleimidoethylacetamide.

167. CAIX binding polypeptide, fusion protein or conjugate according to item 164, wherein the polyaminopolycarboxylate chelator is 1,4,7-triazacyclononane-1,4,7-triacetic acid or a derivative thereof.

168. CAIX binding polypeptide, fusion protein or conjugate according to item 164, wherein the polyaminopolycarboxylate chelator is diethylenetriaminepentaacetic acid or derivatives thereof.

169. A polynucleotide encoding a polypeptide according to any one of items 1-159.

170. Expression vector comprising a polynucleotide according to item 169.

171. Host cell comprising an expression vector according to item 170.

172. Method of producing a polypeptide according to any one of items 1-159, comprising
  culturing a host cell according to item 171 under conditions permissive of expression of said polypeptide from said expression vector, and
  isolating said polypeptide.

173. Composition comprising a CAIX binding polypeptide, fusion protein or conjugate according to any one of items 1-168 and at least one pharmaceutically acceptable excipient or carrier.

174. Composition according to item 165, further comprising at least one additional active agent.

175. CAIX binding polypeptide, fusion protein or conjugate according to any one of items 1-168 or a composition according to any one of items 173-174 for use as a medicament, a diagnostic agent or a prognostic agent.

176. CAIX binding polypeptide, fusion protein, conjugate or composition for use according to item 175, wherein said polypeptide, fusion protein, conjugate or composition modulates CAIX function in vivo.

177. CAIX binding polypeptide, fusion protein, conjugate or composition for use according to item 175 or 176, in the treatment, diagnosis or prognosis of a CAIX related condition.

178. CAIX binding polypeptide, fusion protein, conjugate or composition for use according to item 177, wherein said CAIX related condition is cancer.

179. CAIX binding polypeptide, fusion protein, conjugate or composition for use according to item 178, wherein said cancer is selected from the group consisting of kidney cancer, lung cancer, colon cancer, breast cancer, cervical cancer, bladder cancer, ovarian cancer, vulval cancer, brain cancer, head and neck cancer, soft tissue sarcoma, astrocytomas, cancer of the oral cavity and any cancer manifested by solid tumors with hypoxia and CAIX expression.

180. Method of detecting CAIX, comprising providing a sample suspected to contain CAIX, contacting said sample with a CAIX binding polypeptide, fusion protein or conjugate according to any one of items 1-168 or a composition according to any one of items 173-174, and detecting the binding of the CAIX binding polypeptide, fusion protein, conjugate or composition to indicate the presence of CAIX in the sample.

181. Method for determining the presence of CAIX in a subject, the method comprising the steps:
  contacting the subject, or a sample isolated from the subject, with a CAIX binding polypeptide, fusion protein or conjugate according to any one of items 1-168 or a composition according to any one of items 173-174, and
  obtaining a value corresponding to the amount of the CAIX binding polypeptide, fusion protein, conjugate or composition that has bound in said subject or to said sample.

182. Method according to item 181, further comprising a step of comparing said value to a reference.

183. Method according to item 181 or 182, wherein said subject is a mammalian subject, such as a human subject.

184. Method according to any one of items 180-183, wherein the method is performed in vivo.

185. Method according to any one of items 180-183, wherein the method is performed in vitro.

186. Method of treatment of a CAIX related condition, comprising administering to a subject in need thereof an effective amount of a CAIX binding polypeptide, fusion protein or conjugate according to any one of items 1-168 or a composition according to any one of items 173-174.

187. Method according to item 186, wherein said CAIX binding polypeptide, fusion protein or conjugate or composition modulates CAIX function in vivo.

188. Method according to item 186 or 187, wherein said CAIX related condition is cancer.

189. Method according to item 188, wherein said cancer is selected from the group consisting of kidney cancer, lung cancer, colon cancer, breast cancer, cervical cancer, bladder cancer, ovarian cancer, vulval cancer, brain cancer, head and neck cancer, soft tissue sarcoma, astrocytomas, cancer of the oral cavity and any cancer manifested by solid tumors with hypoxia and CAIX expression.

The invention claimed is:

1. A CAIX binding polypeptide, comprising a CAIX binding motif BM, which motif consists of the amino acid sequence:

i)
$$EX_2X_3X_4AX_6X_7EIX_{10}\ X_{11}LPNLX_{16}X_{17}X_{18}QX_{20}\ X_{21}AFIX_{25}X_{26}LWD$$
(SEQ ID NO: 369)

wherein, independently from each other,
$X_2$ is selected from D, H, N, Q and W;
$X_3$ is selected from I, L, Q, R, and W;
$X_4$ is selected from A, F, W and Y;
$X_6$ is selected from A, G and S;
$X_7$ is selected from G, I, V and W;
$X_{10}$ is selected from A, D, E, G, N, Q, R, S and T;
$X_{11}$ is selected from D, E and S;
$X_{16}$ is selected from N and T;
$X_{17}$ is selected from A, D, E, I, Q, T and V;
$X_{18}$ is selected from A, D, E, F, G, H, N, Q, R, S and Y;
$X_{20}$ is R;
$X_{21}$ is selected from D, H and N;
$X_{25}$ is Y;
$X_{26}$ is selected from K and S.

2. The CAIX binding polypeptide according to claim 1, wherein sequence i) fulfills at least seven of the twelve conditions I-XII:
   I. $X_2$ is N;
   II. $X_3$ is selected from I and L;

III. $X_4$ is F;
IV. $X_6$ is G;
V. $X_7$ is W;
VI. $X_{10}$ is selected from D and S;
VII. $X_{11}$ is D;
VIII. $X_{16}$ is T;
IX. $X_{17}$ is selected from E and D;
X. $X_{18}$ is selected from D, Y, E and S;
XI. $X_{21}$ is N; and
XII. $X_{26}$ is K.

3. The CAIX binding polypeptide according to claim 1, wherein sequence i) is selected from SEQ ID NO:1-44, 46-47, 50-56, 58-61, 63, 65-68, 70, 72, 74-84, 86-87, 90-93, 97-99, 102, 105-108, 110-111 and 113.

4. The CAIX binding polypeptide according to claim 1, wherein said CAIX binding motif forms part of a three-helix bundle protein domain.

5. The CAIX binding polypeptide according to claim 1, which comprises the amino acid sequence:

```
iii)
                                    (SEQ ID NO: 371)
K-[BM]-DPSQS X_aX_bLLX_c EAKKL NDX_dQ;
``` wherein
[BM] is an CAIX binding motif as defined in claim 1;
$X_a$ is selected from A and S;
$X_b$ is selected from N and E;
$X_c$ is selected from A, S and C;
$X_d$ is selected from A and S.

6. The CAIX binding polypeptide according to claim 5, wherein sequence iii) is selected from any one of SEQ ID NO:114-157, 160-161, 163-169, 171-174, 176, 178-181, 183, 185, 187-197, 199-200, 203-206, 210-212, 215, 218-221, 223-224 and 226.

7. The CAIX binding polypeptide according to claim 1, which comprises the amino acid sequence:

```
v)
                                    (SEQ ID NO: 384)
VDAKYAK-[BM]-DPSQSSELLSEAKKLNDSQAPK;
``` wherein [BM] is an CAIX binding motif as defined in claim 1.

8. The CAIX binding polypeptide according to claim 7, in which sequence v) is selected from SEQ ID NO:227-270, 272-273, 276-282, 284-287, 289, 291-294, 296, 298, 300-310, 312-313, 316-319, 323-325, 328, 331-334, 336-337 and 339.

9. A fusion protein or conjugate comprising
a first moiety consisting of CAIX binding polypeptide according to claim 1; and
a second moiety consisting of a polypeptide having a desired biological activity.

10. A polynucleotide encoding a polypeptide according to claim 1.

11. A composition comprising a CAIX binding polypeptide according to claim 1 and at least one pharmaceutically acceptable excipient or carrier.

12. A method of detecting CAIX comprising contacting a sample suspected to contain CAIX with the CAIX binding polypeptide according to claim 1; and detecting the binding of the CAIX binding polypeptide to indicate the presence of CAIX in the sample.

13. The CAIX binding polypeptide according to claim 3, wherein sequence i) is selected from SEQ ID NO:1-14.

14. The CAIX binding polypeptide according to claim 13, wherein sequence i) is selected from SEQ ID NO:1-4.

15. The CAIX binding polypeptide according to claim 6, wherein sequence iii) is selected from any one of SEQ ID NO:114-127.

16. The CAIX binding polypeptide according to claim 15, wherein sequence iii) is selected from any one of SEQ ID NO:114-117.

17. The CAIX binding polypeptide according to claim 8, in which sequence v) is selected from SEQ ID NO:227-240.

18. The CAIX binding polypeptide according to claim 17, in which sequence v) is selected from SEQ ID NO:227-230.

19. The method of claim 12 wherein the CAIX binding polypeptide is a component of a fusion protein or a conjugate.

* * * * *